US007238502B2

(12) United States Patent
Kröger et al.

(10) Patent No.: US 7,238,502 B2
(45) Date of Patent: Jul. 3, 2007

(54) METHOD FOR ZYMOTIC PRODUCTION OF FINE CHEMICALS (META) CONTAINING SULPHUR

(75) Inventors: Burkhard Kröger, Limburgerhof (DE); Oskar Zelder, Speyer (DE); Corinna Kolpprogge, Mannheim (DE); Hartwig Schröder, Nussloch (DE); Stefan Häfner, Ludwigshafen (DE)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 10/525,674

(22) PCT Filed: Aug. 26, 2003

(86) PCT No.: PCT/EP03/09452

§ 371 (c)(1),
(2), (4) Date: Feb. 24, 2005

(87) PCT Pub. No.: WO2004/024932

PCT Pub. Date: Mar. 25, 2004

(65) Prior Publication Data

US 2006/0003425 A1    Jan. 5, 2006

(30) Foreign Application Priority Data

Aug. 26, 2002  (DE) ................. 102 39 073

(51) Int. Cl.
C12P 13/12 (2006.01)
C12P 21/06 (2006.01)
C12N 1/21 (2006.01)

(52) U.S. Cl. ............... 435/113; 435/193; 435/15; 435/252.3; 435/252.32; 536/23.2

(58) Field of Classification Search ............ None
See application file for complete search history.

(56) References Cited

U.S. PATENT DOCUMENTS

| 4,489,160 | A | 12/1984 | Katsumata et al. |
| 4,601,893 | A | 7/1986 | Cardinal |
| 5,158,891 | A | 10/1992 | Takeda et al. |
| 5,175,108 | A | 12/1992 | Bachmann et al. |
| 5,965,391 | A | 10/1999 | Reinscheid et al. |
| 2002/0110877 | A1* | 8/2002 | Bathe et al. ............... 435/113 |
| 2003/0170775 | A1 | 9/2003 | Pompejus et al. |

FOREIGN PATENT DOCUMENTS

| DE | 10046870 A1 | 3/2002 |
| EP | 0472869 A2 | 3/1992 |
| EP | 1108790 A2 | 6/2001 |
| JP | 10-229891 A | 9/1998 |
| WO | WO-96/15246 A1 | 5/1996 |
| WO | WO-02/10206 | 2/2002 |
| WO | WO-02/18613 | 3/2002 |
| WO | WO-03/087386 A3 | 10/2003 |
| WO | WO-03/100072 A2 | 12/2003 |
| WO | WO-2004/024931 | 3/2004 |
| WO | WO-2004/024933 | 3/2004 |

OTHER PUBLICATIONS

U.S. Appl. No. 10/511,302, Kröger et al.
Patek, M., et al., "Leucine Synthesis in *Corynebacterium glutamicum*: Enzyme Activities, Structure of leuA, and Effect of leuA Inactivation on Lysine Synthesis", Applied and Environmental Microbiology, vol. 60, No. 1, 1994, pp. 133-140.
Bolivar, F., "Molecular Cloning Vectors Derived From The CoLE1 Type Plasmid pMB1", Life Sciences, vol. 25, 1979, pp. 807-818.
Vieira, J., et al., "The pUC plasmids, an M13mp7-derived system for insertion mutagenesis and sequencing with synthetic universal primers", Gene, vol. 19, 1982, pp. 259-268.
Malakhova, I. I., et al., "Thin-Layer Chromatography of Free Amino Acids. Selection of Conditions for the Separation of L-Lysine, L-Homoserine, and L-Threonine", Biotekhnologiya, vol. 11, 1996, pp. 27-32.
Sanger, F., et al., "DNA sequencing with chain-terminating inhibitors", Proc. Natl. Acad. Sci. USA, vol. 74, No. 12, 1977, pp. 5463-5467.
Dunican, L. K., et al., "High Frequency Transformation of Whole Cells of Amino Acid Producing Coryneform Bacteria Using High Voltage Electroporation", Biotechnology, vol. 7, 1989, pp. 1067-1070.
Simon, R., et al., "A Broad Host Range Mobilization System for In Vivo Genetic Engineering: Transposon Mutagenesis in Gram Negative Bacteria", Biotechnology, vol. 1, 1983, pp. 784-791.
Schrumpf, B., et al., "A Functionally Split Pathway for Lysne Synthesis in *Corynebacterium glutamicum*", Journal of Bacteriology, vol. 173, No. 14, 1991, pp. 4510-4516.
O'Regan, M., et al., "Cloning and nucleotide sequence of the phosphoenolpyruvate carboxylase-coding gene of *Corynebacterium glutamicum* ATCC13032", Gene, vol. 77, 1989, pp. 237-251.
Grant, S. G. N., et al., "Differential plasmid rescue from transgenic mouse DNAs into *Escherichia coli* methylation-restriction mutants", Proc. Natl. Acad. Sci. USA, vol. 87, 1990, pp. 4645-4649.
Itakura, K., et al., "Synthesis and Use of Synthetic Oligonucleotides", Ann. Rev. Biochem., vol. 53, 1984, pp. 323-356.
Jensen, P. R., et al., "Artificial Promoters for Metabolic Optimization", Biotechnology and Bioengineering, vol. 58, 1998, pp. 191-195.
Narang, S. A., "Tetrahedron Report No. 140—DNA Synthesis", Tetrahedron, vol. 39, No. 1, 1983, pp. 3-22.
Sonnen, H., et al., "Characterization of pGA1, a new plasmid from *Corynebacterium glutamicum* LP-6", Gene, vol. 107, 1991, pp. 69-74.

(Continued)

*Primary Examiner*—Rebecca E. Prouty
*Assistant Examiner*—M. Y. Meah
(74) *Attorney, Agent, or Firm*—Connolly Bove Lodge & Hutz LLP

(57) ABSTRACT

The invention relates to methods for the fermentative production of sulfur-containing fine chemicals, in particular L-methionine, by using bacteria which express a nucleotide sequence coding for a methionine synthase (metA) gene.

21 Claims, 3 Drawing Sheets

OTHER PUBLICATIONS

Bernard, P., et al., "The F Plasmid CcdB Protein Induces Efficient ATP-dependent DNA Cleavage by Gyrase", J. Mol. Biol., vol. 234, 1993, pp. 534-541.

Sahm, H., et al., "Pathway Analysis and Metabolic Engineering in Corynebacterium glutamicum", Biol. Chem., vol. 381, 2000, pp. 899-910.

Itakura, K., et al., "Expression in Escherichia coli of a Chemically Synthesized Gene for the Hormone Somatostatin", Science, vol. 198, 1977, pp. 1056-1063.

Staden, R., "The current status and portability of our sequence handling software", Nucleic Acids Research, vol. 14, No. 1, 1986, pp. 217-231.

Hochuli, E., et al., "Genetic Approach to Facilitate Purification of Recombinant Proteins With a Novel Metal Chelate Adsorbent", Biotechnology, vol. 6, 1988, pp. 1321-1325.

Makrides, S., "Strategies for Achieving High-Level Expression of Genes in Escherichia coli", Microbiological Reviews, vol. 60, No. 3, 1996, pp. 512-538.

Arkin, A. P., et al., "An algorithm for protein engineering: Simulations of recursive ensemble mutagenesis", Proc. Natl. Acad. Sci., USA, vol. 89, 1992, pp. 7811-7815.

Eikmanns, B. J., et al., "A family of Corynebacterium glutamicum/ Escherichia coli shuttle vectors for cloning, controlled gene expression, and promoter probing", Gene, vol. 102, 1991, pp. 93-98.

Ike, Y., et al., "Solid phase synthesis of polynucleotides. VIII. Synthesis of mixed oligodeoxyribonucleotides by the phosphotriester solid phase method", Nucleic Acids Research, vol. 11, No. 2, 1983, pp. 477-488.

Malumbres, M., et al., "Codon preference in Corynebacteria", Gene, vol. 134, 1993, pp. 15-24.

Kohara, Y., et al., "The Physical Map of the Whole E. coli Chromosome: Application of a New Strategy for Rapid Analysis and Sorting of a Large Genomic Library", Cell, vol. 50, 1987, pp. 495-508.

Butler, B. A., "Sequence Analysis Using GCG", Methods of Biochemical Analysis, vol. 39, 1998, pp. 74-97.

Tauch, A., et al., "The Erythromycin Resistance Gene of the Corynebacterium xerosis R-plasmid pTP10 Also Carrying Chloramphenicol, Kanamycin, and Tetracycline Resistances is Capable of Transposition in Corynebacterium glutamicum", Plasmid, vol. 33, 1995, pp. 168-179.

Liebl, W., et al., "High efficiency electroporation of intact Corynebacterium glutamicum cells", FEMS Microbiology Letters 65, 1989, pp. 299-304.

Lennox, E. S., "Transduction of Linked Genetic Characters of the Host by Bacteriophage P1", Virology, vol. 1, 1955, pp. 190-206.

Liebl, W., et al., "Transfer of Brevibacterium divaricatum DSM 20297[1], "Brevibacterium flavum" DSM 20411, "Brevibacterium lactofermentum" DSM 20412 and DSM 1412, and Corynebacterium lilium DSM 20137[T] to Corynebacterium glutamicum and Their Distinction by rRNA Gene Restriction Patterns", International Journal of Systematic Bacteriology, vol. 41, No. 2, 1991, pp. 255-260.

Thierbach, G., et al., "Transformation of spheroplasts and protoplasts of Corynebacterium glutamicum", Appl. Microbiol. Biotechnol., vol. 29, 1988, pp. 356-362.

Serwold-Davis, T. M., et al., "Localization of an origin of replication in Corynebacterium diphtheriae broad host range plasmid pNG2 that also functions in Escherichia coli", FEMS Microbiology Letters, vol. 66, 1990, pp. 119-124.

Patek, M., et al., "Promoters from Corynebacterium glutamicum: cloning, molecular analysis and search for a consensus motif", Microbiology, vol. 142, 1996, pp. 1297-1309.

Ben-Bassat, A., et al., "Processing of the Initiation Methionine from Proteins: Properties of the Escherichia coli Methionine Aminopeptidase and its Gene Structure", Journal of Bacteriology, vol. 169, No. 2, 1987, pp. 751-757.

Tsuchiya, M., et al., "Genetic Control Systems of Escherichia coli Can Confer Inducible Expression of Cloned Genes in Coryneform Bacteria", Biotechnology, vol. 6, 1988, pp. 428-430.

Marck, C., "DNA Strider': a 'C' program for the fast analysis of DNA and protein sequences on the Apple Macintosh family of computers", Nucleic Acids Research, vol. 16, No. 5, 1988, pp. 1829-1836.

Guerrero, C., et al., "Directed mutagenesis of a regulatory palindromic sequence upstream from the Brevibacterium lactofermentum tryptophan operon", Gene, vol. 138, 1994, pp. 35-41.

Wahl, G. M., et al., "Cosmid vectors for rapid genomic walking, restriction mapping, and gene transfer", Proc. Natl. Acad. Sci. USA, vol. 84, 1987, pp. 2160-2164.

Eikmanns, B. J., et al., "Molecular Aspects of lysine, threonine, and isoleucine biosynthesis in Corynebacterium glutamicum", Atonie van Leeuwenhoek, vol. 64, 1993, pp. 145-163.

Reinscheid, D. J., et al., "Stable Expression of hom-1-thrB in Corynebacterium glutamicum and Its Effect on the Carbon Flux to Threonine and Related Amino Acids", Applied and Environmental Microbiology, vol. 60, No. 1, 1994, pp. 126-132.

Motoyama, H., et al., "Overproduction of $_L$-Lysine from Methanol by Methylobacillus glycogenes Derivatives Carrying a Plasmid with a Mutated dapA Gene", Applied and Environmental Microbiology, vol. 67, No. 7, 2001, pp. 3064-3070.

Sahin-Toth, M., et al., "Cysteine scanning mutagenesis of the N-terminal 32 amino acid resideuces in the lactose permease of Escherichia coli", Protein Sciences, vol. 3, 1994, pp. 240-247.

Schäfer, A., et al., "Small mobilizable multi-purpose cloning vectors derived from the Escherichia coli plasmids pK18 and pK19: selection of defined deletions in the chromosome of Corynebacterium glutamicum", Gene, vol. 145, 1994, pp. 69-73.

Schwarzer, A., et al., "Manipulation of Corynebacterium glutamicum by Gene Disruption and Replacement", Biotechnology, vol. 9, 1991, pp. 84-87.

Delagrave, S., et al., "Recursive ensemble mutagenesis", Protein Engineering, vol. 6, No. 3, 1993, pp. 327-331.

Pearson, W. R., et al., "Improved tools for biological sequence comparison", Proc. Natl. Acad. Sci. USA, vol. 85, 1988, pp. 2444-2448.

Eikmanns, B. J., et al., "Nucleotide sequence, expression and transcriptional analysis of the Corynebacterium glutamicum gltA gene encoding citrate synthase", Microbiology, vol. 140, 1994, pp. 1817-1828.

Tauch, A., et al., "Corynebacterium glutamicum DNA is subjected to methylation-restriction in Escherichia coli", FEMS Microbiology Letters vol. 123, 1994, pp. 343-348.

Labarre, J., et al., "Gene Replacement, Integration, and Amplification at the gdhA Locus of Corynebacterium glutamicum", Journal of Bacteriology, vol. 175, No. 4, 1993, pp. 1001-1007.

Martin, J.F., et al., "Cloning Systems in Amino Acid-Producing Corynebacteria", Biotechnology, vol. 5, 1987, pp. 137-146.

Eikmanns, B. J., et al., "Identification, Sequence Analysis, and Expression of a Corynebacterium glutamicum Gene Cluster Encoding the Three Glycolytic Enzymes Glyceraldehyde-3-Phosphate Dehydrogenase, 3-Phosphoglycerate Kinase, and Triosephosphate Isomerase", Journal of Bacteriology, vol. 174, No. 19, 1992, pp. 6076-6086.

Schmidt, S., et al., "Near infrared spectroscopy in fermentation and quality control for amino acid production", Bioprocess Engineering, vol. 19, 1998, pp. 67-70.

Spratt, B., et al., "Kanamycin-resistant vectors that are analogues of plasmids pUC8, pUC9, pEMBL8 and pEMBL9", Gene, vol. 41, 1986, pp. 337-342.

Kase, H., et al., "$_L$-Methionine Production by Methionine Analog-resistant Mutants of Corynebacterium glutamicum", Agr. Biol. Chem., vol. 39, No. 1, 1975, pp. 153-160.

Hwang, B.-J., et al., "Corynebacterium glutamicum Utilizes both Transsulfuration and Direct Sulfhydrylation Pathways for Methionine Biosynthesis", Journal of Bacteriology, vol. 184, No. 5, 2002, pp. 1277-1286.

Park, S.-D., et al., "Isolation and Analysis of metA, a Methionine Biosynthetic Gene Encoding Homoserine Acetyltransferase in Corynebacterium glutamicum", Mol. Cells, vol. 8, No. 3, 1998, pp. 286-294.

* cited by examiner

SEQUENCE LISTING

```
<160> NUMBER OF SEQ ID NOS: 69

<210> SEQ ID NO 1
<211> LENGTH: 1104
<212> TYPE: DNA
<213> ORGANISM: Corynebacterium diphteriae
<220> FEATURE:
<221> NAME/KEY: CDS
<222> LOCATION: (1)..(1101)
<223> OTHER INFORMATION: RDI00386

<400> SEQUENCE: 1 atg ctc acc acc aca ggg acg ctc acg cac caa aaa atc gga gac ttt       48
Met Leu Thr Thr Thr Gly Thr Leu Thr His Gln Lys Ile Gly Asp Phe
  1               5                  10                  15 tac acc gaa gcc gga gcg acg ctt cac gac gta acc atc gcc tac caa       96
```

```
                                                              -continued

Tyr Thr Glu Ala Gly Ala Thr Leu His Asp Val Thr Ile Ala Tyr Gln
         20                  25                  30 gca tgg ggc cac tac acc ggc acc aat ctc atc gtt ctc gaa cat gcc        144
Ala Trp Gly His Tyr Thr Gly Thr Asn Leu Ile Val Leu Glu His Ala
     35                  40                  45 ctg acc ggc gac tct aac gct att tca tgg tgg gac gga ctg att ggc        192
Leu Thr Gly Asp Ser Asn Ala Ile Ser Trp Trp Asp Gly Leu Ile Gly
 50                  55                  60 cct ggc aaa gca ctc gac acc aac cgc tac tgc atc cta tgc acc aac        240
Pro Gly Lys Ala Leu Asp Thr Asn Arg Tyr Cys Ile Leu Cys Thr Asn
 65                  70                  75                  80 gtg ctc gga gga tgc aaa gga tcc acc gga ccg agc agt cca cac cca        288
Val Leu Gly Gly Cys Lys Gly Ser Thr Gly Pro Ser Ser Pro His Pro
             85                  90                  95 gac gga aaa cca tgg gga tcc aga ttt cca gcc ctt tca atc cgt gac        336
Asp Gly Lys Pro Trp Gly Ser Arg Phe Pro Ala Leu Ser Ile Arg Asp
         100                 105                 110 ctt gtc aat gcc gaa aaa caa ctt ttc gac cac ctc ggc atc aat aaa        384
Leu Val Asn Ala Glu Lys Gln Leu Phe Asp His Leu Gly Ile Asn Lys
     115                 120                 125 att cac gca atc atc ggc gga tcc atg gga ggc gca cgc acc ctc gaa        432
Ile His Ala Ile Ile Gly Gly Ser Met Gly Gly Ala Arg Thr Leu Glu
 130                 135                 140 tgg gct gca ctc cac cca cac atg atg acg act gga ttc gtc ata gca        480
Trp Ala Ala Leu His Pro His Met Met Thr Thr Gly Phe Val Ile Ala
145                 150                 155                 160 gtc tca gca cgc gca agc gct tgg caa atc ggt att caa act gca caa        528
Val Ser Ala Arg Ala Ser Ala Trp Gln Ile Gly Ile Gln Thr Ala Gln
             165                 170                 175 atc agc gcc ata gaa ctc gac ccc cac tgg aac ggc ggc gat tac tac        576
Ile Ser Ala Ile Glu Leu Asp Pro His Trp Asn Gly Gly Asp Tyr Tyr
         180                 185                 190 agc ggt cac gca cca tgg gaa gga atc gcc gcc gct cgc cgg atc gcc        624
Ser Gly His Ala Pro Trp Glu Gly Ile Ala Ala Ala Arg Arg Ile Ala
     195                 200                 205 cac ctc acc tat cgc ggc gaa cta gaa ata gac gaa cga ttc ggc act        672
His Leu Thr Tyr Arg Gly Glu Leu Glu Ile Asp Glu Arg Phe Gly Thr
 210                 215                 220 tcc gca caa cac ggt gaa aac cca ctc ggc ccc ttc cga gat cca cat        720
Ser Ala Gln His Gly Glu Asn Pro Leu Gly Pro Phe Arg Asp Pro His
225                 230                 235                 240 caa cgt ttt gcg gtc acg agc tac ctc caa cac caa ggc atc aaa ctc        768
Gln Arg Phe Ala Val Thr Ser Tyr Leu Gln His Gln Gly Ile Lys Leu
             245                 250                 255 gct caa cga ttc gat gca ggt agt tac gtc gtg ctt acc gaa gcc ctc        816
Ala Gln Arg Phe Asp Ala Gly Ser Tyr Val Val Leu Thr Glu Ala Leu
         260                 265                 270 aat cgt cat gac atc gga cgc ggc cga ggc gga ctc aac aaa gcc ctc        864
Asn Arg His Asp Ile Gly Arg Gly Arg Gly Gly Leu Asn Lys Ala Leu
     275                 280                 285 agc gca atc aca gtc ccc atc atg att gct ggc gtt gat acc gat att        912
Ser Ala Ile Thr Val Pro Ile Met Ile Ala Gly Val Asp Thr Asp Ile
 290                 295                 300 ctc tac ccc tat cac cag caa gaa cac cta tca cga aat cta ggc aac        960
Leu Tyr Pro Tyr His Gln Gln Glu His Leu Ser Arg Asn Leu Gly Asn
305                 310                 315                 320 cta ctc gct atg gca aaa atc agc tca cca gta ggc cac gac gct ttc       1008
Leu Leu Ala Met Ala Lys Ile Ser Ser Pro Val Gly His Asp Ala Phe
             325                 330                 335
```

| | | | | | | | | | | | | |
|---|---|---|---|---|---|---|---|---|---|---|---|---|
| ctc | aca | gaa | ttc | cga | caa | atg | gag | cga | atc | cta | aga | cat | ttc | atg | gag | 1056 |
| Leu | Thr | Glu | Phe | Arg | Gln | Met | Glu | Arg | Ile | Leu | Arg | His | Phe | Met | Glu | |
| | | 340 | | | | | 345 | | | | | 350 | | | | |

| ctt | tcg | gaa | gga | atc | gac | gat | tcc | ttc | cga | acc | aaa | cta | gag | cgc | 1101 |
| Leu | Ser | Glu | Gly | Ile | Asp | Asp | Ser | Phe | Arg | Thr | Lys | Leu | Glu | Arg | |
| | 355 | | | | | 360 | | | | | 365 | | | | tga                                                                                    1104

<210> SEQ ID NO 2
<211> LENGTH: 367
<212> TYPE: PRT
<213> ORGANISM: Corynebacterium diphteriae

<400> SEQUENCE:

-continued

```
                    325                 330                 335
Leu Thr Glu Phe Arg Gln Met Glu Arg Ile Leu Arg His Phe Met Glu
                340                 345                 350

Leu Ser Glu Gly Ile Asp Asp Ser Phe Arg Thr Lys Leu Glu Arg
            355                 360                 365

<210> SEQ ID NO 3
<211> LENGTH: 1149
<212> TYPE: DNA
<213> ORGANISM: Mycobacterium leprae
<220> FEATURE:
<221> NAME/KEY: CDS
<222> LOCATION: (1)..(1146)
<223> OTHER INFORMATION: RML02951
<220> FEATURE:
<221> NAME/KEY: unsure
<222> LOCATION: 224 .. 224
<223> OTHER INFORMATION: All occurrences of n indicate any nucleotide

<400> SEQUENCE: 3 atg aca atc tcc aag gtc cct acc cag aag ctg ccg gcc gaa ggc gag      48
Met Thr Ile Ser Lys Val Pro Thr Gln Lys Leu Pro Ala Glu Gly Glu
  1               5                  10                  15 gtc ggc ttg gtc gac atc ggc tca ctt acc acc gaa agc ggt gcc gtc      96
Val Gly Leu Val Asp Ile Gly Ser Leu Thr Thr Glu Ser Gly Ala Val
             20                  25                  30 atc gac gat gtc tgc atc gcc gtt cag cgc tgg ggg gaa ttg tcg ccc     144
Ile Asp Asp Val Cys Ile Ala Val Gln Arg Trp Gly Glu Leu Ser Pro
         35                  40                  45 acg cga gac aac gta gtg atg gta ctg cat gca ctc acc ggt gac tcg     192
Thr Arg Asp Asn Val Val Met Val Leu His Ala Leu Thr Gly Asp Ser
     50                  55                  60 cac atc acc ggg ccc gcc gga ccg gga cat cnc aca ccc ggc tgg tgg     240
His Ile Thr Gly Pro Ala Gly Pro Gly His Xaa Thr Pro Gly Trp Trp
 65                  70                  75                  80 gac tgg ata gct gga ccg ggt gca cca atc gac acc aac cgc tgg tgc     288
Asp Trp Ile Ala Gly Pro Gly Ala Pro Ile Asp Thr Asn Arg Trp Cys
                 85                  90                  95 gcg ata gcc acc aac gtg ctg ggc ggt tgc cgt ggc tcc acc ggc cct     336
Ala Ile Ala Thr Asn Val Leu Gly Gly Cys Arg Gly Ser Thr Gly Pro
            100                 105                 110 agt tcg ctt gcc cgc gac gga aag cct tgg ggt tca aga ttt ccg ctg     384
Ser Ser Leu Ala Arg Asp Gly Lys Pro Trp Gly Ser Arg Phe Pro Leu
        115                 120                 125 ata tct ata cgc gac cag gta gag gca gat atc gct gca ctg gcc gcc     432
Ile Ser Ile Arg Asp Gln Val Glu Ala Asp Ile Ala Ala Leu Ala Ala
    130                 135                 140 atg gga att aca aag gtt gcc gcc gtc gtt gga gga tct atg ggc ggg     480
Met Gly Ile Thr Lys Val Ala Ala Val Val Gly Gly Ser Met Gly Gly
145                 150                 155                 160 gcg cgt gca ctg gaa tgg atc atc ggc cac ccg gac caa gtc cgg gcc     528
Ala Arg Ala Leu Glu Trp Ile Ile Gly His Pro Asp Gln Val Arg Ala
                165                 170                 175 ggg ctg ttg ctg gcg gtc ggt gtg cgc gcc acc gcc gac cag atc ggc     576
Gly Leu Leu Leu Ala Val Gly Val Arg Ala Thr Ala Asp Gln Ile Gly
            180                 185                 190 acc caa acc acc caa atc gca gcc atc aag aca gac ccg aac tgg caa     624
Thr Gln Thr Thr Gln Ile Ala Ala Ile Lys Thr Asp Pro Asn Trp Gln
        195                 200                 205 ggc ggt gac tac tac gag aca ggg agg gca cca gag aac ggc ttg aca     672
Gly Gly Asp Tyr Tyr Glu Thr Gly Arg Ala Pro Glu Asn Gly Leu Thr
    210                 215                 220
```

```
att gcc cgc cgc ttc gcc cac ctg acc tac cgc agc gag gtc gag ctc      720
Ile Ala Arg Arg Phe Ala His Leu Thr Tyr Arg Ser Glu Val Glu Leu
225                 230                 235                 240 gac acc cgg ttt gcc aac aac aac caa ggc aat gag gac ccg gcg acg      768
Asp Thr Arg Phe Ala Asn Asn Asn Gln Gly Asn Glu Asp Pro Ala Thr
            245                 250                 255 ggc ggg cgt tac gca gtg cag agt tac cta gag cac cag ggt gac aag      816
Gly Gly Arg Tyr Ala Val Gln Ser Tyr Leu Glu His Gln Gly Asp Lys
        260                 265                 270 cta ttg gcc cgc ttt gac gca ggc agc tac gtg gtc ttg acc gaa acg      864
Leu Leu Ala Arg Phe Asp Ala Gly Ser Tyr Val Val Leu Thr Glu Thr
    275                 280                 285 ctg aac agc cac gac gtt ggc cgg ggc cgc gga ggg atc ggt aca gcg      912
Leu Asn Ser His Asp Val Gly Arg Gly Arg Gly Gly Ile Gly Thr Ala
290                 295                 300 ctg cgc ggg tgc ccg gta ccg gtg gtg gtg ggt ggc att acc tcg gat      960
Leu Arg Gly Cys Pro Val Pro Val Val Val Gly Gly Ile Thr Ser Asp
305                 310                 315                 320 cgg ctc tac cca ctg cgc ttg cag cag gag ctg gcc gag atg ctg ccg     1008
Arg Leu Tyr Pro Leu Arg Leu Gln Gln Glu Leu Ala Glu Met Leu Pro
            325                 330                 335 ggc tgc acc ggg ctg cag gtt gta gac tcc acc tac ggg cac gac ggc     1056
Gly Cys Thr Gly Leu Gln Val Val Asp Ser Thr Tyr Gly His Asp Gly
        340                 345                 350 ttc ctg gtg gaa tcc gag gcc gtc ggc aaa ttg atc cgt caa acc ctc     1104
Phe Leu Val Glu Ser Glu Ala Val Gly Lys Leu Ile Arg Gln Thr Leu
    355                 360                 365 gaa ttg gcc gac gtg ggt tcc aag gaa gac gcg tgt tcg caa             1146
Glu Leu Ala Asp Val Gly Ser Lys Glu Asp Ala Cys Ser Gln
370                 375                 380 tga                                                                  1149

<210> SEQ ID NO 4
<211> LENGTH: 382
<212> TYPE: PRT
<213> ORGANISM: Mycobacterium leprae
<220> FEATURE:
<221> NAME/KEY: unsure
<222> LOCATION: 75 .. 75
<223> OTHER INFORMATION: All occurrences of Xaa indicate any amino acid

<400> SEQUENCE: 4

Met Thr Ile Ser Lys Val Pro Thr Gln Lys Leu Pro Ala Glu Gly Glu
1               5                   10                  15

Val Gly Leu Val Asp Ile Gly Ser Leu Thr Thr Glu Ser Gly Ala Val
            20                  25                  30

Ile Asp Asp Val Cys Ile Ala Val Gln Arg Trp Gly Glu Leu Ser Pro
        35                  40                  45

Thr Arg Asp Asn Val Val Met Val Leu His Ala Leu Thr Gly Asp Ser
    50                  55                  60

His Ile Thr Gly Pro Ala Gly Pro Gly His Xaa Thr Pro Gly Trp Trp
65                  70                  75                  80

Asp Trp Ile Ala Gly Pro Gly Ala Pro Ile Asp Thr Asn Arg Trp Cys
            85                  90                  95

Ala Ile Ala Thr Asn Val Leu Gly Gly Cys Arg Gly Ser Thr Gly Pro
        100                 105                 110

Ser Ser Leu Ala Arg Asp Gly Lys Pro Trp Gly Ser Arg Phe Pro Leu
    115                 120                 125
```

-continued

```
Ile Ser Ile Arg Asp Gln Val Glu Ala Asp Ile Ala Ala Leu Ala Ala
130                 135                 140

Met Gly Ile Thr Lys Val Ala Ala Val Val Gly Ser Met Gly Gly
145                 150                 155                 160

Ala Arg Ala Leu Glu Trp Ile Ile Gly His Pro Asp Gln Val Arg Ala
                165                 170                 175

Gly Leu Leu Ala Val Gly Val Arg Ala Thr Ala Asp Gln Ile Gly
            180                 185                 190

Thr Gln Thr Thr Gln Ile Ala Ala Ile Lys Thr Asp Pro Asn Trp Gln
        195                 200                 205

Gly Gly Asp Tyr Tyr Glu Thr Gly Arg Ala Pro Glu Asn Gly Leu Thr
210                 215                 220

Ile Ala Arg Arg Phe Ala His Leu Thr Tyr Arg Ser Glu Val Glu Leu
225                 230                 235                 240

Asp Thr Arg Phe Ala Asn Asn Asn Gln Gly Asn Glu Asp Pro Ala Thr
                245                 250                 255

Gly Gly Arg Tyr Ala Val Gln Ser Tyr Leu Glu His Gln Gly Asp Lys
            260                 265                 270

Leu Leu Ala Arg Phe Asp Ala Gly Ser Tyr Val Val Leu Thr Glu Thr
        275                 280                 285

Leu Asn Ser His Asp Val Gly Arg Gly Arg Gly Ile Gly Thr Ala
290                 295                 300

Leu Arg Gly Cys Pro Val Pro Val Val Gly Gly Ile Thr Ser Asp
305                 310                 315                 320

Arg Leu Tyr Pro Leu Arg Leu Gln Gln Glu Leu Ala Glu Met Leu Pro
                325                 330                 335

Gly Cys Thr Gly Leu Gln Val Val Asp Ser Thr Tyr Gly His Asp Gly
            340                 345                 350

Phe Leu Val Glu Ser Glu Ala Val Gly Lys Leu Ile Arg Gln Thr Leu
        355                 360                 365

Glu Leu Ala Asp Val Gly Ser Lys Glu Asp Ala Cys Ser Gln
370                 375                 380

<210> SEQ ID NO 5
<211> LENGTH: 1140
<212> TYPE: DNA
<213> ORGANISM: Mycobacterium tuberculosis
<220> FEATURE:
<221> NAME/KEY: CDS
<222> LOCATION: (1)..(1137)
<223> OTHER INFORMATION: RMTB03565

<400> SEQUENCE: 5 atg acg atc tcc gat gta ccc acc cag acg ctg ccc gcc gaa ggc gaa      48
Met Thr Ile Ser Asp Val Pro Thr Gln Thr Leu Pro Ala Glu Gly Glu
  1               5                  10                  15 atc ggc ctg ata gac gtc ggc tcg ctg caa ctg gaa agc ggg gcg gtg      96
Ile Gly Leu Ile Asp Val Gly Ser Leu Gln Leu Glu Ser Gly Ala Val
             20                  25                  30 atc gac gat gtc tgt atc gcc gtg caa cgc tgg ggc aaa ttg tcg ccc     144
Ile Asp Asp Val Cys Ile Ala Val Gln Arg Trp Gly Lys Leu Ser Pro
         35                  40                  45 gca cgg gac aac gtg gtg gtg gtc ttg cac gcg ctc acc ggc gac tcg     192
Ala Arg Asp Asn Val Val Val Val Leu His Ala Leu Thr Gly Asp Ser
     50                  55                  60 cac atc act gga ccc gcc gga ccc ggc cac ccc acc ccc ggc tgg tgg     240
His Ile Thr Gly Pro Ala Gly Pro Gly His Pro Thr Pro Gly Trp Trp
 65                  70                  75                  80
```

-continued

```
gac ggg gtg gcc ggg ccg agt gcg ccg att gac acc acc cgc tgg tgc       288
Asp Gly Val Ala Gly Pro Ser Ala Pro Ile Asp Thr Thr Arg Trp Cys
                 85                  90                  95 gcg gta gct acc aat gtg ctc ggc ggc tgc cgc ggc tcc acc ggg ccc       336
Ala Val Ala Thr Asn Val Leu Gly Gly Cys Arg Gly Ser Thr Gly Pro
            100                 105                 110 agc tcg ctt gcc cgc gac gga aag cct tgg ggc tca aga ttt ccg ctg       384
Ser Ser Leu Ala Arg Asp Gly Lys Pro Trp Gly Ser Arg Phe Pro Leu
            115                 120                 125 atc tcg ata cgt gac cag gtg cag gcg gac gtc gcg gcg ctg gcc gcg       432
Ile Ser Ile Arg Asp Gln Val Gln Ala Asp Val Ala Ala Leu Ala Ala
        130                 135                 140 ctg ggc atc acc gag gtc gcc gcc gtc gtc ggc ggc tcc atg ggc ggc       480
Leu Gly Ile Thr Glu Val Ala Ala Val Val Gly Gly Ser Met Gly Gly
145                 150                 155                 160 gcc cgg gcc ctg gaa tgg gtg gtc ggc tac ccg gat cgg gtc cga gcc       528
Ala Arg Ala Leu Glu Trp Val Val Gly Tyr Pro Asp Arg Val Arg Ala
                165                 170                 175 gga ttg ctg ctg gcg gtc ggt gcg cgt gcc acc gca gac cag atc ggc       576
Gly Leu Leu Leu Ala Val Gly Ala Arg Ala Thr Ala Asp Gln Ile Gly
            180                 185                 190 acg cag aca acg caa atc gcg gcc atc aaa gcc gac ccg gac tgg cag       624
Thr Gln Thr Thr Gln Ile Ala Ala Ile Lys Ala Asp Pro Asp Trp Gln
            195                 200                 205 agc ggc gac tac cac gag acg ggg agg gca cca gac gcc ggg ctg cga       672
Ser Gly Asp Tyr His Glu Thr Gly Arg Ala Pro Asp Ala Gly Leu Arg
        210                 215                 220 ctc gcc cgc cgc ttc gcg cac ctc acc tac cgc ggc gag atc gag ctc       720
Leu Ala Arg Arg Phe Ala His Leu Thr Tyr Arg Gly Glu Ile Glu Leu
225                 230                 235                 240 gac acc cgg ttc gcc aac cac aac cag ggc aac gag gat ccg acg gcc       768
Asp Thr Arg Phe Ala Asn His Asn Gln Gly Asn Glu Asp Pro Thr Ala
                245                 250                 255 ggc ggg cgc tac gcg gtg caa agt tat ctg gaa cac caa gga gac aaa       816
Gly Gly Arg Tyr Ala Val Gln Ser Tyr Leu Glu His Gln Gly Asp Lys
            260                 265                 270 ctg tta tcc cgg ttc gac gcc ggc agc tac gtg att ctc acc gag gcg       864
Leu Leu Ser Arg Phe Asp Ala Gly Ser Tyr Val Ile Leu Thr Glu Ala
            275                 280                 285 ctc aac agc cac gac gtc ggc cgc ggc cgc ggc ggg gtc tcc gcg gct       912
Leu Asn Ser His Asp Val Gly Arg Gly Arg Gly Gly Val Ser Ala Ala
        290                 295                 300 ctg cgc gcc tgc ccg gtg ccg gtg gtg gtg ggc ggc atc acc tcc gac       960
Leu Arg Ala Cys Pro Val Pro Val Val Val Gly Gly Ile Thr Ser Asp
305                 310                 315                 320 cgg ctc tac ccg ctg cgc ctg cag cag gag ctg gcc gac ctg ctg ccg      1008
Arg Leu Tyr Pro Leu Arg Leu Gln Gln Glu Leu Ala Asp Leu Leu Pro
                325                 330                 335 ggc tgc gcc ggg ctg cga gtc gtc gag tcg gtc tac gga cac gac ggc      1056
Gly Cys Ala Gly Leu Arg Val Val Glu Ser Val Tyr Gly His Asp Gly
            340                 345                 350 ttc ctg gtg gaa acc gag gcc gtg ggc gaa ttg atc cgc cag aca ctg      1104
Phe Leu Val Glu Thr Glu Ala Val Gly Glu Leu Ile Arg Gln Thr Leu
            355                 360                 365 gga ttg gct gat cgt gaa ggc gcg tgt cgg cgg tga                      1140
Gly Leu Ala Asp Arg Glu Gly Ala Cys Arg Arg
        370                 375
```

<210> SEQ ID NO 6

```
<211> LENGTH: 379
<212> TYPE: PRT
<213> ORGANISM: Mycobacterium tuberculosis

<400> SEQUENCE: 6

Met Thr Ile Ser Asp Val Pro Thr Gln Thr Leu Pro Ala Glu Gly Glu
 1               5                  10                  15

Ile Gly Leu Ile Asp Val Gly Ser Leu Gln Leu Glu Ser Gly Ala Val
            20                  25                  30

Ile Asp Val Cys Ile Ala Val Gln Arg Trp Gly Lys Leu Ser Pro
        35                  40                  45

Ala Arg Asp Asn Val Val Val Leu His Ala Leu Thr Gly Asp Ser
 50                  55                  60

His Ile Thr Gly Pro Ala Gly Pro Gly His Pro Thr Pro Gly Trp Trp
 65                  70                  75                  80

Asp Gly Val Ala Gly Pro Ser Ala Pro Ile Asp Thr Thr Arg Trp Cys
                85                  90                  95

Ala Val Ala Thr Asn Val Leu Gly Gly Cys Arg Gly Ser Thr Gly Pro
            100                 105                 110

Ser Ser Leu Ala Arg Asp Gly Lys Pro Trp Gly Ser Arg Phe Pro Leu
        115                 120                 125

Ile Ser Ile Arg Asp Gln Val Gln Ala Asp Val Ala Ala Leu Ala Ala
130                 135                 140

Leu Gly Ile Thr Glu Val Ala Ala Val Val Gly Gly Ser Met Gly Gly
145                 150                 155                 160

Ala Arg Ala Leu Glu Trp Val Val Gly Tyr Pro Asp Arg Val Arg Ala
                165                 170                 175

Gly Leu Leu Leu Ala Val Gly Ala Arg Ala Thr Ala Asp Gln Ile Gly
            180                 185                 190

Thr Gln Thr Thr Gln Ile Ala Ala Ile Lys Ala Asp Pro Asp Trp Gln
        195                 200                 205

Ser Gly Asp Tyr His Glu Thr Gly Arg Ala Pro Asp Ala Gly Leu Arg
210                 215                 220

Leu Ala Arg Arg Phe Ala His Leu Thr Tyr Arg Gly Glu Ile Glu Leu
225                 230                 235                 240

Asp Thr Arg Phe Ala Asn His Asn Gln Gly Asn Glu Asp Pro Thr Ala
                245                 250                 255

Gly Gly Arg Tyr Ala Val Gln Ser Tyr Leu Glu His Gln Gly Asp Lys
            260                 265                 270

Leu Leu Ser Arg Phe Asp Ala Gly Ser Tyr Val Ile Leu Thr Glu Ala
        275                 280                 285

Leu Asn Ser His Asp Val Gly Arg Gly Arg Gly Val Ser Ala Ala
290                 295                 300

Leu Arg Ala Cys Pro Val Pro Val Val Gly Gly Ile Thr Ser Asp
305                 310                 315                 320

Arg Leu Tyr Pro Leu Arg Leu Gln Gln Glu Leu Ala Asp Leu Leu Pro
                325                 330                 335

Gly Cys Ala Gly Leu Arg Val Val Glu Ser Val Tyr Gly His Asp Gly
            340                 345                 350

Phe Leu Val Glu Thr Glu Ala Val Gly Glu Leu Ile Arg Gln Thr Leu
        355                 360                 365

Gly Leu Ala Asp Arg Glu Gly Ala Cys Arg Arg
370                 375
```

<210> SEQ ID NO 7
<211> LENGTH: 972
<212> TYPE: DNA
<213> ORGANISM: Chlorobium tepidum
<220> FEATURE:
<221> NAME/KEY: CDS
<222> LOCATION: (1)..(969)
<223> OTHER INFORMATION: RCL01447

<400> SEQUENCE: 7

| | | | | | | | | | | | | | | | | |
|---|---|---|---|---|---|---|---|---|---|---|---|---|---|---|---|---|
| gtg | agg | gtc | gct | tac | cgt | acc | tgg | ggt | acg | cta | aac | gca | gag | aaa | agc | 48 |
| Val | Arg | Val | Ala | Tyr | Arg | Thr | Trp | Gly | Thr | Leu | Asn | Ala | Glu | Lys | Ser | |
| 1 | | | | 5 | | | | | 10 | | | | | 15 | | |
| aac | gtg | att | ctg | gtc | tgc | cac | gcg | ctg | acc | ggc | aac | gcc | gac | gcc | gac | 96 |
| Asn | Val | Ile | Leu | Val | Cys | His | Ala | Leu | Thr | Gly | Asn | Ala | Asp | Ala | Asp | |
| | | | 20 | | | | | 25 | | | | | 30 | | | |
| agc | tgg | tgg | tgc | ggc | atg | ttc | ggt | gag | gga | cgg | gcg | ttc | gac | gag | act | 144 |
| Ser | Trp | Trp | Cys | Gly | Met | Phe | Gly | Glu | Gly | Arg | Ala | Phe | Asp | Glu | Thr | |
| | | 35 | | | | | 40 | | | | | 45 | | | | |
| cgg | gac | ttc | atc | gta | tgc | agc | aac | gtg | ctt | gga | agc | tgc | tac | gga | acg | 192 |
| Arg | Asp | Phe | Ile | Val | Cys | Ser | Asn | Val | Leu | Gly | Ser | Cys | Tyr | Gly | Thr | |
| | 50 | | | | | 55 | | | | | 60 | | | | | |
| acc | ggg | ccg | atg | tcg | gtg | aat | ccg | ctg | agt | ggc | agg | cac | tac | ggt | ccc | 240 |
| Thr | Gly | Pro | Met | Ser | Val | Asn | Pro | Leu | Ser | Gly | Arg | His | Tyr | Gly | Pro | |
| 65 | | | | | 70 | | | | | 75 | | | | | 80 | |
| gat | ttt | ccg | cgc | att | acc | att | cgc | gac | atg | gtg | aat | gtt | cag | cga | tta | 288 |
| Asp | Phe | Pro | Arg | Ile | Thr | Ile | Arg | Asp | Met | Val | Asn | Val | Gln | Arg | Leu | |
| | | | | 85 | | | | | 90 | | | | | 95 | | |
| ttg | ctt | cgt | tcg | ctc | ggc | atc | gac | cgg | atc | cgg | ctc | atc | gtt | ggt | gca | 336 |
| Leu | Leu | Arg | Ser | Leu | Gly | Ile | Asp | Arg | Ile | Arg | Leu | Ile | Val | Gly | Ala | |
| | | | 100 | | | | | 105 | | | | | 110 | | | |
| tcg | ctt | ggc | ggg | atg | cag | gtg | ctc | gaa | tgg | ggc | gca | atg | tat | ccc | gaa | 384 |
| Ser | Leu | Gly | Gly | Met | Gln | Val | Leu | Glu | Trp | Gly | Ala | Met | Tyr | Pro | Glu | |
| | | 115 | | | | | 120 | | | | | 125 | | | | |
| atg | gcc | ggg | gcg | ctg | atg | ccg | atg | ggc | gtt | tcg | ggt | cgt | cat | tcg | gcg | 432 |
| Met | Ala | Gly | Ala | Leu | Met | Pro | Met | Gly | Val | Ser | Gly | Arg | His | Ser | Ala | |
| | 130 | | | | | 135 | | | | | 140 | | | | | |
| tgg | tgc | atc | gcg | cag | agc | gag | gcg | cag | cgg | cag | gct | atc | gcc | gcc | gat | 480 |
| Trp | Cys | Ile | Ala | Gln | Ser | Glu | Ala | Gln | Arg | Gln | Ala | Ile | Ala | Ala | Asp | |
| 145 | | | | | 150 | | | | | 155 | | | | | 160 | |
| gcg | gag | tgg | caa | gat | ggc | tgg | tat | gat | ccg | gag | gtg | cag | cca | cgc | aaa | 528 |
| Ala | Glu | Trp | Gln | Asp | Gly | Trp | Tyr | Asp | Pro | Glu | Val | Gln | Pro | Arg | Lys | |
| | | | | 165 | | | | | 170 | | | | | 175 | | |
| gga | ctt | gcc | gcc | gcg | cgg | atg | atg | gcg | atg | tgc | acc | tac | cgc | tgc | ttc | 576 |
| Gly | Leu | Ala | Ala | Ala | Arg | Met | Met | Ala | Met | Cys | Thr | Tyr | Arg | Cys | Phe | |
| | | | 180 | | | | | 185 | | | | | 190 | | | |
| gag | aac | tac | cag | caa | cgc | ttt | ggc | cgc | aag | cag | cgc | gag | gac | ggc | ttg | 624 |
| Glu | Asn | Tyr | Gln | Gln | Arg | Phe | Gly | Arg | Lys | Gln | Arg | Glu | Asp | Gly | Leu | |
| | | 195 | | | | | 200 | | | | | 205 | | | | |
| ttc | gaa | gcc | gaa | agc | tac | gtg | cgt | cac | cag | ggc | gac | aag | ctg | gtt | ggg | 672 |
| Phe | Glu | Ala | Glu | Ser | Tyr | Val | Arg | His | Gln | Gly | Asp | Lys | Leu | Val | Gly | |
| | 210 | | | | | 215 | | | | | 220 | | | | | |
| cgc | ttt | gat | gca | aac | acc | tat | atc | acg | ctc | acc | aga | gcg | atg | gac | atg | 720 |
| Arg | Phe | Asp | Ala | Asn | Thr | Tyr | Ile | Thr | Leu | Thr | Arg | Ala | Met | Asp | Met | |
| 225 | | | | | 230 | | | | | 235 | | | | | 240 | |
| cac | gac | ctc | ggg | cgc | gga | cgc | gac | tcc | tac | gaa | gcg | gcg | ctc | gga | gcg | 768 |
| His | Asp | Leu | Gly | Arg | Gly | Arg | Asp | Ser | Tyr | Glu | Ala | Ala | Leu | Gly | Ala | |
| | | | | 245 | | | | | 250 | | | | | 255 | | |
| ctg | aag | atg | ccg | gtc | gag | att | ctc | tcc | atc | gac | tcg | gac | gtg | ctc | tat | 816 |
| Leu | Lys | Met | Pro | Val | Glu | Ile | Leu | Ser | Ile | Asp | Ser | Asp | Val | Leu | Tyr | |
| | | | 260 | | | | | 265 | | | | | 270 | | | |

```
ccc agg cag gag cag gag gaa ctt gcc cgc ctc att ccc ggc tca cgc    864
Pro Arg Gln Glu Gln Glu Glu Leu Ala Arg Leu Ile Pro Gly Ser Arg
        275                 280                 285 ctg ctt ttc ctt gac gaa ccc tat ggc cac gac gcc ttt ctt atc gac    912
Leu Leu Phe Leu Asp Glu Pro Tyr Gly His Asp Ala Phe Leu Ile Asp
    290                 295                 300 acc gag acc gtc agc cgc atg gtc tgc gag ttc aag agg cag ttg ata    960
Thr Glu Thr Val Ser Arg Met Val Cys Glu Phe Lys Arg Gln Leu Ile
305                 310                 315                 320 gtt gac aat tga                                                    972
Val Asp Asn
```

<210> SEQ ID NO 8
<211> LENGTH: 323
<212> TYPE: PRT
<213> ORGANISM: Chlorobium tepidum

<400> SEQUENCE: 8

```
Val Arg Val Ala Tyr Arg Thr Trp Gly Thr Leu Asn Ala Glu Lys Ser
 1               5                  10                  15

Asn Val Ile Leu Val Cys His Ala Leu Thr Gly Asn Ala Asp Ala Asp
                20                  25                  30

Ser Trp Trp Cys Gly Met Phe Glu Gly Arg Ala Phe Asp Glu Thr
        35                  40                  45

Arg Asp Phe Ile Val Cys Ser Asn Val Leu Gly Ser Cys Tyr Gly Thr
    50                  55                  60

Thr Gly Pro Met Ser Val Asn Pro Leu Ser Gly Arg His Tyr Gly Pro
65                  70                  75                  80

Asp Phe Pro Arg Ile Thr Ile Arg Asp Met Val Asn Val Gln Arg Leu
                85                  90                  95

Leu Leu Arg Ser Leu Gly Ile Asp Arg Ile Arg Leu Ile Val Gly Ala
            100                 105                 110

Ser Leu Gly Gly Met Gln Val Leu Glu Trp Gly Ala Met Tyr Pro Glu
        115                 120                 125

Met Ala Gly Ala Leu Met Pro Met Gly Val Ser Gly Arg His Ser Ala
    130                 135                 140

Trp Cys Ile Ala Gln Ser Glu Ala Gln Arg Gln Ala Ile Ala Ala Asp
145                 150                 155                 160

Ala Glu Trp Gln Asp Gly Trp Tyr Asp Pro Glu Val Gln Pro Arg Lys
                165                 170                 175

Gly Leu Ala Ala Arg Met Met Ala Met Cys Thr Tyr Arg Cys Phe
            180                 185                 190

Glu Asn Tyr Gln Gln Arg Phe Gly Arg Lys Gln Arg Glu Asp Gly Leu
        195                 200                 205

Phe Glu Ala Glu Ser Tyr Val Arg His Gln Gly Asp Lys Leu Val Gly
    210                 215                 220

Arg Phe Asp Ala Asn Thr Tyr Ile Thr Leu Thr Arg Ala Met Asp Met
225                 230                 235                 240

His Asp Leu Gly Arg Gly Arg Asp Ser Tyr Glu Ala Ala Leu Gly Ala
                245                 250                 255

Leu Lys Met Pro Val Glu Ile Leu Ser Ile Asp Ser Asp Val Leu Tyr
            260                 265                 270

Pro Arg Gln Glu Gln Glu Glu Leu Ala Arg Leu Ile Pro Gly Ser Arg
        275                 280                 285

Leu Leu Phe Leu Asp Glu Pro Tyr Gly His Asp Ala Phe Leu Ile Asp
    290                 295                 300
```

```
Thr Glu Thr Val Ser Arg Met Val Cys Glu Phe Lys Arg Gln Leu Ile
305                 310                 315                 320

Val Asp Asn

<210> SEQ ID NO 9
<211> LENGTH: 1149
<212> TYPE: DNA
<213> ORGANISM: Caulobacter crescentus
<220> FEATURE:
<221> NAME/KEY: CDS
<222> LOCATION: (1)..(1146)
<223> OTHER INFORMATION: RCO00727

<400> SEQUENCE: 9 atg gct gcg ctc gat ccg atc acg ccc gcc ggc ggg gga acc tgg cgg      48
Met Ala Ala Leu Asp Pro Ile Thr Pro Ala Gly Gly Gly Thr Trp Arg
1               5                   10                  15 ttt cct gcg aat gaa cct ctg cgg ctg gac tcc gga ggc gtc atc gaa      96
Phe Pro Ala Asn Glu Pro Leu Arg Leu Asp Ser Gly Gly Val Ile Glu
                20                  25                  30 ggt ctg gaa atc gcc tac cag acc tac ggc cag ctg aac gcg gac aag     144
Gly Leu Glu Ile Ala Tyr Gln Thr Tyr Gly Gln Leu Asn Ala Asp Lys
            35                  40                  45 tcc aac gcc gtc ctg atc tgc cac gcc ctg acg ggc gac cag cat gtg     192
Ser Asn Ala Val Leu Ile Cys His Ala Leu Thr Gly Asp Gln His Val
        50                  55                  60 gcc tcg ccc cac ccc acc acc ggc aag ccc ggc tgg tgg caa cgc ctt     240
Ala Ser Pro His Pro Thr Thr Gly Lys Pro Gly Trp Trp Gln Arg Leu
65                  70                  75                  80 gtt ggt ccc ggt aag ccg ctg gat ccc gcg cgg cac ttc atc atc tgc     288
Val Gly Pro Gly Lys Pro Leu Asp Pro Ala Arg His Phe Ile Ile Cys
                85                  90                  95 tcg aac gtg atc ggc ggc tgc atg ggc tcg acg ggc ccg gcc tcg atc     336
Ser Asn Val Ile Gly Gly Cys Met Gly Ser Thr Gly Pro Ala Ser Ile
            100                 105                 110 aat ccg gcc acg ggc aag acc tat ggc ctg tcg ttc cca gtc atc acc     384
Asn Pro Ala Thr Gly Lys Thr Tyr Gly Leu Ser Phe Pro Val Ile Thr
        115                 120                 125 atc gcc gat atg gtg cgg gcc cag gcc atg ctg gtc tct gcg ctc ggg     432
Ile Ala Asp Met Val Arg Ala Gln Ala Met Leu Val Ser Ala Leu Gly
130                 135                 140 gtc gag acc ctg ttc gcc gtc gtc ggc ggc tcg atg ggc ggc atg cag     480
Val Glu Thr Leu Phe Ala Val Val Gly Gly Ser Met Gly Gly Met Gln
145                 150                 155                 160 gtc cag caa tgg gcc gtg gac tat ccc gag cgg atg ttc agc gcc gtg     528
Val Gln Gln Trp Ala Val Asp Tyr Pro Glu Arg Met Phe Ser Ala Val
                165                 170                 175 gtg ctg gcc tcg gcc tcg cgc cac tcg gcc cag aac atc gcg ttc cac     576
Val Leu Ala Ser Ala Ser Arg His Ser Ala Gln Asn Ile Ala Phe His
            180                 185                 190 gag gtg ggc cgc cag gcg atc atg gcc gat ccc gac tgg cgc ggc ggc     624
Glu Val Gly Arg Gln Ala Ile Met Ala Asp Pro Asp Trp Arg Gly Gly
        195                 200                 205 gcc tat gcc gag cac ggc gtg cgg ccc gag aag ggc ctg gcc gtg gcg     672
Ala Tyr Ala Glu His Gly Val Arg Pro Glu Lys Gly Leu Ala Val Ala
210                 215                 220 cgg atg gcc gcg cac atc acc tat ctg tcc gag ccc gcc ctg cag cgg     720
Arg Met Ala Ala His Ile Thr Tyr Leu Ser Glu Pro Ala Leu Gln Arg
225                 230                 235                 240 aag ttc ggc cgc gag cta cag cgc gac ggc ctc tcc tgg ggc ttt gac     768
Lys Phe Gly Arg Glu Leu Gln Arg Asp Gly Leu Ser Trp Gly Phe Asp
```

```
                        Lys Phe Gly Arg Glu Leu Gln Arg Asp Gly Leu Ser Trp Gly Phe Asp
                                        245                 250                 255 gcc gac ttc cag gtc gag agc tat cta cgc cag ggg tcc agc ttc                816
Ala Asp Phe Gln Val Glu Ser Tyr Leu Arg His Gln Gly Ser Ser Phe
            260                 265                 270 gtc gac cgg ttc gac gcc aac agc tat ctc tac atc acc cgg gcc atg            864
Val Asp Arg Phe Asp Ala Asn Ser Tyr Leu Tyr Ile Thr Arg Ala Met
        275                 280                 285 gac tat ttc gac atc gcc gcc agc cat ggc ggg gtg ctg gcc aag gcg            912
Asp Tyr Phe Asp Ile Ala Ala Ser His Gly Gly Val Leu Ala Lys Ala
    290                 295                 300 ttc acc cga gcg cgg aat gtg cgc ttc tgc gtg ctg agc ttc tcc agc            960
Phe Thr Arg Ala Arg Asn Val Arg Phe Cys Val Leu Ser Phe Ser Ser
305                 310                 315                 320 gac tgg ctc tat ccg acc gcc gag aac cgc cac ctg gtc cgc gcc ctg            1008
Asp Trp Leu Tyr Pro Thr Ala Glu Asn Arg His Leu Val Arg Ala Leu
                325                 330                 335 acc gcc gcc ggg gcc cgc gcg gcc ttc gcc gag atc gag agc gac aag            1056
Thr Ala Ala Gly Ala Arg Ala Ala Phe Ala Glu Ile Glu Ser Asp Lys
            340                 345                 350 ggc cat gac gcc ttc ctg ctg gac gag ccg gtg atg gac gcc gcg ctg            1104
Gly His Asp Ala Phe Leu Leu Asp Glu Pro Val Met Asp Ala Ala Leu
        355                 360                 365 gaa ggc ttc ctg gcc tcg gcc gaa cgc gat cgg ggg ctg gtt                    1146
Glu Gly Phe Leu Ala Ser Ala Glu Arg Asp Arg Gly Leu Val
    370                 375                 380 tga                                                                         1149

<210> SEQ ID NO 10
<211> LENGTH: 382
<212> TYPE: PRT
<213> ORGANISM: Caulobacter crescentus

<400> SEQUENCE: 10

Met Ala Ala Leu Asp Pro Ile Thr Pro Ala Gly Gly Thr Trp Arg
  1               5                  10                  15

Phe Pro Ala Asn Glu Pro Leu Arg Leu Asp Ser Gly Gly Val Ile Glu
                20                  25                  30

Gly Leu Glu Ile Ala Tyr Gln Thr Tyr Gly Gln Leu Asn Ala Asp Lys
            35                  40                  45

Ser Asn Ala Val Leu Ile Cys His Ala Leu Thr Gly Asp Gln His Val
        50                  55                  60

Ala Ser Pro His Pro Thr Thr Gly Lys Pro Gly Trp Trp Gln Arg Leu
    65                  70                  75                  80

Val Gly Pro Gly Lys Pro Leu Asp Pro Ala Arg His Phe Ile Ile Cys
                85                  90                  95

Ser Asn Val Ile Gly Gly Cys Met Gly Ser Thr Gly Pro Ala Ser Ile
                100                 105                 110

Asn Pro Ala Thr Gly Lys Thr Tyr Gly Leu Ser Phe Pro Val Ile Thr
            115                 120                 125

Ile Ala Asp Met Val Arg Ala Gln Ala Met Leu Val Ser Ala Leu Gly
        130                 135                 140

Val Glu Thr Leu Phe Ala Val Gly Gly Ser Met Gly Gly Met Gln
145                 150                 155                 160

Val Gln Gln Trp Ala Val Asp Tyr Pro Glu Arg Met Phe Ser Ala Val
                165                 170                 175

Val Leu Ala Ser Ala Ser Arg His Ser Ala Gln Asn Ile Ala Phe His
```

-continued

```
                    180                 185                 190
Glu Val Gly Arg Gln Ala Ile Met Ala Asp Pro Asp Trp Arg Gly Gly
                195                 200                 205

Ala Tyr Ala Glu His Gly Val Arg Pro Glu Lys Gly Leu Ala Val Ala
            210                 215                 220

Arg Met Ala Ala His Ile Thr Tyr Leu Ser Glu Pro Ala Leu Gln Arg
225                 230                 235                 240

Lys Phe Gly Arg Glu Leu Gln Arg Asp Gly Leu Ser Trp Gly Phe Asp
                245                 250                 255

Ala Asp Phe Gln Val Glu Ser Tyr Leu Arg His Gln Gly Ser Ser Phe
            260                 265                 270

Val Asp Arg Phe Asp Ala Asn Ser Tyr Leu Tyr Ile Thr Arg Ala Met
275                 280                 285

Asp Tyr Phe Asp Ile Ala Ala Ser His Gly Gly Val Leu Ala Lys Ala
            290                 295                 300

Phe Thr Arg Ala Arg Asn Val Arg Phe Cys Val Leu Ser Phe Ser Ser
305                 310                 315                 320

Asp Trp Leu Tyr Pro Thr Ala Glu Asn Arg His Leu Val Arg Ala Leu
                325                 330                 335

Thr Ala Gly Ala Arg Ala Ala Phe Ala Glu Ile Glu Ser Asp Lys
            340                 345                 350

Gly His Asp Ala Phe Leu Leu Asp Glu Pro Val Met Asp Ala Ala Leu
            355                 360                 365

Glu Gly Phe Leu Ala Ser Ala Glu Arg Asp Arg Gly Leu Val
        370                 375                 380

<210> SEQ ID NO 11
<211> LENGTH: 1140
<212> TYPE: DNA
<213> ORGANISM: Neisseria gonorrhoeae
<220> FEATURE:
<221> NAME/KEY: CDS
<222> LOCATION: (1)..(1137)
<223> OTHER INFORMATION: RNG00132

<400> SEQUENCE: 11 atg agt caa aat acc tcg gtg ggc att gta acg ccc caa aaa att ccg      48
Met Ser Gln Asn Thr Ser Val Gly Ile Val Thr Pro Gln Lys Ile Pro
 1               5                  10                  15 ttt gaa atg ccg ctg gtt ttg gaa aac ggt aaa act ttg ccg cgt ttc      96
Phe Glu Met Pro Leu Val Leu Glu Asn Gly Lys Thr Leu Pro Arg Phe
                20                  25                  30 gat ctg atg att gaa acc tac ggc gag ctg aat gct gaa aaa aac aat     144
Asp Leu Met Ile Glu Thr Tyr Gly Glu Leu Asn Ala Glu Lys Asn Asn
            35                  40                  45 gcg gtt tta atc tgc cac gcg ctg tcg ggc aac cat cac gtt gcg ggc     192
Ala Val Leu Ile Cys His Ala Leu Ser Gly Asn His His Val Ala Gly
        50                  55                  60 agg cat tcg gcg gag gat aaa tat acg ggc tgg tgg gac aat atg gtc     240
Arg His Ser Ala Glu Asp Lys Tyr Thr Gly Trp Trp Asp Asn Met Val
 65                  70                  75                  80 ggt ccc gga aaa ccg att gat acg gaa cgt ttt ttc gtg gtc ggg ttg     288
Gly Pro Gly Lys Pro Ile Asp Thr Glu Arg Phe Phe Val Val Gly Leu
                 85                  90                  95 aac aat ctg ggc ggc tgc gac ggc agc agc ggg cct ttg tcg atc aat     336
Asn Asn Leu Gly Gly Cys Asp Gly Ser Ser Gly Pro Leu Ser Ile Asn
                100                 105                 110 cct gaa acg ggc agg gaa tac ggc gcg gat ttt ccg atg gtt acg gtg     384
```

```
                                                     -continued

Pro Glu Thr Gly Arg Glu Tyr Gly Ala Asp Phe Pro Met Val Thr Val
        115                 120                 125 aag gac tgg gta aaa tca caa gcc gcg ctt gcc gat tat ctc ggc atc      432
Lys Asp Trp Val Lys Ser Gln Ala Ala Leu Ala Asp Tyr Leu Gly Ile
130                 135                 140 gaa caa tgg gcg gcg gtt gtc ggc ggc agc ttg ggc ggc atg cag gct      480
Glu Gln Trp Ala Ala Val Val Gly Gly Ser Leu Gly Gly Met Gln Ala
145                 150                 155                 160 ttg cag tgg gcg att tcc tat ccc gaa cgt gtg cgc cac gcc ttg gtg      528
Leu Gln Trp Ala Ile Ser Tyr Pro Glu Arg Val Arg His Ala Leu Val
                165                 170                 175 att gcg tct gcg ccg aaa ctg tcc gcg caa aat atc gcg ttt aat gat      576
Ile Ala Ser Ala Pro Lys Leu Ser Ala Gln Asn Ile Ala Phe Asn Asp
            180                 185                 190 gta gca cgt cag gcg att ttg acc gac ccc gat ttc aat gaa gga cat      624
Val Ala Arg Gln Ala Ile Leu Thr Asp Pro Asp Phe Asn Glu Gly His
        195                 200                 205 tac cgc agc cac aac acc gtt ccc gcg cgc ggt ttg cgg att gcc cgt      672
Tyr Arg Ser His Asn Thr Val Pro Ala Arg Gly Leu Arg Ile Ala Arg
    210                 215                 220 atg atg gga cac att acg tat ctt gcc gaa gac ggt ttg ggc aaa aaa      720
Met Met Gly His Ile Thr Tyr Leu Ala Glu Asp Gly Leu Gly Lys Lys
225                 230                 235                 240 ttc gga cgc gat ttg cgt tcc aac ggc tat caa tac ggc tat agc gtt      768
Phe Gly Arg Asp Leu Arg Ser Asn Gly Tyr Gln Tyr Gly Tyr Ser Val
                245                 250                 255 gaa ttt gaa gta gaa tcc tat ctc cgc tat caa ggc gac aaa ttc gtc      816
Glu Phe Glu Val Glu Ser Tyr Leu Arg Tyr Gln Gly Asp Lys Phe Val
            260                 265                 270 ggg cgg ttt gat gct aat aca tat ttg ctg atg acc aaa gct ttg gac      864
Gly Arg Phe Asp Ala Asn Thr Tyr Leu Leu Met Thr Lys Ala Leu Asp
        275                 280                 285 tat ttc gat ccg gcg gcg gat ttc ggc aac agc ctg acc cgc gcc gtg      912
Tyr Phe Asp Pro Ala Ala Asp Phe Gly Asn Ser Leu Thr Arg Ala Val
    290                 295                 300 cag gat gtg cag gca aaa ttc ttt gtc gcc agc ttc agc acc gac tgg      960
Gln Asp Val Gln Ala Lys Phe Phe Val Ala Ser Phe Ser Thr Asp Trp
305                 310                 315                 320 cgt ttc gcg ccc gaa cgt tcg cac gaa ctg gtc aag gca ctg att gcc     1008
Arg Phe Ala Pro Glu Arg Ser His Glu Leu Val Lys Ala Leu Ile Ala
                325                 330                 335 gcc caa aaa tcc gtg cag tat atc gaa gtc aag tcc gca cac ggg cac     1056
Ala Gln Lys Ser Val Gln Tyr Ile Glu Val Lys Ser Ala His Gly His
            340                 345                 350 gat gcc ttt tta atg gaa gac gaa gcc tat atg cgc gcc gta acg gct     1104
Asp Ala Phe Leu Met Glu Asp Glu Ala Tyr Met Arg Ala Val Thr Ala
        355                 360                 365 tat atg aac aat gtt gac aag gat tgc cga tta tga                     1140
Tyr Met Asn Asn Val Asp Lys Asp Cys Arg Leu
    370                 375

<210> SEQ ID NO 12
<211> LENGTH: 379
<212> TYPE: PRT
<213> ORGANISM: Neisseria gonorrhoeae

<400> SEQUENCE: 12

Met Ser Gln Asn Thr Ser Val Gly Ile Val Thr Pro Gln Lys Ile Pro
1               5                   10                  15

Phe Glu Met Pro Leu Val Leu Glu Asn Gly Lys Thr Leu Pro Arg Phe
```

```
                 20                  25                  30
Asp Leu Met Ile Glu Thr Tyr Gly Glu Leu Asn Ala Glu Lys Asn Asn
             35                  40                  45

Ala Val Leu Ile Cys His Ala Leu Ser Gly Asn His Val Ala Gly
     50                  55                  60

Arg His Ser Ala Glu Asp Lys Tyr Thr Gly Trp Trp Asp Asn Met Val
 65                  70                  75                  80

Gly Pro Gly Lys Pro Ile Asp Thr Glu Arg Phe Phe Val Val Gly Leu
                 85                  90                  95

Asn Asn Leu Gly Gly Cys Asp Gly Ser Ser Gly Pro Leu Ser Ile Asn
             100                 105                 110

Pro Glu Thr Gly Arg Glu Tyr Gly Ala Asp Phe Pro Met Val Thr Val
             115                 120                 125

Lys Asp Trp Val Lys Ser Gln Ala Ala Leu Ala Asp Tyr Leu Gly Ile
         130                 135                 140

Glu Gln Trp Ala Ala Val Val Gly Gly Ser Leu Gly Gly Met Gln Ala
145                 150                 155                 160

Leu Gln Trp Ala Ile Ser Tyr Pro Glu Arg Val Arg His Ala Leu Val
                 165                 170                 175

Ile Ala Ser Ala Pro Lys Leu Ser Ala Gln Asn Ile Ala Phe Asn Asp
             180                 185                 190

Val Ala Arg Gln Ala Ile Leu Thr Asp Pro Asp Phe Asn Glu Gly His
             195                 200                 205

Tyr Arg Ser His Asn Thr Val Pro Ala Arg Gly Leu Arg Ile Ala Arg
         210                 215                 220

Met Met Gly His Ile Thr Tyr Leu Ala Glu Asp Gly Leu Gly Lys Lys
225                 230                 235                 240

Phe Gly Arg Asp Leu Arg Ser Asn Gly Tyr Gln Tyr Gly Tyr Ser Val
                 245                 250                 255

Glu Phe Glu Val Glu Ser Tyr Leu Arg Tyr Gln Gly Asp Lys Phe Val
             260                 265                 270

Gly Arg Phe Asp Ala Asn Thr Tyr Leu Leu Met Thr Lys Ala Leu Asp
         275                 280                 285

Tyr Phe Asp Pro Ala Ala Asp Phe Gly Asn Ser Leu Thr Arg Ala Val
         290                 295                 300

Gln Asp Val Gln Ala Lys Phe Phe Val Ala Ser Phe Ser Thr Asp Trp
305                 310                 315                 320

Arg Phe Ala Pro Glu Arg Ser His Glu Leu Val Lys Ala Leu Ile Ala
                 325                 330                 335

Ala Gln Lys Ser Val Gln Tyr Ile Glu Val Lys Ser Ala His Gly His
             340                 345                 350

Asp Ala Phe Leu Met Glu Asp Glu Ala Tyr Met Arg Ala Val Thr Ala
         355                 360                 365

Tyr Met Asn Asn Val Asp Lys Asp Cys Arg Leu
     370                 375

<210> SEQ ID NO 13
<211> LENGTH: 1140
<212> TYPE: DNA
<213> ORGANISM: Neisseria meningitidis ser. A
<220> FEATURE:
<221> NAME/KEY: CDS
<222> LOCATION: (1)..(1137)
<223> OTHER INFORMATION: RNM00815

<400> SEQUENCE: 13
```

```
atg agt caa aat gcc tcg gtg ggc att gta acg ccc caa aaa att ccg      48
Met Ser Gln Asn Ala Ser Val Gly Ile Val Thr Pro Gln Lys Ile Pro
 1               5                  10                  15 ttt gaa atg ccg ctg gtt ttg gaa aac ggt aaa act ttg ccg cgt ttc      96
Phe Glu Met Pro Leu Val Leu Glu Asn Gly Lys Thr Leu Pro Arg Phe
                20                  25                  30 gat ctg atg att gaa acc tac ggc gag ctg aat gcc gaa aaa aat aat     144
Asp Leu Met Ile Glu Thr Tyr Gly Glu Leu Asn Ala Glu Lys Asn Asn
             35                  40                  45 gcg gtt tta atc tgt cat gcg ctg tca ggc aac cat cat gtt gcg ggc     192
Ala Val Leu Ile Cys His Ala Leu Ser Gly Asn His His Val Ala Gly
 50                  55                  60 agg cat tcg gcg gag gat aaa tat acg ggc tgg tgg gac aat atg gta     240
Arg His Ser Ala Glu Asp Lys Tyr Thr Gly Trp Trp Asp Asn Met Val
 65                  70                  75                  80 gga ccc ggc aaa ccg att gat aca gaa cgt ttt ttc gtg gtc ggt ttg     288
Gly Pro Gly Lys Pro Ile Asp Thr Glu Arg Phe Phe Val Val Gly Leu
                 85                  90                  95 aac aat ctg ggc ggc tgc gac ggc agc agc gga cct ttg tcg atc aat     336
Asn Asn Leu Gly Gly Cys Asp Gly Ser Ser Gly Pro Leu Ser Ile Asn
                100                 105                 110 cct gaa acg ggc agg gaa tac ggc gcg gat ttt ccg gtg gtt acg gtg     384
Pro Glu Thr Gly Arg Glu Tyr Gly Ala Asp Phe Pro Val Val Thr Val
            115                 120                 125 aag gac tgg gta aaa tcc caa gcc gcg ctt acc gat tat ctc ggc atc     432
Lys Asp Trp Val Lys Ser Gln Ala Ala Leu Thr Asp Tyr Leu Gly Ile
130                 135                 140 ggg caa tgg gcg gcg gtt gtc ggc ggc agc ttg ggc ggt atg cag gct     480
Gly Gln Trp Ala Ala Val Val Gly Gly Ser Leu Gly Gly Met Gln Ala
145                 150                 155                 160 ttg cag tgg acg att tcc tat ccc gag cgc gtg cgc cat gcc tta gtg     528
Leu Gln Trp Thr Ile Ser Tyr Pro Glu Arg Val Arg His Ala Leu Val
                165                 170                 175 att gcg tcc gcg ccg aaa ctg tcc acg caa aat atc gcg ttt aat gat     576
Ile Ala Ser Ala Pro Lys Leu Ser Thr Gln Asn Ile Ala Phe Asn Asp
            180                 185                 190 gta gca cgt cag gcg att ttg acc gat ccc gat ttc aac gaa gga cat     624
Val Ala Arg Gln Ala Ile Leu Thr Asp Pro Asp Phe Asn Glu Gly His
        195                 200                 205 tac cgc agc cgc aac acc gtt ccc gct cgg ggc ttg cgg att gcc cgc     672
Tyr Arg Ser Arg Asn Thr Val Pro Ala Arg Gly Leu Arg Ile Ala Arg
    210                 215                 220 atg atg ggg cac atc acc tat ctt gcc gaa gac ggt ttg ggc aaa aaa     720
Met Met Gly His Ile Thr Tyr Leu Ala Glu Asp Gly Leu Gly Lys Lys
225                 230                 235                 240 ttc gga cgc gat ttg cgt tcc aac ggc tat caa tac ggc tat ggc gtt     768
Phe Gly Arg Asp Leu Arg Ser Asn Gly Tyr Gln Tyr Gly Tyr Gly Val
                245                 250                 255 gaa ttt gaa gta gaa tcc tat ctg cgc tat caa ggc gat aaa ttc gtc     816
Glu Phe Glu Val Glu Ser Tyr Leu Arg Tyr Gln Gly Asp Lys Phe Val
                260                 265                 270 ggg cgg ttt gat gcc aac acc tat ttg ctg atg acc aag gct ttg gac     864
Gly Arg Phe Asp Ala Asn Thr Tyr Leu Leu Met Thr Lys Ala Leu Asp
            275                 280                 285 tat ttc gat ccg gcg gcg gat ttc ggc aac agc ctg acc cgc gcc gtg     912
Tyr Phe Asp Pro Ala Ala Asp Phe Gly Asn Ser Leu Thr Arg Ala Val
        290                 295                 300 cag gat gtt cag gca aaa ttc ttt gtc gcc agc ttc agc acc gat tgg     960
Gln Asp Val Gln Ala Lys Phe Phe Val Ala Ser Phe Ser Thr Asp Trp
```

```
                305                 310                 315                 320
cgt ttc gcg ccc gaa cgt tcg cac gaa ctg gtc aag gcc ctg att gcc    1008
Arg Phe Ala Pro Glu Arg Ser His Glu Leu Val Lys Ala Leu Ile Ala
                325                 330                 335 gcc caa aaa tcc gtg cag tat atc gaa gtc aaa tcc gca cac ggg cac    1056
Ala Gln Lys Ser Val Gln Tyr Ile Glu Val Lys Ser Ala His Gly His
            340                 345                 350 gat gcc ttt tta atg gaa gac gaa gcc tat atg cgt gcg gtc gcc gcc    1104
Asp Ala Phe Leu Met Glu Asp Glu Ala Tyr Met Arg Ala Val Ala Ala
        355                 360                 365 tat atg aac aac gtt tat aag gaa tgt cag caa tga                    1140
Tyr Met Asn Asn Val Tyr Lys Glu Cys Gln Gln
    370                 375

<210> SEQ ID NO 14
<211> LENGTH: 379
<212> TYPE: PRT
<213> ORGANISM: Neisseria meningitidis ser. A

<400> SEQUENCE: 14

Met Ser Gln Asn Ala Ser Val Gly Ile Val Thr Pro Gln Lys Ile Pro
1               5                   10                  15

Phe Glu Met Pro Leu Val Leu Glu Asn Gly Lys Thr Leu Pro Arg Phe
                20                  25                  30

Asp Leu Met Ile Glu Thr Tyr Gly Glu Leu Asn Ala Glu Lys Asn Asn
            35                  40                  45

Ala Val Leu Ile Cys His Ala Leu Ser Gly Asn His Val Ala Gly
        50                  55                  60

Arg His Ser Ala Glu Asp Lys Tyr Thr Gly Trp Trp Asp Asn Met Val
65                  70                  75                  80

Gly Pro Gly Lys Pro Ile Asp Thr Glu Arg Phe Phe Val Val Gly Leu
                85                  90                  95

Asn Asn Leu Gly Gly Cys Asp Gly Ser Ser Gly Pro Leu Ser Ile Asn
                100                 105                 110

Pro Glu Thr Gly Arg Glu Tyr Gly Ala Asp Phe Pro Val Val Thr Val
            115                 120                 125

Lys Asp Trp Val Lys Ser Gln Ala Ala Leu Thr Asp Tyr Leu Gly Ile
130                 135                 140

Gly Gln Trp Ala Ala Val Val Gly Gly Ser Leu Gly Gly Met Gln Ala
145                 150                 155                 160

Leu Gln Trp Thr Ile Ser Tyr Pro Glu Arg Val Arg His Ala Leu Val
                165                 170                 175

Ile Ala Ser Ala Pro Lys Leu Ser Thr Gln Asn Ile Ala Phe Asn Asp
            180                 185                 190

Val Ala Arg Gln Ala Ile Leu Thr Asp Pro Asp Phe Asn Glu Gly His
        195                 200                 205

Tyr Arg Ser Arg Asn Thr Val Pro Ala Arg Gly Leu Arg Ile Ala Arg
    210                 215                 220

Met Met Gly His Ile Thr Tyr Leu Ala Glu Asp Gly Leu Gly Lys Lys
225                 230                 235                 240

Phe Gly Arg Asp Leu Arg Ser Asn Gly Tyr Gln Tyr Gly Tyr Gly Val
                245                 250                 255

Glu Phe Glu Val Glu Ser Tyr Leu Arg Tyr Gln Gly Asp Lys Phe Val
            260                 265                 270

Gly Arg Phe Asp Ala Asn Thr Tyr Leu Leu Met Thr Lys Ala Leu Asp
        275                 280                 285
```

```
Tyr Phe Asp Pro Ala Ala Asp Phe Gly Asn Ser Leu Thr Arg Ala Val
    290                 295                 300

Gln Asp Val Gln Ala Lys Phe Phe Val Ala Ser Phe Ser Thr Asp Trp
305                 310                 315                 320

Arg Phe Ala Pro Glu Arg Ser His Glu Leu Val Lys Ala Leu Ile Ala
                325                 330                 335

Ala Gln Lys Ser Val Gln Tyr Ile Glu Val Lys Ser Ala His Gly His
                340                 345                 350

Asp Ala Phe Leu Met Glu Asp Glu Ala Tyr Met Arg Ala Val Ala Ala
            355                 360                 365

Tyr Met Asn Asn Val Tyr Lys Glu Cys Gln Gln
        370                 375

<210> SEQ ID NO 15
<211> LENGTH: 1140
<212> TYPE: DNA
<213> ORGANISM: Pseudomonas fluorescens
<220> FEATURE:
<221> NAME/KEY: CDS
<222> LOCATION: (1)..(1137)
<223> OTHER INFORMATION: RPU01633

<400> SEQUENCE: 15
```

| | | |
|---|---|---|
| atg cca gct gcc ttt ccc ccc gat tct gtt ggt ctg gtg acg ccg caa | 48 | |
| Met Pro Ala Ala Phe Pro Pro Asp Ser Val Gly Leu Val Thr Pro Gln | | |
| 1               5                  10                  15 | | |
| acg gcg cac ttc agc gaa ccg ctg gcc ctg gcc tgc ggc cgt tcg ctg | 96 | |
| Thr Ala His Phe Ser Glu Pro Leu Ala Leu Ala Cys Gly Arg Ser Leu | | |
|                 20                  25                  30 | | |
| gcc gat tat gac ctg atc tac gaa acc tac ggc acg ctg aac gcg caa | 144 | |
| Ala Asp Tyr Asp Leu Ile Tyr Glu Thr Tyr Gly Thr Leu Asn Ala Gln | | |
|         35                  40                  45 | | |
| gcg agc aac gcc gtg ctg atc tgc cac gcc ttg tcc ggc cac cac cat | 192 | |
| Ala Ser Asn Ala Val Leu Ile Cys His Ala Leu Ser Gly His His His | | |
| 50                  55                  60 | | |
| gct gcg ggt tat cac agc gtc gac gac cgc aag ccc ggt tgg tgg gac | 240 | |
| Ala Ala Gly Tyr His Ser Val Asp Asp Arg Lys Pro Gly Trp Trp Asp | | |
| 65                  70                  75                  80 | | |
| agc tgc atc ggc ccc ggc aaa ccg atc gac acc aac aag ttc ttc gtg | 288 | |
| Ser Cys Ile Gly Pro Gly Lys Pro Ile Asp Thr Asn Lys Phe Phe Val | | |
|                 85                  90                  95 | | |
| gtc agc ctg aac aac ctc ggc ggt tgc aat ggt tct acc ggc ccg agc | 336 | |
| Val Ser Leu Asn Asn Leu Gly Gly Cys Asn Gly Ser Thr Gly Pro Ser | | |
|                 100                 105                 110 | | |
| agc ctc aat ccg gaa acc ggc aag ccg ttc ggc gcc gac ttc ccg gtg | 384 | |
| Ser Leu Asn Pro Glu Thr Gly Lys Pro Phe Gly Ala Asp Phe Pro Val | | |
|         115                 120                 125 | | |
| ctg acc gtg gaa gac tgg gtg cac agc cag gca cgc ctg gcc gac ctg | 432 | |
| Leu Thr Val Glu Asp Trp Val His Ser Gln Ala Arg Leu Ala Asp Leu | | |
| 130                 135                 140 | | |
| ctc ggc atc ggc cag tgg gcg gcg gtg atc ggc ggc agc ctg ggc ggc | 480 | |
| Leu Gly Ile Gly Gln Trp Ala Ala Val Ile Gly Gly Ser Leu Gly Gly | | |
| 145                 150                 155                 160 | | |
| atg cag gcg ctg caa tgg acc atc acc tat ccg gat cgc gtt cgc cac | 528 | |
| Met Gln Ala Leu Gln Trp Thr Ile Thr Tyr Pro Asp Arg Val Arg His | | |
|                 165                 170                 175 | | |
| tgc ctg gcc atc gcc tcg gcc ccc aag ctg tcg gcg cag aac atc gcc | 576 | |
| Cys Leu Ala Ile Ala Ser Ala Pro Lys Leu Ser Ala Gln Asn Ile Ala | | |
|                 180                 185                 190 | | |

-continued

```
ttc aac gaa gtg gcg cgc cag gcg atc ctc act gac ccg gaa ttc cac    624
Phe Asn Glu Val Ala Arg Gln Ala Ile Leu Thr Asp Pro Glu Phe His
        195                 200                 205 ggc ggc tcg ttc cag gaa cac ggc gtg atc ccc aag cgc ggc ctg atg    672
Gly Gly Ser Phe Gln Glu His Gly Val Ile Pro Lys Arg Gly Leu Met
    210                 215                 220 ctg gcg cgg atg gtg ggg cac atc acc tac ctg tcc gac gac tcc atg    720
Leu Ala Arg Met Val Gly His Ile Thr Tyr Leu Ser Asp Asp Ser Met
225                 230                 235                 240 ggt gag aaa ttc ggc cgt ggc ctg aag agc gaa aag ctc aac tac gac    768
Gly Glu Lys Phe Gly Arg Gly Leu Lys Ser Glu Lys Leu Asn Tyr Asp
                245                 250                 255 ttc cac agc gtc gag ttc cag gtc gaa agc tac ctg cgc tat cag ggc    816
Phe His Ser Val Glu Phe Gln Val Glu Ser Tyr Leu Arg Tyr Gln Gly
            260                 265                 270 gaa gag ttc tcc ggg cgc ttc gat gcc aac acc tat ctg ttg atg acc    864
Glu Glu Phe Ser Gly Arg Phe Asp Ala Asn Thr Tyr Leu Leu Met Thr
        275                 280                 285 aag gcg ctg gac tac ttc gat ccg gcg gcg aac ttc aac gat aac ctg    912
Lys Ala Leu Asp Tyr Phe Asp Pro Ala Ala Asn Phe Asn Asp Asn Leu
    290                 295                 300 gcg aaa acc ttc gaa ggt gca aaa gcc aag ttc tgc gtg atg tcg ttc    960
Ala Lys Thr Phe Glu Gly Ala Lys Ala Lys Phe Cys Val Met Ser Phe
305                 310                 315                 320 acc acc gac tgg cgc ttc tcc ccg gcc cgc tcg cga gaa ctg gtg gat   1008
Thr Thr Asp Trp Arg Phe Ser Pro Ala Arg Ser Arg Glu Leu Val Asp
                325                 330                 335 gcg ctg atg gcg gcg cgc aaa gac gtc agc tac ctg gaa atc gac gcg   1056
Ala Leu Met Ala Ala Arg Lys Asp Val Ser Tyr Leu Glu Ile Asp Ala
            340                 345                 350 ccc cag ggc cac gac gcc ttc ctg att ccg atc ccg cgc tac ttg cag   1104
Pro Gln Gly His Asp Ala Phe Leu Ile Pro Ile Pro Arg Tyr Leu Gln
        355                 360                 365 gcg ttc ggc aat tac atg aac cgc att acg ttg tga                   1140
Ala Phe Gly Asn Tyr Met Asn Arg Ile Thr Leu
    370                 375
```

<210> SEQ ID NO 16
<211> LENGTH: 379
<212> TYPE: PRT
<213> ORGANISM: Pseudomonas fluorescens

<400> SEQUENCE: 16

```
Met Pro Ala Ala Phe Pro Pro Asp Ser Val Gly Leu Val Thr Pro Gln
  1               5                  10                  15

Thr Ala His Phe Ser Glu Pro Leu Ala Leu Ala Cys Gly Arg Ser Leu
             20                  25                  30

Ala Asp Tyr Asp Leu Ile Tyr Glu Thr Tyr Gly Thr Leu Asn Ala Gln
         35                  40                  45

Ala Ser Asn Ala Val Leu Ile Cys His Ala Leu Ser Gly His His His
     50                  55                  60

Ala Ala Gly Tyr His Ser Val Asp Asp Arg Lys Pro Gly Trp Trp Asp
 65                  70                  75                  80

Ser Cys Ile Gly Pro Gly Lys Pro Ile Asp Thr Asn Lys Phe Phe Val
                 85                  90                  95

Val Ser Leu Asn Asn Leu Gly Gly Cys Asn Gly Ser Thr Gly Pro Ser
            100                 105                 110

Ser Leu Asn Pro Glu Thr Gly Lys Pro Phe Gly Ala Asp Phe Pro Val
        115                 120                 125
```

```
Leu Thr Val Glu Asp Trp Val His Ser Gln Ala Arg Leu Ala Asp Leu
            130                 135                 140

Leu Gly Ile Gly Gln Trp Ala Ala Val Ile Gly Gly Ser Leu Gly Gly
145                 150                 155                 160

Met Gln Ala Leu Gln Trp Thr Ile Thr Tyr Pro Asp Arg Val Arg His
                165                 170                 175

Cys Leu Ala Ile Ala Ser Ala Pro Lys Leu Ser Ala Gln Asn Ile Ala
            180                 185                 190

Phe Asn Glu Val Ala Arg Gln Ala Ile Leu Thr Asp Pro Glu Phe His
        195                 200                 205

Gly Gly Ser Phe Gln Glu His Gly Val Ile Pro Lys Arg Gly Leu Met
    210                 215                 220

Leu Ala Arg Met Val Gly His Ile Thr Tyr Leu Ser Asp Asp Ser Met
225                 230                 235                 240

Gly Glu Lys Phe Gly Arg Gly Leu Lys Ser Glu Lys Leu Asn Tyr Asp
                245                 250                 255

Phe His Ser Val Glu Phe Gln Val Glu Ser Tyr Leu Arg Tyr Gln Gly
            260                 265                 270

Glu Glu Phe Ser Gly Arg Phe Asp Ala Asn Thr Tyr Leu Leu Met Thr
        275                 280                 285

Lys Ala Leu Asp Tyr Phe Asp Pro Ala Ala Asn Phe Asn Asp Asn Leu
    290                 295                 300

Ala Lys Thr Phe Glu Gly Ala Lys Ala Lys Phe Cys Val Met Ser Phe
305                 310                 315                 320

Thr Thr Asp Trp Arg Phe Ser Pro Ala Arg Ser Arg Glu Leu Val Asp
                325                 330                 335

Ala Leu Met Ala Ala Arg Lys Asp Val Ser Tyr Leu Glu Ile Asp Ala
            340                 345                 350

Pro Gln Gly His Asp Ala Phe Leu Ile Pro Ile Pro Arg Tyr Leu Gln
        355                 360                 365

Ala Phe Gly Asn Tyr Met Asn Arg Ile Thr Leu
    370                 375

<210> SEQ ID NO 17
<211> LENGTH: 1140
<212> TYPE: DNA
<213> ORGANISM: Pseudomonas aeruginosa
<220> FEATURE:
<221> NAME/KEY: CDS
<222> LOCATION: (1)..(1137)
<223> OTHER INFORMATION: RPA04460

<400> SEQUENCE: 17 atg ccc aca gtc ttc ccc gac gac tcc gtc ggt ctg gtc tcc ccc cag      48
Met Pro Thr Val Phe Pro Asp Asp Ser Val Gly Leu Val Ser Pro Gln
 1               5                  10                  15 acg ctg cac ttc aac gaa ccg ctc gag ctg acc agc ggc aag tcc ctg      96
Thr Leu His Phe Asn Glu Pro Leu Glu Leu Thr Ser Gly Lys Ser Leu
                20                  25                  30 gcc gag tac gac ctg gtg atc gaa acc tac ggc gag ctg aat gcc acg     144
Ala Glu Tyr Asp Leu Val Ile Glu Thr Tyr Gly Glu Leu Asn Ala Thr
            35                  40                  45 cag agc aac gcg gtg ctg atc tgc cac gcc ctc tcc ggc cac cac cac     192
Gln Ser Asn Ala Val Leu Ile Cys His Ala Leu Ser Gly His His His
        50                  55                  60 gcc gcc ggc tac cac agc gtc gac gag cgc aag ccg ggc tgg tgg gac     240
Ala Ala Gly Tyr His Ser Val Asp Glu Arg Lys Pro Gly Trp Trp Asp
```

```
                65                  70                  75                  80
agc tgc atc ggt ccg ggc aag ccg atc gac acc cgc aag ttc ttc gtc         288
Ser Cys Ile Gly Pro Gly Lys Pro Ile Asp Thr Arg Lys Phe Phe Val
                        85                  90                  95 gtc gcc ctc aac aac ctc ggc ggt tgc aac gga tcc agc ggc ccc gcc         336
Val Ala Leu Asn Asn Leu Gly Gly Cys Asn Gly Ser Ser Gly Pro Ala
                100                 105                 110 agc atc aat ccg gcg acc ggc aag gtc tac ggc gcg gac ttc ccg atg         384
Ser Ile Asn Pro Ala Thr Gly Lys Val Tyr Gly Ala Asp Phe Pro Met
            115                 120                 125 gtt acg gtg gaa gac tgg gtg cat agc cag gcg cgc ctg gca gac cgc         432
Val Thr Val Glu Asp Trp Val His Ser Gln Ala Arg Leu Ala Asp Arg
        130                 135                 140 ctc ggc atc cgc cag tgg gcc gcg gtg gtc ggc ggc agc ctc ggc ggc         480
Leu Gly Ile Arg Gln Trp Ala Ala Val Val Gly Gly Ser Leu Gly Gly
145                 150                 155                 160 atg cag gcg ctg caa tgg acc atc agc tat ccc gag cgc gtc cgt cac         528
Met Gln Ala Leu Gln Trp Thr Ile Ser Tyr Pro Glu Arg Val Arg His
                165                 170                 175 tgc ctg tgc atc gcc agc gcg ccg aag ctg tcg gcg cag aac atc gcc         576
Cys Leu Cys Ile Ala Ser Ala Pro Lys Leu Ser Ala Gln Asn Ile Ala
                180                 185                 190 ttc aac gaa gtc gcc cgg cag gcg att ctt tcc gac cct gag ttc ctc         624
Phe Asn Glu Val Ala Arg Gln Ala Ile Leu Ser Asp Pro Glu Phe Leu
            195                 200                 205 ggc ggc tac ttc cag gag cag ggc gtg att ccc aag cgc ggc ctc aag         672
Gly Gly Tyr Phe Gln Glu Gln Gly Val Ile Pro Lys Arg Gly Leu Lys
        210                 215                 220 ctg gcg cgg atg gtc ggc cat atc acc tac ctg tcc gac gac gcc atg         720
Leu Ala Arg Met Val Gly His Ile Thr Tyr Leu Ser Asp Asp Ala Met
225                 230                 235                 240 ggc gcc aag ttc ggc cgt gta ctg aag acc gag aag ctc aac tac gac         768
Gly Ala Lys Phe Gly Arg Val Leu Lys Thr Glu Lys Leu Asn Tyr Asp
                245                 250                 255 ctg cac agc gtc gag ttc cag gtc gag agt tac ctg cgc tac cag ggc         816
Leu His Ser Val Glu Phe Gln Val Glu Ser Tyr Leu Arg Tyr Gln Gly
                260                 265                 270 gag gag ttc tcc acc cgc ttc gac gcc aat acc tac ctg ctg atg acc         864
Glu Glu Phe Ser Thr Arg Phe Asp Ala Asn Thr Tyr Leu Leu Met Thr
            275                 280                 285 aag gcg ctg gac tac ttc gac ccc gcc gcc gcc cac ggc gac gac ctg         912
Lys Ala Leu Asp Tyr Phe Asp Pro Ala Ala Ala His Gly Asp Asp Leu
        290                 295                 300 gtg cgc acc ctg gag ggc gtc gag gcg gac ttc tgc ctg atg tcc ttc         960
Val Arg Thr Leu Glu Gly Val Glu Ala Asp Phe Cys Leu Met Ser Phe
305                 310                 315                 320 acc acc gac tgg cgt ttc tcg ccg gcc cgc tcg cgg gaa atc gtc gac        1008
Thr Thr Asp Trp Arg Phe Ser Pro Ala Arg Ser Arg Glu Ile Val Asp
                325                 330                 335 gcc ctg atc gcg gcg aaa aag aac gtc agc tac ctg gag atc gac gcc        1056
Ala Leu Ile Ala Ala Lys Lys Asn Val Ser Tyr Leu Glu Ile Asp Ala
                340                 345                 350 ccg caa ggc cac gac gcc ttc ctc atg ccg atc ccc cgg tac ctg caa        1104
Pro Gln Gly His Asp Ala Phe Leu Met Pro Ile Pro Arg Tyr Leu Gln
            355                 360                 365 gcc ttc agc ggt tac atg aac cgc atc agc gtg tga                        1140
Ala Phe Ser Gly Tyr Met Asn Arg Ile Ser Val
        370                 375
```

<210> SEQ ID NO 18
<211> LENGTH: 379
<212> TYPE: PRT
<213> ORGANISM: Pseudomonas aeruginosa

<400> SEQUENCE: 18

| Met | Pro | Thr | Val | Phe | Pro | Asp | Asp | Ser | Val | Gly | Leu | Val | Ser | Pro | Gln |
|---|---|---|---|---|---|---|---|---|---|---|---|---|---|---|---|
| 1 | | | | 5 | | | | | 10 | | | | | 15 | |

Thr Leu His Phe Asn Glu Pro Leu Glu Leu Thr Ser Gly Lys Ser Leu
            20                  25                  30

Ala Glu Tyr Asp Leu Val Ile Glu Thr Tyr Gly Glu Leu Asn Ala Thr
        35                  40                  45

Gln Ser Asn Ala Val Leu Ile Cys His Ala Leu Ser Gly His His His
    50                  55                  60

Ala Ala Gly Tyr His Ser Val Asp Glu Arg Lys Pro Gly Trp Trp Asp
65                  70                  75                  80

Ser Cys Ile Gly Pro Gly Lys Pro Ile Asp Thr Arg Lys Phe Phe Val
                85                  90                  95

Val Ala Leu Asn Asn Leu Gly Gly Cys Asn Gly Ser Ser Gly Pro Ala
            100                 105                 110

Ser Ile Asn Pro Ala Thr Gly Lys Val Tyr Gly Ala Asp Phe Pro Met
        115                 120                 125

Val Thr Val Glu Asp Trp Val His Ser Gln Ala Arg Leu Ala Asp Arg
    130                 135                 140

Leu Gly Ile Arg Gln Trp Ala Ala Val Gly Gly Ser Leu Gly Gly Gly
145                 150                 155                 160

Met Gln Ala Leu Gln Trp Thr Ile Ser Tyr Pro Glu Arg Val Arg His
                165                 170                 175

Cys Leu Cys Ile Ala Ser Ala Pro Lys Leu Ser Ala Gln Asn Ile Ala
            180                 185                 190

Phe Asn Glu Val Ala Arg Gln Ala Ile Leu Ser Asp Pro Glu Phe Leu
        195                 200                 205

Gly Gly Tyr Phe Gln Glu Gln Gly Val Ile Pro Lys Arg Gly Leu Lys
    210                 215                 220

Leu Ala Arg Met Val Gly His Ile Thr Tyr Leu Ser Asp Asp Ala Met
225                 230                 235                 240

Gly Ala Lys Phe Gly Arg Val Leu Lys Thr Glu Lys Leu Asn Tyr Asp
                245                 250                 255

Leu His Ser Val Glu Phe Gln Val Glu Ser Tyr Leu Arg Tyr Gln Gly
            260                 265                 270

Glu Glu Phe Ser Thr Arg Phe Asp Ala Asn Thr Tyr Leu Leu Met Thr
        275                 280                 285

Lys Ala Leu Asp Tyr Phe Asp Pro Ala Ala Ala His Gly Asp Asp Leu
    290                 295                 300

Val Arg Thr Leu Glu Gly Val Glu Ala Asp Phe Cys Leu Met Ser Phe
305                 310                 315                 320

Thr Thr Asp Trp Arg Phe Ser Pro Ala Arg Ser Arg Glu Ile Val Asp
                325                 330                 335

Ala Leu Ile Ala Ala Lys Lys Asn Val Ser Tyr Leu Glu Ile Asp Ala
            340                 345                 350

Pro Gln Gly His Asp Ala Phe Leu Met Pro Ile Pro Arg Tyr Leu Gln
        355                 360                 365

Ala Phe Ser Gly Tyr Met Asn Arg Ile Ser Val
    370                 375

-continued

```
<210> SEQ ID NO 19
<211> LENGTH: 1146
<212> TYPE: DNA
<213> ORGANISM: Burkholderia cepacia
<220> FEATURE:
<221> NAME/KEY: CDS
<222> LOCATION: (1)..(1143)
<223> OTHER INFORMATION: RBU12675

<400> SEQUENCE: 19 atg gaa tcg atc ggt atc gtc gct ccc caa aaa atg cat ttc acc gag       48
Met Glu Ser Ile Gly Ile Val Ala Pro Gln Lys Met His Phe Thr Glu
 1               5                  10                  15 ccg ctg ccg ttg cag aac ggc agt tcg ctc gcc ggt tac gac ctg atg       96
Pro Leu Pro Leu Gln Asn Gly Ser Ser Leu Ala Gly Tyr Asp Leu Met
             20                  25                  30 gtc gag acc tac ggc acg ctc aac gcc gcg cgt agc aac gcg gtg ctg      144
Val Glu Thr Tyr Gly Thr Leu Asn Ala Ala Arg Ser Asn Ala Val Leu
         35                  40                  45 gtg tgc cac gcg ctc aac gcg tcg cac cac gtg gcg ggc gtg tat gcc      192
Val Cys His Ala Leu Asn Ala Ser His His Val Ala Gly Val Tyr Ala
     50                  55                  60 gac aac ccc agg gac atc ggc tgg tgg gac aac atg gtc ggc ccg ggc      240
Asp Asn Pro Arg Asp Ile Gly Trp Trp Asp Asn Met Val Gly Pro Gly
 65                  70                  75                  80 aag ccg ctc gac act gac aag ttc ttc gtg atc ggc gtg aac aac ctc      288
Lys Pro Leu Asp Thr Asp Lys Phe Phe Val Ile Gly Val Asn Asn Leu
                 85                  90                  95 gga tcg tgc ttc ggc tcg act ggg ccg atg agc atc gat ccg tct acc      336
Gly Ser Cys Phe Gly Ser Thr Gly Pro Met Ser Ile Asp Pro Ser Thr
            100                 105                 110 ggc aat ccg tac ggc gcg acg ttt ccc gtc gtg acg gtg gaa gac tgg      384
Gly Asn Pro Tyr Gly Ala Thr Phe Pro Val Val Thr Val Glu Asp Trp
        115                 120                 125 gtc aac gcc cag gcg cgc gtc gcg gat caa ttc ggc atc acg cgc ttt      432
Val Asn Ala Gln Ala Arg Val Ala Asp Gln Phe Gly Ile Thr Arg Phe
    130                 135                 140 gcg gcg gtg atg ggc ggc agc ctc ggc ggc atg cag gcg ctc gcg tgg      480
Ala Ala Val Met Gly Gly Ser Leu Gly Gly Met Gln Ala Leu Ala Trp
145                 150                 155                 160 agc atg atg tat ccg gag cgc gtc gct cac tgc atc gtg gtc gcg tcc      528
Ser Met Met Tyr Pro Glu Arg Val Ala His Cys Ile Val Val Ala Ser
                165                 170                 175 aca ccc aag ctg tcg gcg cag aac atc gcg ttc aac gag gtt gcg cgc      576
Thr Pro Lys Leu Ser Ala Gln Asn Ile Ala Phe Asn Glu Val Ala Arg
            180                 185                 190 tcg gcg atc ctg tcg gac ccg gac ttc cac ggc ggc aac tac tac gcg      624
Ser Ala Ile Leu Ser Asp Pro Asp Phe His Gly Gly Asn Tyr Tyr Ala
        195                 200                 205 cac aac gtt aag ccg aag cgc ggc ctg cgc gtc gcg cgc atg atc ggc      672
His Asn Val Lys Pro Lys Arg Gly Leu Arg Val Ala Arg Met Ile Gly
    210                 215                 220 cac atc acg tat ctg tcg gac gac gac atg gcc gag aaa ttc ggc cgc      720
His Ile Thr Tyr Leu Ser Asp Asp Asp Met Ala Glu Lys Phe Gly Arg
225                 230                 235                 240 tcg ctg cgg cgc gcg gaa ggc gcg ctg gac gcg tac aac ttc aac ttc      768
Ser Leu Arg Arg Ala Glu Gly Ala Leu Asp Ala Tyr Asn Phe Asn Phe
                245                 250                 255 gac gtg gag ttc gag gtg gag tcg tac ctg cgc tac cag ggc gac aag      816
Asp Val Glu Phe Glu Val Glu Ser Tyr Leu Arg Tyr Gln Gly Asp Lys
            260                 265                 270
```

```
ttc gcc gac tac ttc gac gcg aat acg tat ctg ctg atc acc cgc gcg       864
Phe Ala Asp Tyr Phe Asp Ala Asn Thr Tyr Leu Leu Ile Thr Arg Ala
        275                 280                 285 ctc gac tac ttc gat ccg gcc aag gcc ttc gcc ggc gac ctg acg gcc       912
Leu Asp Tyr Phe Asp Pro Ala Lys Ala Phe Ala Gly Asp Leu Thr Ala
        290                 295                 300 gcg gtc gcg cac acc acg gcg aaa tat ctg atc gcc agc ttc acg acc       960
Ala Val Ala His Thr Thr Ala Lys Tyr Leu Ile Ala Ser Phe Thr Thr
305                 310                 315                 320 gac tgg cgc ttc gcg ccg gcc cgc tcg cgt gaa ctg gtg aag gcg ctg      1008
Asp Trp Arg Phe Ala Pro Ala Arg Ser Arg Glu Leu Val Lys Ala Leu
                325                 330                 335 ctc gat cac aag cgc acg gtc acc tac gcg gaa atc gac gcg ccg cac      1056
Leu Asp His Lys Arg Thr Val Thr Tyr Ala Glu Ile Asp Ala Pro His
                340                 345                 350 ggc cac gac gcc ttc ctg ctc gac gac gcg cgc tat cac aac ctg atg      1104
Gly His Asp Ala Phe Leu Leu Asp Asp Ala Arg Tyr His Asn Leu Met
                355                 360                 365 cgc gct tac tac gaa cgt att gcg aac gag gtg aac gca tga              1146
Arg Ala Tyr Tyr Glu Arg Ile Ala Asn Glu Val Asn Ala
        370                 375                 380

<210> SEQ ID NO 20
<211> LENGTH: 381
<212> TYPE: PRT
<213> ORGANISM: Burkholderia cepacia

<400> SEQUENCE: 20

Met Glu Ser Ile Gly Ile Val Ala Pro Gln Lys Met His Phe Thr Glu
1               5                   10                  15

Pro Leu Pro Leu Gln Asn Gly Ser Ser Leu Ala Gly Tyr Asp Leu Met
            20                  25                  30

Val Glu Thr Tyr Gly Thr Leu Asn Ala Ala Arg Ser Asn Ala Val Leu
        35                  40                  45

Val Cys His Ala Leu Asn Ala Ser His His Val Ala Gly Val Tyr Ala
    50                  55                  60

Asp Asn Pro Arg Asp Ile Gly Trp Trp Asp Asn Met Val Gly Pro Gly
65                  70                  75                  80

Lys Pro Leu Asp Thr Asp Lys Phe Phe Val Ile Gly Val Asn Asn Leu
                85                  90                  95

Gly Ser Cys Phe Gly Ser Thr Gly Pro Met Ser Ile Asp Pro Ser Thr
            100                 105                 110

Gly Asn Pro Tyr Gly Ala Thr Phe Pro Val Val Thr Val Glu Asp Trp
        115                 120                 125

Val Asn Ala Gln Ala Arg Val Ala Asp Gln Phe Gly Ile Thr Arg Phe
    130                 135                 140

Ala Ala Val Met Gly Gly Ser Leu Gly Gly Met Gln Ala Leu Ala Trp
145                 150                 155                 160

Ser Met Met Tyr Pro Glu Arg Val Ala His Cys Ile Val Ala Ser
                165                 170                 175

Thr Pro Lys Leu Ser Ala Gln Asn Ile Ala Phe Asn Glu Val Ala Arg
            180                 185                 190

Ser Ala Ile Leu Ser Asp Pro Asp Phe His Gly Gly Asn Tyr Tyr Ala
        195                 200                 205

His Asn Val Lys Pro Lys Arg Gly Leu Arg Val Ala Arg Met Ile Gly
    210                 215                 220
```

```
His Ile Thr Tyr Leu Ser Asp Asp Met Ala Glu Lys Phe Gly Arg
225                 230                 235                 240

Ser Leu Arg Arg Ala Glu Gly Ala Leu Asp Ala Tyr Asn Phe Asn Phe
                245                 250                 255

Asp Val Glu Phe Glu Val Glu Ser Tyr Leu Arg Tyr Gln Gly Asp Lys
            260                 265                 270

Phe Ala Asp Tyr Phe Asp Ala Asn Thr Tyr Leu Leu Ile Thr Arg Ala
        275                 280                 285

Leu Asp Tyr Phe Asp Pro Ala Lys Ala Phe Ala Gly Asp Leu Thr Ala
    290                 295                 300

Ala Val Ala His Thr Thr Ala Lys Tyr Leu Ile Ala Ser Phe Thr Thr
305                 310                 315                 320

Asp Trp Arg Phe Ala Pro Ala Arg Ser Arg Glu Leu Val Lys Ala Leu
                325                 330                 335

Leu Asp His Lys Arg Thr Val Thr Tyr Ala Glu Ile Asp Ala Pro His
            340                 345                 350

Gly His Asp Ala Phe Leu Leu Asp Asp Ala Arg Tyr His Asn Leu Met
        355                 360                 365

Arg Ala Tyr Tyr Glu Arg Ile Ala Asn Glu Val Asn Ala
    370                 375                 380

<210> SEQ ID NO 21
<211> LENGTH: 1134
<212> TYPE: DNA
<213> ORGANISM: Nitrosomonas europaea
<220> FEATURE:
<221> NAME/KEY: CDS
<222> LOCATION: (1)..(1131)
<223> OTHER INFORMATION: RNE02005

<400> SEQUENCE: 21 atg tcc aca caa gat tct gat tcg atc ggc atc gta tcg gca cga cgc      48
Met Ser Thr Gln Asp Ser Asp Ser Ile Gly Ile Val Ser Ala Arg Arg
  1               5                  10                  15 gcc cat ttc gac acc ccg ctc agc ctg aaa agc gga gct gta ctg gac      96
Ala His Phe Asp Thr Pro Leu Ser Leu Lys Ser Gly Ala Val Leu Asp
                 20                  25                  30 agc tac gag ctc gtc tat gaa acc tat ggg gag ctg aat gca gac cga     144
Ser Tyr Glu Leu Val Tyr Glu Thr Tyr Gly Glu Leu Asn Ala Asp Arg
             35                  40                  45 tcc aat gca gtg ctg atc tgc cat gct tta tcc ggc aac cac cat gtt     192
Ser Asn Ala Val Leu Ile Cys His Ala Leu Ser Gly Asn His His Val
         50                  55                  60 gcc ggt gtt tat gca gat aac ccc aag aat acc gga tgg tgg aac aac     240
Ala Gly Val Tyr Ala Asp Asn Pro Lys Asn Thr Gly Trp Trp Asn Asn
 65                  70                  75                  80 atg atc ggt ccg ggc aaa ccg gtc gat acc cga aaa ttc ttt gtc atc     288
Met Ile Gly Pro Gly Lys Pro Val Asp Thr Arg Lys Phe Phe Val Ile
                 85                  90                  95 ggt atc aat aat ctc ggg ggt tgc cat ggc tcc acc ggg ccc atc agc     336
Gly Ile Asn Asn Leu Gly Gly Cys His Gly Ser Thr Gly Pro Ile Ser
                100                 105                 110 atc aac gac aag acc ggt aaa cgc ttc ggc ccg gat ttt ccg ctg gta     384
Ile Asn Asp Lys Thr Gly Lys Arg Phe Gly Pro Asp Phe Pro Leu Val
            115                 120                 125 acg aca gct gac tgg gca aaa acc tat gtc cgt ttc gcc gat cag ttc     432
Thr Thr Ala Asp Trp Ala Lys Thr Tyr Val Arg Phe Ala Asp Gln Phe
        130                 135                 140 agc atc gac tgt ttt gcc gcc gtc atc ggt ggc agt ctg ggc ggg atg     480
```

```
                                                    -continued

Ser Ile Asp Cys Phe Ala Ala Val Ile Gly Gly Ser Leu Gly Gly Met
145                 150                 155                 160 tcg gcc atg caa ctg gcg ctc gat gca ccg gaa aga gtt cgt cat gcc      528
Ser Ala Met Gln Leu Ala Leu Asp Ala Pro Glu Arg Val Arg His Ala
                165                 170                 175 ata gtg gtt gca gca tcg gcc agg ctg aca gca cag aac atc gct ttc      576
Ile Val Val Ala Ala Ser Ala Arg Leu Thr Ala Gln Asn Ile Ala Phe
            180                 185                 190 aat gat gtc gcg cgt cag gcg att ctg acc gac cct gat ttt cac gac      624
Asn Asp Val Ala Arg Gln Ala Ile Leu Thr Asp Pro Asp Phe His Asp
        195                 200                 205 ggc gac tat tat tcc cat ggc acc cac ccg cgc aga ggt tta cgc ctt      672
Gly Asp Tyr Tyr Ser His Gly Thr His Pro Arg Arg Gly Leu Arg Leu
    210                 215                 220 gcc cgc atg ctt ggc cac atc acc tac ctg tcg gac gac tcc atg gcc      720
Ala Arg Met Leu Gly His Ile Thr Tyr Leu Ser Asp Asp Ser Met Ala
225                 230                 235                 240 agc aaa ttc ggc cgt gag tta cgt aac ggc tcg ctt gct ttc aat tat      768
Ser Lys Phe Gly Arg Glu Leu Arg Asn Gly Ser Leu Ala Phe Asn Tyr
                245                 250                 255 gat gtg gaa ttc cag atc gaa tcc tat ctg cac cat cag ggc gac aaa      816
Asp Val Glu Phe Gln Ile Glu Ser Tyr Leu His His Gln Gly Asp Lys
            260                 265                 270 ttt gcc gac ctg ttc gac gca aac act tat ctg ctg atg acg aag gcg      864
Phe Ala Asp Leu Phe Asp Ala Asn Thr Tyr Leu Leu Met Thr Lys Ala
        275                 280                 285 ctc gat tat ttc gat ccg gcc cag gat tac gat ggc aac ctg agt gca      912
Leu Asp Tyr Phe Asp Pro Ala Gln Asp Tyr Asp Gly Asn Leu Ser Ala
    290                 295                 300 gcc ttt gcc cgt gca caa gcg gat ttt ctg gta ctt tcc ttt act tcc      960
Ala Phe Ala Arg Ala Gln Ala Asp Phe Leu Val Leu Ser Phe Thr Ser
305                 310                 315                 320 gac tgg cgt ttt tcc ccg gag cgt tcg cgc gat atc gtc aag gca ctg     1008
Asp Trp Arg Phe Ser Pro Glu Arg Ser Arg Asp Ile Val Lys Ala Leu
                325                 330                 335 ctc gac aac aaa ctg aat gtc agt tat gcg gaa att ccc tcc tcg tac     1056
Leu Asp Asn Lys Leu Asn Val Ser Tyr Ala Glu Ile Pro Ser Ser Tyr
            340                 345                 350 gga cat gat tcc ttt ctc atg cag gac gac tac tat cac cag ttg ata     1104
Gly His Asp Ser Phe Leu Met Gln Asp Asp Tyr Tyr His Gln Leu Ile
        355                 360                 365 cgt gct tac atg aac aat atc gct ctc tag                             1134
Arg Ala Tyr Met Asn Asn Ile Ala Leu
    370                 375

<210> SEQ ID NO 22
<211> LENGTH: 377
<212> TYPE: PRT
<213> ORGANISM: Nitrosomonas europaea

<400> SEQUENCE: 22

Met Ser Thr Gln Asp Ser Asp Ser Ile Gly Ile Val Ser Ala Arg Arg
1               5                   10                  15

Ala His Phe Asp Thr Pro Leu Ser Leu Lys Ser Gly Ala Val Leu Asp
                20                  25                  30

Ser Tyr Glu Leu Val Tyr Glu Thr Tyr Gly Glu Leu Asn Ala Asp Arg
            35                  40                  45

Ser Asn Ala Val Leu Ile Cys His Ala Leu Ser Gly Asn His His Val
        50                  55                  60
```

```
Ala Gly Val Tyr Ala Asp Asn Pro Lys Asn Thr Gly Trp Trp Asn Asn
 65                  70                  75                  80

Met Ile Gly Pro Gly Lys Pro Val Asp Thr Arg Lys Phe Phe Val Ile
                 85                  90                  95

Gly Ile Asn Asn Leu Gly Gly Cys His Gly Ser Thr Gly Pro Ile Ser
            100                 105                 110

Ile Asn Asp Lys Thr Gly Lys Arg Phe Gly Pro Asp Phe Pro Leu Val
        115                 120                 125

Thr Thr Ala Asp Trp Ala Lys Thr Tyr Val Arg Phe Ala Asp Gln Phe
130                 135                 140

Ser Ile Asp Cys Phe Ala Ala Val Ile Gly Ser Leu Gly Gly Met
145                 150                 155                 160

Ser Ala Met Gln Leu Ala Leu Asp Ala Pro Glu Arg Val Arg His Ala
                165                 170                 175

Ile Val Val Ala Ala Ser Ala Arg Leu Thr Ala Gln Asn Ile Ala Phe
            180                 185                 190

Asn Asp Val Ala Arg Gln Ala Ile Leu Thr Asp Pro Asp Phe His Asp
        195                 200                 205

Gly Asp Tyr Tyr Ser His Gly Thr His Pro Arg Arg Gly Leu Arg Leu
210                 215                 220

Ala Arg Met Leu Gly His Ile Thr Tyr Leu Ser Asp Asp Ser Met Ala
225                 230                 235                 240

Ser Lys Phe Gly Arg Glu Leu Arg Asn Gly Ser Leu Ala Phe Asn Tyr
                245                 250                 255

Asp Val Glu Phe Gln Ile Glu Ser Tyr Leu His His Gln Gly Asp Lys
            260                 265                 270

Phe Ala Asp Leu Phe Asp Ala Asn Thr Tyr Leu Leu Met Thr Lys Ala
        275                 280                 285

Leu Asp Tyr Phe Asp Pro Ala Gln Asp Tyr Asp Gly Asn Leu Ser Ala
290                 295                 300

Ala Phe Ala Arg Ala Gln Ala Asp Phe Leu Val Leu Ser Phe Thr Ser
305                 310                 315                 320

Asp Trp Arg Phe Ser Pro Glu Arg Ser Arg Asp Ile Val Lys Ala Leu
                325                 330                 335

Leu Asp Asn Lys Leu Asn Val Ser Tyr Ala Glu Ile Pro Ser Ser Tyr
            340                 345                 350

Gly His Asp Ser Phe Leu Met Gln Asp Asp Tyr Tyr His Gln Leu Ile
        355                 360                 365

Arg Ala Tyr Met Asn Asn Ile Ala Leu
370                 375
```

<210> SEQ ID NO 23
<211> LENGTH: 1077
<212> TYPE: DNA
<213> ORGANISM: Haemophilus influenzae
<220> FEATURE:
<221> NAME/KEY: CDS
<222> LOCATION: (1)..(1074)
<223> OTHER INFORMATION: RHI02681

<400> SEQUENCE: 23

```
atg tct gtg caa aat gta gtg ctt ttt gac aca cag cct tta act ctg    48
Met Ser Val Gln Asn Val Val Leu Phe Asp Thr Gln Pro Leu Thr Leu
  1               5                  10                  15 atg ctt ggc ggc aaa ctt tcc cat att aat gtc gcg tat caa act tat   96
Met Leu Gly Gly Lys Leu Ser His Ile Asn Val Ala Tyr Gln Thr Tyr
             20                  25                  30
```

-continued

```
ggc acg ctc aat gcc gaa aaa aat aat gcg gta tta att tgc cac gct      144
Gly Thr Leu Asn Ala Glu Lys Asn Asn Ala Val Leu Ile Cys His Ala
        35                  40                  45 ttg act ggt gat gct gag cct tat ttc gat gat ggt cga gat ggc tgg      192
Leu Thr Gly Asp Ala Glu Pro Tyr Phe Asp Asp Gly Arg Asp Gly Trp
 50                  55                  60 tgg cag aat ttt atg gga gca ggt tta gca ttg gat acg gat cgt tat      240
Trp Gln Asn Phe Met Gly Ala Gly Leu Ala Leu Asp Thr Asp Arg Tyr
 65                  70                  75                  80 ttt ttt att agc tcg aac gta tta ggt ggt tgc aag gga aca act ggg      288
Phe Phe Ile Ser Ser Asn Val Leu Gly Gly Cys Lys Gly Thr Thr Gly
                 85                  90                  95 cct tca tca att aat ccg caa acg ggt aaa cct tat ggc agc caa ttt      336
Pro Ser Ser Ile Asn Pro Gln Thr Gly Lys Pro Tyr Gly Ser Gln Phe
            100                 105                 110 cct aat att gtt gtg caa gat att gtt aaa gta caa aaa gcc ttg ctt      384
Pro Asn Ile Val Val Gln Asp Ile Val Lys Val Gln Lys Ala Leu Leu
        115                 120                 125 gat cat ctt ggt att agc cat tta aaa gcc att att ggt gga tct ttt      432
Asp His Leu Gly Ile Ser His Leu Lys Ala Ile Ile Gly Gly Ser Phe
130                 135                 140 ggc ggc atg caa gcg aat caa tgg gcg att gat tat cct gat ttt atg      480
Gly Gly Met Gln Ala Asn Gln Trp Ala Ile Asp Tyr Pro Asp Phe Met
145                 150                 155                 160 gat aat atc gtg aat ctt tgc tca tcc att tat ttt agt gct gaa gcc      528
Asp Asn Ile Val Asn Leu Cys Ser Ser Ile Tyr Phe Ser Ala Glu Ala
                165                 170                 175 ata ggt ttt aat cac gta atg cgt caa gcg gtc att aat gat ccc aat      576
Ile Gly Phe Asn His Val Met Arg Gln Ala Val Ile Asn Asp Pro Asn
            180                 185                 190 ttt aac ggc ggc gat tat tat gag ggt aca ccg cca gat caa ggg tta      624
Phe Asn Gly Gly Asp Tyr Tyr Glu Gly Thr Pro Pro Asp Gln Gly Leu
        195                 200                 205 tct att gca cgt atg cta ggt atg ctg act tac cgc acc gat tta caa      672
Ser Ile Ala Arg Met Leu Gly Met Leu Thr Tyr Arg Thr Asp Leu Gln
    210                 215                 220 ctt gcg aaa gcc ttt ggg cgt gcc aca aaa tca gat ggc agc ttt tgg      720
Leu Ala Lys Ala Phe Gly Arg Ala Thr Lys Ser Asp Gly Ser Phe Trp
225                 230                 235                 240 ggc gat tac ttt caa gtg gaa tcc tat ctt tct tac caa ggc aaa aaa      768
Gly Asp Tyr Phe Gln Val Glu Ser Tyr Leu Ser Tyr Gln Gly Lys Lys
                245                 250                 255 ttc tta gaa cgt ttt gat gcc aat agt tat ttg cat ttg tta cgt gcg      816
Phe Leu Glu Arg Phe Asp Ala Asn Ser Tyr Leu His Leu Leu Arg Ala
            260                 265                 270 ttg gat atg tat gat cca agt ttg ggg tat gac aat gtt aaa gag gca      864
Leu Asp Met Tyr Asp Pro Ser Leu Gly Tyr Asp Asn Val Lys Glu Ala
        275                 280                 285 tta tca cgt att aaa gca cgc tat acg ttg gtt tct gtg aca acg gat      912
Leu Ser Arg Ile Lys Ala Arg Tyr Thr Leu Val Ser Val Thr Thr Asp
    290                 295                 300 caa ctt ttt aaa ccc att gat ctt tat aaa agt aaa cag ctt tta gag      960
Gln Leu Phe Lys Pro Ile Asp Leu Tyr Lys Ser Lys Gln Leu Leu Glu
305                 310                 315                 320 caa agt gga gtc gat cta cat ttt tat gaa ttc cca tca gat tac gga     1008
Gln Ser Gly Val Asp Leu His Phe Tyr Glu Phe Pro Ser Asp Tyr Gly
                325                 330                 335 cac gat gcg ttt tta gtg gat tat gat cag ttt gaa aaa cga att cga     1056
His Asp Ala Phe Leu Val Asp Tyr Asp Gln Phe Glu Lys Arg Ile Arg
```

```
                  340             345             350
gat ggt ttg gca ggt aat taa                                          1077
Asp Gly Leu Ala Gly Asn
        355

<210> SEQ ID NO 24
<211> LENGTH: 358
<212> TYPE: PRT
<213> ORGANISM: Haemophilus influenzae

<400> SEQUENCE: 24

Met Ser Val Gln Asn Val Val Leu Phe Asp Thr Gln Pro Leu Thr Leu
 1               5                  10                  15

Met Leu Gly Gly Lys Leu Ser His Ile Asn Val Ala Tyr Gln Thr Tyr
            20                  25                  30

Gly Thr Leu Asn Ala Glu Lys Asn Asn Ala Val Leu Ile Cys His Ala
        35                  40                  45

Leu Thr Gly Asp Ala Glu Pro Tyr Phe Asp Asp Gly Arg Asp Gly Trp
    50                  55                  60

Trp Gln Asn Phe Met Gly Ala Gly Leu Ala Leu Asp Thr Asp Arg Tyr
65                  70                  75                  80

Phe Phe Ile Ser Ser Asn Val Leu Gly Gly Cys Lys Gly Thr Thr Gly
                85                  90                  95

Pro Ser Ser Ile Asn Pro Gln Thr Gly Lys Pro Tyr Gly Ser Gln Phe
            100                 105                 110

Pro Asn Ile Val Val Gln Asp Ile Val Lys Val Gln Lys Ala Leu Leu
        115                 120                 125

Asp His Leu Gly Ile Ser His Leu Lys Ala Ile Ile Gly Gly Ser Phe
    130                 135                 140

Gly Gly Met Gln Ala Asn Gln Trp Ala Ile Asp Tyr Pro Asp Phe Met
145                 150                 155                 160

Asp Asn Ile Val Asn Leu Cys Ser Ser Ile Tyr Phe Ser Ala Glu Ala
                165                 170                 175

Ile Gly Phe Asn His Val Met Arg Gln Ala Val Ile Asn Asp Pro Asn
            180                 185                 190

Phe Asn Gly Gly Asp Tyr Tyr Glu Gly Thr Pro Pro Asp Gln Gly Leu
        195                 200                 205

Ser Ile Ala Arg Met Leu Gly Met Leu Thr Tyr Arg Thr Asp Leu Gln
    210                 215                 220

Leu Ala Lys Ala Phe Gly Arg Ala Thr Lys Ser Asp Gly Ser Phe Trp
225                 230                 235                 240

Gly Asp Tyr Phe Gln Val Glu Ser Tyr Leu Ser Tyr Gln Gly Lys Lys
                245                 250                 255

Phe Leu Glu Arg Phe Asp Ala Asn Ser Tyr Leu His Leu Leu Arg Ala
            260                 265                 270

Leu Asp Met Tyr Asp Pro Ser Leu Gly Tyr Asp Asn Val Lys Glu Ala
        275                 280                 285

Leu Ser Arg Ile Lys Ala Arg Tyr Thr Leu Val Ser Val Thr Thr Asp
    290                 295                 300

Gln Leu Phe Lys Pro Ile Asp Leu Tyr Lys Ser Lys Gln Leu Leu Glu
305                 310                 315                 320

Gln Ser Gly Val Asp Leu His Phe Tyr Glu Phe Pro Ser Asp Tyr Gly
                325                 330                 335

His Asp Ala Phe Leu Val Asp Tyr Asp Gln Phe Glu Lys Arg Ile Arg
            340                 345                 350
```

-continued

```
Asp Gly Leu Ala Gly Asn
        355

<210> SEQ ID NO 25
<211> LENGTH: 1296
<212> TYPE: DNA
<213> ORGANISM: Halobacterium sp
<220> FEATURE:
<221> NAME/KEY: CDS
<222> LOCATION: (1)..(1293)
<223> OTHER INFORMATION: ETX_HALN1

<400> SEQUENCE: 25 atg ggc cac gat cac gga ctc cac acc aac agt gta cac gcc ggc cag      48
Met Gly His Asp His Gly Leu His Thr Asn Ser Val His Ala Gly Gln
 1               5                  10                  15 cgc gtc gac ccg gcc acg ggc gct cgc gcg ccg cca ctc tac cag acc      96
Arg Val Asp Pro Ala Thr Gly Ala Arg Ala Pro Pro Leu Tyr Gln Thr
            20                  25                  30 acg tcg tac gcc ttc gag gac agc gcc gat gcc gcc ggc cag ttc gcc     144
Thr Ser Tyr Ala Phe Glu Asp Ser Ala Asp Ala Ala Gly Gln Phe Ala
        35                  40                  45 ctt gag cgg gac ggc tac atc tac tcg cgg ctg atg aac ccc acc gtg     192
Leu Glu Arg Asp Gly Tyr Ile Tyr Ser Arg Leu Met Asn Pro Thr Val
    50                  55                  60 gag acc ctc cag gac cgc ctc gcc gcc ctc gaa ggc ggc gtc ggc gcg     240
Glu Thr Leu Gln Asp Arg Leu Ala Ala Leu Glu Gly Gly Val Gly Ala
 65                  70                  75                  80 gtc gcc acc gcg tcc gga atg gcc gcc ctg gac ctc gcg acg ttc ctg     288
Val Ala Thr Ala Ser Gly Met Ala Ala Leu Asp Leu Ala Thr Phe Leu
                85                  90                  95 ctg gca cgc gcc ggc gac tcc gtc gtc gcc gcc agc gac ctc tac ggc     336
Leu Ala Arg Ala Gly Asp Ser Val Val Ala Ala Ser Asp Leu Tyr Gly
            100                 105                 110 ggc acc gtg acg tac ctc acg cac agc gcc cag cgc cgc ggc gtc gac     384
Gly Thr Val Thr Tyr Leu Thr His Ser Ala Gln Arg Arg Gly Val Asp
        115                 120                 125 acg acg ttc gtg gac gtc ctc gac tac gac gcc tac gcc gac gcc atc     432
Thr Thr Phe Val Asp Val Leu Asp Tyr Asp Ala Tyr Ala Asp Ala Ile
    130                 135                 140 gac gcc gac acc gcc tac gtg ctc gtc gaa acc gtc ggc aac ccc agc     480
Asp Ala Asp Thr Ala Tyr Val Leu Val Glu Thr Val Gly Asn Pro Ser
145                 150                 155                 160 ctg atc acg ccc gac ctc gaa cgc atc gcc gac atc gcc cac gac aac     528
Leu Ile Thr Pro Asp Leu Glu Arg Ile Ala Asp Ile Ala His Asp Asn
                165                 170                 175 ggc gtt ccc ctg ctg gtg gac aac acg ttc gcg acc ccc gcg ctg gca     576
Gly Val Pro Leu Leu Val Asp Asn Thr Phe Ala Thr Pro Ala Leu Ala
            180                 185                 190 acc ccg atc gac cac ggt gcc gac atc gtc tgg cac tcc acc acc aaa     624
Thr Pro Ile Asp His Gly Ala Asp Ile Val Trp His Ser Thr Thr Lys
        195                 200                 205 tgg atc cac ggt gcc ggc acc acc gtc ggc ggc gcg ctc gtc gac gcc     672
Trp Ile His Gly Ala Gly Thr Thr Val Gly Gly Ala Leu Val Asp Ala
    210                 215                 220 ggc agc ttc gac tgg gac gcc cac gcc gcc gac tac ccc gag atc gcc     720
Gly Ser Phe Asp Trp Asp Ala His Ala Ala Asp Tyr Pro Glu Ile Ala
225                 230                 235                 240 cag gaa aac ccc gcc tac cac ggc gtg acc ttc acc gat cgc ttc ggg     768
Gln Glu Asn Pro Ala Tyr His Gly Val Thr Phe Thr Asp Arg Phe Gly
                245                 250                 255
```

```
gac gcc gcg ttc acg tac gcc gca atc gcc cgc ggg ctg cgc gat ctg      816
Asp Ala Ala Phe Thr Tyr Ala Ala Ile Ala Arg Gly Leu Arg Asp Leu
        260                 265                 270 ggc aac cag cag tcg ccg ttc gac gcc tgg cag acc ctc cag aag ctc      864
Gly Asn Gln Gln Ser Pro Phe Asp Ala Trp Gln Thr Leu Gln Lys Leu
    275                 280                 285 gaa acg ctc ccg ctg cgc atg caa caa cac tgc cgg aac gcc cag ctc      912
Glu Thr Leu Pro Leu Arg Met Gln Gln His Cys Arg Asn Ala Gln Leu
290                 295                 300 gtc gcc gaa cac ctc cgg gac cac ccc aac gtg tcg tgg gtc aac tac      960
Val Ala Glu His Leu Arg Asp His Pro Asn Val Ser Trp Val Asn Tyr
305                 310                 315                 320 ccc ggg ctg gcc gac cac gac acc cac gac aac gca acc acc tac ctc     1008
Pro Gly Leu Ala Asp His Asp Thr His Asp Asn Ala Thr Thr Tyr Leu
                325                 330                 335 gat tcg ggc tac gga ggc atg ctc acg ttc ggc gtc gag gac ggc tac     1056
Asp Ser Gly Tyr Gly Gly Met Leu Thr Phe Gly Val Glu Asp Gly Tyr
            340                 345                 350 gag gcc gcc caa tcg gtc acc gag gag acc acg ctt gcc agc ctg ctg     1104
Glu Ala Ala Gln Ser Val Thr Glu Glu Thr Thr Leu Ala Ser Leu Leu
        355                 360                 365 gcg aac gtc ggc gac gcc aaa acg ctc gtg atc cac ccc gcc tcc acc     1152
Ala Asn Val Gly Asp Ala Lys Thr Leu Val Ile His Pro Ala Ser Thr
    370                 375                 380 acc cac cag cag ctc acc ccc gaa gcc cag cgc gcc ggc ggt gtg cgc     1200
Thr His Gln Gln Leu Thr Pro Glu Ala Gln Arg Ala Gly Gly Val Arg
385                 390                 395                 400 ccc gag atg gtg cgg gtg tcg gtc ggc atc gag gac ccc gcc gac atc     1248
Pro Glu Met Val Arg Val Ser Val Gly Ile Glu Asp Pro Ala Asp Ile
                405                 410                 415 gtc gcg gac ctc gaa acc gcc atc gag gcc gcg gtc ggg tcg gcg         1293
Val Ala Asp Leu Glu Thr Ala Ile Glu Ala Ala Val Gly Ser Ala
            420                 425                 430 tag                                                                   1296
```

<210> SEQ ID NO 26
<211> LENGTH: 431
<212> TYPE: PRT
<213> ORGANISM: Halobacterium sp

<400> SEQUENCE: 26

```
Met Gly His Asp His Gly Leu His Thr Asn Ser Val His Ala Gly Gln
 1               5                  10                  15

Arg Val Asp Pro Ala Thr Gly Ala Arg Ala Pro Pro Leu Tyr Gln Thr
                20                  25                  30

Thr Ser Tyr Ala Phe Glu Asp Ser Ala Asp Ala Ala Gly Gln Phe Ala
            35                  40                  45

Leu Glu Arg Asp Gly Tyr Ile Tyr Ser Arg Leu Met Asn Pro Thr Val
        50                  55                  60

Glu Thr Leu Gln Asp Arg Leu Ala Ala Leu Glu Gly Gly Val Gly Ala
 65                 70                  75                  80

Val Ala Thr Ala Ser Gly Met Ala Ala Leu Asp Leu Ala Thr Phe Leu
                85                  90                  95

Leu Ala Arg Ala Gly Asp Ser Val Val Ala Ala Ser Asp Leu Tyr Gly
            100                 105                 110

Gly Thr Val Thr Tyr Leu Thr His Ser Ala Gln Arg Arg Gly Val Asp
        115                 120                 125
```

```
Thr Thr Phe Val Asp Val Leu Asp Tyr Asp Ala Tyr Ala Asp Ala Ile
    130                 135                 140
Asp Ala Asp Thr Ala Tyr Val Leu Val Glu Thr Val Gly Asn Pro Ser
145                 150                 155                 160
Leu Ile Thr Pro Asp Leu Glu Arg Ile Ala Asp Ile Ala His Asp Asn
                165                 170                 175
Gly Val Pro Leu Leu Val Asp Asn Thr Phe Ala Thr Pro Ala Leu Ala
            180                 185                 190
Thr Pro Ile Asp His Gly Ala Asp Ile Val Trp His Ser Thr Thr Lys
        195                 200                 205
Trp Ile His Gly Ala Gly Thr Thr Val Gly Gly Ala Leu Val Asp Ala
    210                 215                 220
Gly Ser Phe Asp Trp Asp Ala His Ala Ala Asp Tyr Pro Glu Ile Ala
225                 230                 235                 240
Gln Glu Asn Pro Ala Tyr His Gly Val Thr Phe Thr Asp Arg Phe Gly
                245                 250                 255
Asp Ala Ala Phe Thr Tyr Ala Ala Ile Ala Arg Gly Leu Arg Asp Leu
            260                 265                 270
Gly Asn Gln Gln Ser Pro Phe Asp Ala Trp Gln Thr Leu Gln Lys Leu
        275                 280                 285
Glu Thr Leu Pro Leu Arg Met Gln Gln His Cys Arg Asn Ala Gln Leu
    290                 295                 300
Val Ala Glu His Leu Arg Asp His Pro Asn Val Ser Trp Val Asn Tyr
305                 310                 315                 320
Pro Gly Leu Ala Asp His Asp Thr His Asp Asn Ala Thr Thr Tyr Leu
                325                 330                 335
Asp Ser Gly Tyr Gly Gly Met Leu Thr Phe Gly Val Glu Asp Gly Tyr
            340                 345                 350
Glu Ala Ala Gln Ser Val Thr Glu Gly Thr Thr Leu Ala Ser Leu Leu
        355                 360                 365
Ala Asn Val Gly Asp Ala Lys Thr Leu Val Ile His Pro Ala Ser Thr
    370                 375                 380
Thr His Gln Gln Leu Thr Pro Glu Ala Gln Arg Ala Gly Gly Val Arg
385                 390                 395                 400
Pro Glu Met Val Arg Val Ser Val Gly Ile Glu Asp Pro Ala Asp Ile
                405                 410                 415
Val Ala Asp Leu Glu Thr Ala Ile Glu Ala Ala Val Gly Ser Ala
            420                 425                 430

<210> SEQ ID NO 27
<211> LENGTH: 1143
<212> TYPE: DNA
<213> ORGANISM: Thermus thermophilus
<220> FEATURE:
<221> NAME/KEY: CDS
<222> LOCATION: (1)..(1140)
<223> OTHER INFORMATION: RTT00268

<400> SEQUENCE: 27 atg agc gag atc gcc ctc gag gcc tgg ggg gag cac gag gcc ctc ctc      48
Met Ser Glu Ile Ala Leu Glu Ala Trp Gly Glu His Glu Ala Leu Leu
  1               5                  10                  15 ctc aag ccc ccc cgc tcc ccc ctc tcc atc ccc ccg ccc aag ccc cgc      96
Leu Lys Pro Pro Arg Ser Pro Leu Ser Ile Pro Pro Pro Lys Pro Arg
             20                  25                  30 acc gcc gtc ctc ttc ccc agg cgg gag ggg ttc tac acg gag ctc ggg     144
Thr Ala Val Leu Phe Pro Arg Arg Glu Gly Phe Tyr Thr Glu Leu Gly
```

-continued

|  |  |  |  | 35 |  |  |  | 40 |  |  |  | 45 |  |  |  |
|---|---|---|---|---|---|---|---|---|---|---|---|---|---|---|---|
| ggg | tac | ctc | ccc | gag | gtg | cgc | ctc | cgc | ttt | gag | acc | tac | ggg | acc | ctc | 192 |
| Gly | Tyr | Leu | Pro | Glu | Val | Arg | Leu | Arg | Phe | Glu | Thr | Tyr | Gly | Thr | Leu |  |
|  | 50 |  |  |  | 55 |  |  |  | 60 |  |  |  |  |  |  |  |

| tcc | cgc | agg | cgg | gat | aac | gcc | gtc | ctc | gtc | ttc | cac | gcc | ctc | acg | ggg | 240 |
| Ser | Arg | Arg | Arg | Asp | Asn | Ala | Val | Leu | Val | Phe | His | Ala | Leu | Thr | Gly |  |
| 65 |  |  |  |  | 70 |  |  |  | 75 |  |  |  |  | 80 |  |  |

| agc | gcc | cac | ctg | gcg | ggg | acc | tac | gac | gag | gaa | acc | ttt | aga | agc | ctc | 288 |
| Ser | Ala | His | Leu | Ala | Gly | Thr | Tyr | Asp | Glu | Glu | Thr | Phe | Arg | Ser | Leu |  |
|  |  |  |  | 85 |  |  |  |  | 90 |  |  |  |  | 95 |  |  |

| tcc | ccc | ctg | gag | cag | gcc | ttc | ggc | cgg | gaa | ggg | tgg | tgg | gac | agc | ctg | 336 |
| Ser | Pro | Leu | Glu | Gln | Ala | Phe | Gly | Arg | Glu | Gly | Trp | Trp | Asp | Ser | Leu |  |
|  |  |  |  | 100 |  |  |  |  | 105 |  |  |  |  | 110 |  |  |

| gtg | ggg | ccc | ggg | cgg | atc | ctg | gac | ccc | gcc | ctc | tac | tac | gtg | gtc | tcc | 384 |
| Val | Gly | Pro | Gly | Arg | Ile | Leu | Asp | Pro | Ala | Leu | Tyr | Tyr | Val | Val | Ser |  |
|  |  |  |  | 115 |  |  |  |  | 120 |  |  |  |  | 125 |  |  |

| gcc | aac | cac | ctg | gga | agc | tgc | tac | ggc | tcc | acc | ggc | ccc | ctc | tcc | cta | 432 |
| Ala | Asn | His | Leu | Gly | Ser | Cys | Tyr | Gly | Ser | Thr | Gly | Pro | Leu | Ser | Leu |  |
|  |  |  |  | 130 |  |  |  |  | 135 |  |  |  |  | 140 |  |  |

| gac | ccc | cac | acg | ggc | cgc | ccc | tac | ggg | agg | gac | ttc | cct | ccc | ctt | acc | 480 |
| Asp | Pro | His | Thr | Gly | Arg | Pro | Tyr | Gly | Arg | Asp | Phe | Pro | Pro | Leu | Thr |  |
| 145 |  |  |  |  | 150 |  |  |  |  | 155 |  |  |  |  | 160 |  |

| atc | cgc | gac | ctg | gcc | cgg | gcc | cag | gcg | agg | ctt | ctg | gac | cat | ctg | ggg | 528 |
| Ile | Arg | Asp | Leu | Ala | Arg | Ala | Gln | Ala | Arg | Leu | Leu | Asp | His | Leu | Gly |  |
|  |  |  |  | 165 |  |  |  |  | 170 |  |  |  |  | 175 |  |  |

| gtg | gag | aag | gcc | atc | gtc | atc | ggg | ggg | agc | ctc | ggg | ggg | atg | gtg | gcc | 576 |
| Val | Glu | Lys | Ala | Ile | Val | Ile | Gly | Gly | Ser | Leu | Gly | Gly | Met | Val | Ala |  |
|  |  |  |  | 180 |  |  |  |  | 185 |  |  |  |  | 190 |  |  |

| ctg | gag | ttc | gcc | ctc | atg | tac | ccg | gag | agg | gtg | aag | aag | ctc | gtg | gtc | 624 |
| Leu | Glu | Phe | Ala | Leu | Met | Tyr | Pro | Glu | Arg | Val | Lys | Lys | Leu | Val | Val |  |
|  |  |  |  | 195 |  |  |  |  | 200 |  |  |  |  | 205 |  |  |

| ctg | gcg | gcc | ccc | gca | cgg | cac | ggc | ccc | tgg | gcc | cgg | gcc | ttc | aac | cac | 672 |
| Leu | Ala | Ala | Pro | Ala | Arg | His | Gly | Pro | Trp | Ala | Arg | Ala | Phe | Asn | His |  |
|  |  |  |  | 210 |  |  |  |  | 215 |  |  |  |  | 220 |  |  |

| ctc | tcc | cgc | cag | gcc | atc | ctc | caa | gac | ccc | gag | tac | cag | aag | ggc | aac | 720 |
| Leu | Ser | Arg | Gln | Ala | Ile | Leu | Gln | Asp | Pro | Glu | Tyr | Gln | Lys | Gly | Asn |  |
| 225 |  |  |  |  | 230 |  |  |  |  | 235 |  |  |  |  | 240 |  |

| cct | gcc | ccc | aag | ggc | atg | gcc | ctc | gcc | cgg | gga | atc | gcc | atg | atg | agc | 768 |
| Pro | Ala | Pro | Lys | Gly | Met | Ala | Leu | Ala | Arg | Gly | Ile | Ala | Met | Met | Ser |  |
|  |  |  |  | 245 |  |  |  |  | 250 |  |  |  |  | 255 |  |  |

| tac | cgg | gcc | ccc | gag | ggg | ttt | gag | gcc | cgc | tgg | ggc | gcg | gag | ccc | gag | 816 |
| Tyr | Arg | Ala | Pro | Glu | Gly | Phe | Glu | Ala | Arg | Trp | Gly | Ala | Glu | Pro | Glu |  |
|  |  |  |  | 260 |  |  |  |  | 265 |  |  |  |  | 270 |  |  |

| ctc | ggg | gaa | atc | cac | ctg | gac | tac | cag | ggg | gag | aag | ttc | ctc | cgg | cgc | 864 |
| Leu | Gly | Glu | Ile | His | Leu | Asp | Tyr | Gln | Gly | Glu | Lys | Phe | Leu | Arg | Arg |  |
|  |  |  |  | 275 |  |  |  |  | 280 |  |  |  |  | 285 |  |  |

| ttc | cac | gcc | gag | agc | tac | ctc | gtc | ctc | tcc | cgg | gcc | atg | gac | aac | cac | 912 |
| Phe | His | Ala | Glu | Ser | Tyr | Leu | Val | Leu | Ser | Arg | Ala | Met | Asp | Asn | His |  |
|  |  |  |  | 290 |  |  |  |  | 295 |  |  |  |  | 300 |  |  |

| gac | gtg | ggc | cgg | ggc | cgg | ggc | ggg | gtg | gag | gag | gcc | ctg | aag | cgc | ctc | 960 |
| Asp | Val | Gly | Arg | Gly | Arg | Gly | Gly | Val | Glu | Glu | Ala | Leu | Lys | Arg | Leu |  |
| 305 |  |  |  |  | 310 |  |  |  |  | 315 |  |  |  |  | 320 |  |

| agg | gcc | atc | ccc | tcc | ctc | ttc | gtg | ggc | att | gac | acc | gac | ctc | ctc | tac | 1008 |
| Arg | Ala | Ile | Pro | Ser | Leu | Phe | Val | Gly | Ile | Asp | Thr | Asp | Leu | Leu | Tyr |  |
|  |  |  |  | 325 |  |  |  |  | 330 |  |  |  |  | 335 |  |  |

| ccc | gcc | tgg | gag | gtg | agg | cag | gcg | gcc | aag | gcg | gcg | ggg | gcc | cgc | tac | 1056 |
| Pro | Ala | Trp | Glu | Val | Arg | Gln | Ala | Ala | Lys | Ala | Ala | Gly | Ala | Arg | Tyr |  |
|  |  |  |  | 340 |  |  |  |  | 345 |  |  |  |  | 350 |  |  |

| cgg | gag | atc | aaa | agc | ccc | cac | ggg | cac | gac | gcc | ttc | ctc | ata | gag | acc | 1104 |

Arg Glu Ile Lys Ser Pro His Gly His Asp Ala Phe Leu Ile Glu Thr
            355                 360                 365 gac cag gtg gag gag atc ctg gac gcc ttc ctc ccg tag                1143
Asp Gln Val Glu Glu Ile Leu Asp Ala Phe Leu Pro
    370                 375                 380

<210> SEQ ID NO 28
<211> LENGTH: 380
<212> TYPE: PRT
<213> ORGANISM: Thermus thermophilus

<400> SEQUENCE: 28

Met Ser Glu Ile Ala Leu Glu Ala Trp Gly His Glu Ala Leu Leu
  1               5                  10                  15

Leu Lys Pro Pro Arg Ser Pro Leu Ser Ile Pro Pro Lys Pro Arg
                 20                  25                  30

Thr Ala Val Leu Phe Pro Arg Arg Glu Gly Phe Tyr Thr Glu Leu Gly
                 35                  40                  45

Gly Tyr Leu Pro Glu Val Arg Leu Arg Phe Glu Thr Tyr Gly Thr Leu
     50                  55                      60

Ser Arg Arg Arg Asp Asn Ala Val Leu Val Phe His Ala Leu Thr Gly
 65                  70                      75                  80

Ser Ala His Leu Ala Gly Thr Tyr Asp Glu Glu Thr Phe Arg Ser Leu
             85                      90                      95

Ser Pro Leu Glu Gln Ala Phe Gly Arg Glu Gly Trp Trp Asp Ser Leu
            100                 105                 110

Val Gly Pro Gly Arg Ile Leu Asp Pro Ala Leu Tyr Tyr Val Val Ser
        115                 120                 125

Ala Asn His Leu Gly Ser Cys Tyr Gly Ser Thr Gly Pro Leu Ser Leu
    130                 135                 140

Asp Pro His Thr Gly Arg Pro Tyr Gly Arg Asp Phe Pro Pro Leu Thr
145                 150                 155                 160

Ile Arg Asp Leu Ala Arg Ala Gln Ala Arg Leu Leu Asp His Leu Gly
                165                 170                 175

Val Glu Lys Ala Ile Val Ile Gly Gly Ser Leu Gly Gly Met Val Ala
            180                 185                 190

Leu Glu Phe Ala Leu Met Tyr Pro Glu Arg Val Lys Lys Leu Val Val
        195                 200                 205

Leu Ala Ala Pro Ala Arg His Gly Pro Trp Ala Arg Ala Phe Asn His
    210                 215                 220

Leu Ser Arg Gln Ala Ile Leu Gln Asp Pro Glu Tyr Gln Lys Gly Asn
225                 230                 235                 240

Pro Ala Pro Lys Gly Met Ala Leu Ala Arg Gly Ile Ala Met Met Ser
                245                 250                 255

Tyr Arg Ala Pro Glu Gly Phe Glu Ala Arg Trp Gly Ala Glu Pro Glu
            260                 265                 270

Leu Gly Glu Ile His Leu Asp Tyr Gln Gly Glu Lys Phe Leu Arg Arg
        275                 280                 285

Phe His Ala Glu Ser Tyr Leu Val Leu Ser Arg Ala Met Asp Asn His
    290                 295                 300

Asp Val Gly Arg Gly Arg Gly Val Glu Glu Ala Leu Lys Arg Leu
305                 310                 315                 320

Arg Ala Ile Pro Ser Leu Phe Val Gly Ile Asp Thr Asp Leu Leu Tyr
                325                 330                 335

Pro Ala Trp Glu Val Arg Gln Ala Ala Lys Ala Ala Gly Ala Arg Tyr

```
                     340                 345                 350
Arg Glu Ile Lys Ser Pro His Gly His Asp Ala Phe Leu Ile Glu Thr
            355                 360                 365

Asp Gln Val Glu Glu Ile Leu Asp Ala Phe Leu Pro
        370                 375                 380

<210> SEQ ID NO 29
<211> LENGTH: 1005
<212> TYPE: DNA
<213> ORGANISM: Deinococcus radiodurans
<220> FEATURE:
<221> NAME/KEY: CDS
<222> LOCATION: (1)..(1002)
<223> OTHER INFORMATION: RDR01287

<400> SEQUENCE: 29 gtg acc gcc gtg ctc gcg ggc cac gcc tct gcc ctg ctg ctg acc gaa        48
Val Thr Ala Val Leu Ala Gly His Ala Ser Ala Leu Leu Leu Thr Glu
 1               5                  10                  15 gaa ccc gac tgt tcg ggg ccg cag acg gtc gtt ctc ttc cgg cgt gag        96
Glu Pro Asp Cys Ser Gly Pro Gln Thr Val Val Leu Phe Arg Arg Glu
             20                  25                  30 ccg ctg ctg ctc gac tgc gga cgg gcg ctg agc gac gtg cgg gtg gcc       144
Pro Leu Leu Leu Asp Cys Gly Arg Ala Leu Ser Asp Val Arg Val Ala
         35                  40                  45 ttt cac acc tac ggc acg ccg cgc gcc gac gcc acg ctg gtg ctg cac       192
Phe His Thr Tyr Gly Thr Pro Arg Ala Asp Ala Thr Leu Val Leu His
     50                  55                  60 gcc ctg acc ggc gac agc gcg gtg cac gag tgg tgg ccc gac ttt ctg       240
Ala Leu Thr Gly Asp Ser Ala Val His Glu Trp Trp Pro Asp Phe Leu
 65                  70                  75                  80 ggc gcg ggc cgg cca ctg gac ccg gca gac gac tac gtg gtg tgc gcc       288
Gly Ala Gly Arg Pro Leu Asp Pro Ala Asp Asp Tyr Val Val Cys Ala
                 85                  90                  95 aac gtc ctc ggc ggg tgc gcc ggc acg acg agc gcc gct gaa ctc gcc       336
Asn Val Leu Gly Gly Cys Ala Gly Thr Thr Ser Ala Ala Glu Leu Ala
            100                 105                 110 gcc acc tgt tcc gga ccg gtg ccg ctc agc ctg cgc gac atg gcc cgg       384
Ala Thr Cys Ser Gly Pro Val Pro Leu Ser Leu Arg Asp Met Ala Arg
        115                 120                 125 gtg ggg cgc gcc ctg ctg gat tct ctc ggc gtg cga cgg gtg cgg gtc       432
Val Gly Arg Ala Leu Leu Asp Ser Leu Gly Val Arg Arg Val Arg Val
    130                 135                 140 atc ggc gcg agc atg ggc ggg atg ctc gcc tac gcc tgg ctg ctg gag       480
Ile Gly Ala Ser Met Gly Gly Met Leu Ala Tyr Ala Trp Leu Leu Glu
145                 150                 155                 160 tgc ccc gac ctg gtg gaa aag gcc gtg att ata gga gcc ccg gcg cgg       528
Cys Pro Asp Leu Val Glu Lys Ala Val Ile Ile Gly Ala Pro Ala Arg
                165                 170                 175 cac tcg ccc tgg gct att gga ctg aac acg gcg gcc cgc agc gcc att       576
His Ser Pro Trp Ala Ile Gly Leu Asn Thr Ala Ala Arg Ser Ala Ile
            180                 185                 190 gcc ctc gct ccc ggc ggc gag ggg ctg aag gtg gcg cgc cag att gcc       624
Ala Leu Ala Pro Gly Gly Glu Gly Leu Lys Val Ala Arg Gln Ile Ala
        195                 200                 205 atg ctc agt tac cgc agc ccc gaa agc cta agc cgc acg cag gcg ggg       672
Met Leu Ser Tyr Arg Ser Pro Glu Ser Leu Ser Arg Thr Gln Ala Gly
    210                 215                 220 cag cgc gtg ccg ggg gtg ccc gcc gtt acg tct tac ctg cac tac caa       720
Gln Arg Val Pro Gly Val Pro Ala Val Thr Ser Tyr Leu His Tyr Gln
225                 230                 235                 240
```

```
ggc gaa aaa ctc gcc gcc cgc ttc gac gag cag acc tac tgc gcc ctc         768
Gly Glu Lys Leu Ala Ala Arg Phe Asp Glu Gln Thr Tyr Cys Ala Leu
                245                 250                 255 acc tgg gcg atg gac gcc ttt cag ccg agc agc gcc gac ctc aaa gcg         816
Thr Trp Ala Met Asp Ala Phe Gln Pro Ser Ser Ala Asp Leu Lys Ala
            260                 265                 270 gtg cgc gcg ccg gta ctc gtc gtc ggc atc tcc agc gat ctg ctc tac         864
Val Arg Ala Pro Val Leu Val Val Gly Ile Ser Ser Asp Leu Leu Tyr
        275                 280                 285 ccc gcc gcc gag gtc cgc gcc tgc gcc gcc gag ctt ccc cac gcc gac         912
Pro Ala Ala Glu Val Arg Ala Cys Ala Ala Glu Leu Pro His Ala Asp
    290                 295                 300 tac tgg gaa ctg ggc agc att cac ggc cac gac gcc ttt ttg atg gac         960
Tyr Trp Glu Leu Gly Ser Ile His Gly His Asp Ala Phe Leu Met Asp
305                 310                 315                 320 cca cag gac ttg ccg gag cgg gtg ggg gcg ttt ctc agg agt                1002
Pro Gln Asp Leu Pro Glu Arg Val Gly Ala Phe Leu Arg Ser
                325                 330 tga                                                                    1005

<210> SEQ ID NO 30
<211> LENGTH: 334
<212> TYPE: PRT
<213> ORGANISM: Deinococcus radiodurans

<400> SEQUENCE: 30

Val Thr Ala Val Leu Ala Gly His Ala Ser Ala Leu Leu Leu Thr Glu
  1               5                  10                  15

Glu Pro Asp Cys Ser Gly Pro Gln Thr Val Val Leu Phe Arg Arg Glu
                 20                  25                  30

Pro Leu Leu Leu Asp Cys Gly Arg Ala Leu Ser Asp Val Arg Val Ala
             35                  40                  45

Phe His Thr Tyr Gly Thr Pro Arg Ala Asp Ala Thr Leu Val Leu His
         50                  55                  60

Ala Leu Thr Gly Asp Ser Ala Val His Glu Trp Trp Pro Asp Phe Leu
 65                  70                  75                  80

Gly Ala Gly Arg Pro Leu Asp Pro Ala Asp Tyr Val Val Cys Ala
                 85                  90                  95

Asn Val Leu Gly Gly Cys Ala Gly Thr Thr Ser Ala Ala Glu Leu Ala
                100                 105                 110

Ala Thr Cys Ser Gly Pro Val Pro Leu Ser Leu Arg Asp Met Ala Arg
            115                 120                 125

Val Gly Arg Ala Leu Leu Asp Ser Leu Gly Val Arg Arg Val Arg Val
        130                 135                 140

Ile Gly Ala Ser Met Gly Gly Met Leu Ala Tyr Ala Trp Leu Leu Glu
145                 150                 155                 160

Cys Pro Asp Leu Val Glu Lys Ala Val Ile Ile Gly Ala Pro Ala Arg
                165                 170                 175

His Ser Pro Trp Ala Ile Gly Leu Asn Thr Ala Ala Arg Ser Ala Ile
            180                 185                 190

Ala Leu Ala Pro Gly Gly Glu Gly Leu Lys Val Ala Arg Gln Ile Ala
        195                 200                 205

Met Leu Ser Tyr Arg Ser Pro Glu Ser Leu Ser Arg Thr Gln Ala Gly
    210                 215                 220

Gln Arg Val Pro Gly Val Pro Ala Val Thr Ser Tyr Leu His Tyr Gln
225                 230                 235                 240
```

```
Gly Glu Lys Leu Ala Ala Arg Phe Asp Glu Gln Thr Tyr Cys Ala Leu
            245                 250                 255

Thr Trp Ala Met Asp Ala Phe Gln Pro Ser Ser Ala Asp Leu Lys Ala
            260                 265                 270

Val Arg Ala Pro Val Leu Val Gly Ile Ser Ser Asp Leu Leu Tyr
            275                 280                 285

Pro Ala Ala Glu Val Arg Ala Cys Ala Ala Glu Leu Pro His Ala Asp
            290                 295                 300

Tyr Trp Glu Leu Gly Ser Ile His Gly His Asp Ala Phe Leu Met Asp
305                 310                 315                 320

Pro Gln Asp Leu Pro Glu Arg Val Gly Ala Phe Leu Arg Ser
            325                 330
```

<210> SEQ ID NO 31
<211> LENGTH: 1461
<212> TYPE: DNA
<213> ORGANISM: Saccharomyces cerevisiae
<220> FEATURE:
<221> NAME/KEY: CDS
<222> LOCATION: (1)..(1458)
<223> OTHER INFORMATION: RSC08123

<400> SEQUENCE: 31

```
atg tcg cat act tta aaa tcg aaa acg ctc caa gag ctg gac att gag      48
Met Ser His Thr Leu Lys Ser Lys Thr Leu Gln Glu Leu Asp Ile Glu
  1               5                  10                  15 gag att aag gaa act aac cca ttg ctc aaa cta gtt caa ggg cag agg      96
Glu Ile Lys Glu Thr Asn Pro Leu Leu Lys Leu Val Gln Gly Gln Arg
             20                  25                  30 att gtt caa gtt ccg gaa cta gtg ctt gag tct ggc gtg gtc ata aat     144
Ile Val Gln Val Pro Glu Leu Val Leu Glu Ser Gly Val Val Ile Asn
         35                  40                  45 aat ttc cct att gct tat aag acg tgg ggt aca ctg aat gaa gct ggt     192
Asn Phe Pro Ile Ala Tyr Lys Thr Trp Gly Thr Leu Asn Glu Ala Gly
     50                  55                  60 gat aat gtt ctg gta att tgt cat gcc ttg act ggg tcc gca gat gtt     240
Asp Asn Val Leu Val Ile Cys His Ala Leu Thr Gly Ser Ala Asp Val
 65                  70                  75                  80 gct gac tgg tgg ggc cct ctt ctg ggt aac gac tta gca ttc gac cca     288
Ala Asp Trp Trp Gly Pro Leu Leu Gly Asn Asp Leu Ala Phe Asp Pro
                 85                  90                  95 tca agg ttt ttt atc ata tgt tta aac tct atg ggc tct cca tat ggg     336
Ser Arg Phe Phe Ile Ile Cys Leu Asn Ser Met Gly Ser Pro Tyr Gly
            100                 105                 110 tct ttt tcg cca tta acg ata aat gag gag acg ggc gtt aga tat gga     384
Ser Phe Ser Pro Leu Thr Ile Asn Glu Glu Thr Gly Val Arg Tyr Gly
        115                 120                 125 ccc gaa ttc cca tta tgt act gtg cgc gat gac gtt aga gct cac aga     432
Pro Glu Phe Pro Leu Cys Thr Val Arg Asp Asp Val Arg Ala His Arg
    130                 135                 140 att gtt ctg gat tct ctg gga gta aag tca ata gcc tgt gtt att ggt     480
Ile Val Leu Asp Ser Leu Gly Val Lys Ser Ile Ala Cys Val Ile Gly
145                 150                 155                 160 ggc tct atg ggg ggg atg ctg agt ttg gaa tgg gct gcc atg tat ggt     528
Gly Ser Met Gly Gly Met Leu Ser Leu Glu Trp Ala Ala Met Tyr Gly
                165                 170                 175 aag gaa tat gtg aag aat atg gtt gct ctg gcg aca tca gca aga cat     576
Lys Glu Tyr Val Lys Asn Met Val Ala Leu Ala Thr Ser Ala Arg His
            180                 185                 190
```

```
tct gcc tgg tgc ata tcg tgg tct gag gct caa aga caa tcg att tac    624
Ser Ala Trp Cys Ile Ser Trp Ser Glu Ala Gln Arg Gln Ser Ile Tyr
        195                 200                 205 tca gat ccc aac tac ttg gac ggg tac tat ccg gta gag gag caa cct    672
Ser Asp Pro Asn Tyr Leu Asp Gly Tyr Tyr Pro Val Glu Glu Gln Pro
210                 215                 220 gtg gcc gga cta tcg gct gca cgt atg tct gca ttg ttg acg tac agg    720
Val Ala Gly Leu Ser Ala Ala Arg Met Ser Ala Leu Leu Thr Tyr Arg
225                 230                 235                 240 aca aga aac agt ttc gag aac aaa ttc tcc aga aga tct cct tca ata    768
Thr Arg Asn Ser Phe Glu Asn Lys Phe Ser Arg Arg Ser Pro Ser Ile
                245                 250                 255 gca caa caa caa aaa gct caa agg gag gag aca cgc aaa cca tct act    816
Ala Gln Gln Gln Lys Ala Gln Arg Glu Glu Thr Arg Lys Pro Ser Thr
            260                 265                 270 gtc agc gaa cac tcc cta caa atc cac aat gat ggg tat aaa aca aaa    864
Val Ser Glu His Ser Leu Gln Ile His Asn Asp Gly Tyr Lys Thr Lys
        275                 280                 285 gcc agc act gcc atc gct ggc att tct ggg caa aaa ggt caa agc gtg    912
Ala Ser Thr Ala Ile Ala Gly Ile Ser Gly Gln Lys Gly Gln Ser Val
    290                 295                 300 gtg tcc acc gca tct tct tcg gat tca ttg aat tct tca aca tcg atg    960
Val Ser Thr Ala Ser Ser Ser Asp Ser Leu Asn Ser Ser Thr Ser Met
305                 310                 315                 320 act tcg gta agt tct gta acg ggt gaa gtg aag gac ata aag cct gcg   1008
Thr Ser Val Ser Ser Val Thr Gly Glu Val Lys Asp Ile Lys Pro Ala
                325                 330                 335 cag acg tat ttt tct gca caa agt tac ttg agg tac cag ggc aca aag   1056
Gln Thr Tyr Phe Ser Ala Gln Ser Tyr Leu Arg Tyr Gln Gly Thr Lys
            340                 345                 350 ttc atc aat agg ttc gac gcc aat tgt tac att gcc atc aca cgt aaa   1104
Phe Ile Asn Arg Phe Asp Ala Asn Cys Tyr Ile Ala Ile Thr Arg Lys
        355                 360                 365 ctg gat acg cac gat ttg gca aga gac aga gta gat gac atc act gag   1152
Leu Asp Thr His Asp Leu Ala Arg Asp Arg Val Asp Asp Ile Thr Glu
    370                 375                 380 gtc ctt tct acc atc caa caa cca tcc ctg atc atc ggt atc caa tct   1200
Val Leu Ser Thr Ile Gln Gln Pro Ser Leu Ile Ile Gly Ile Gln Ser
385                 390                 395                 400 gat gga ctg ttc aca tat tca gaa caa gaa ttt ttg gct gag cac ata   1248
Asp Gly Leu Phe Thr Tyr Ser Glu Gln Glu Phe Leu Ala Glu His Ile
                405                 410                 415 ccg aag tcg caa tta gaa aaa att gaa tct ccc gaa ggc cac gat gcc   1296
Pro Lys Ser Gln Leu Glu Lys Ile Glu Ser Pro Glu Gly His Asp Ala
            420                 425                 430 ttc cta ttg gag ttt aag ctg ata aac aaa ctg ata gta caa ttt tta   1344
Phe Leu Leu Glu Phe Lys Leu Ile Asn Lys Leu Ile Val Gln Phe Leu
        435                 440                 445 aaa acc aac tgc aag gcc att acc gat gcc gct cca aga gct tgg gga   1392
Lys Thr Asn Cys Lys Ala Ile Thr Asp Ala Ala Pro Arg Ala Trp Gly
    450                 455                 460 ggt gac gtt ggt aac gat gaa acg aag acg tct gtc ttt ggt gag gcc   1440
Gly Asp Val Gly Asn Asp Glu Thr Lys Thr Ser Val Phe Gly Glu Ala
465                 470                 475                 480 gaa gaa gtt acc aac tgg tag                                        1461
Glu Glu Val Thr Asn Trp
                485
```

<210> SEQ ID NO 32
<211> LENGTH: 486

<212> TYPE: PRT
<213> ORGANISM: Saccharomyces cerevisiae

<400> SEQUENCE: 32

```
Met Ser His Thr Leu Lys Ser Lys Thr Leu Gln Glu Leu Asp Ile Glu
1               5                   10                  15

Glu Ile Lys Glu Thr Asn Pro Leu Leu Lys Leu Val Gln Gly Gln Arg
            20                  25                  30

Ile Val Gln Val Pro Glu Leu Val Leu Glu Ser Gly Val Val Ile Asn
        35                  40                  45

Asn Phe Pro Ile Ala Tyr Lys Thr Trp Gly Thr Leu Asn Glu Ala Gly
    50                  55                  60

Asp Asn Val Leu Val Ile Cys His Ala Leu Thr Gly Ser Ala Asp Val
65                  70                  75                  80

Ala Asp Trp Trp Gly Pro Leu Leu Gly Asn Asp Leu Ala Phe Asp Pro
                85                  90                  95

Ser Arg Phe Phe Ile Ile Cys Leu Asn Ser Met Gly Ser Pro Tyr Gly
            100                 105                 110

Ser Phe Ser Pro Leu Thr Ile Asn Glu Glu Thr Gly Val Arg Tyr Gly
        115                 120                 125

Pro Glu Phe Pro Leu Cys Thr Val Arg Asp Asp Val Arg Ala His Arg
    130                 135                 140

Ile Val Leu Asp Ser Leu Gly Val Lys Ser Ile Ala Cys Val Ile Gly
145                 150                 155                 160

Gly Ser Met Gly Gly Met Leu Ser Leu Glu Trp Ala Ala Met Tyr Gly
                165                 170                 175

Lys Glu Tyr Val Lys Asn Met Val Ala Leu Ala Thr Ser Ala Arg His
            180                 185                 190

Ser Ala Trp Cys Ile Ser Trp Ser Glu Ala Gln Arg Gln Ser Ile Tyr
        195                 200                 205

Ser Asp Pro Asn Tyr Leu Asp Gly Tyr Tyr Pro Val Glu Glu Gln Pro
    210                 215                 220

Val Ala Gly Leu Ser Ala Ala Arg Met Ser Ala Leu Leu Thr Tyr Arg
225                 230                 235                 240

Thr Arg Asn Ser Phe Glu Asn Lys Phe Ser Arg Arg Ser Pro Ser Ile
                245                 250                 255

Ala Gln Gln Gln Lys Ala Gln Arg Glu Glu Thr Arg Lys Pro Ser Thr
            260                 265                 270

Val Ser Glu His Ser Leu Gln Ile His Asn Asp Gly Tyr Lys Thr Lys
        275                 280                 285

Ala Ser Thr Ala Ile Ala Gly Ile Ser Gly Gln Lys Gly Gln Ser Val
    290                 295                 300

Val Ser Thr Ala Ser Ser Ser Asp Ser Leu Asn Ser Ser Thr Ser Met
305                 310                 315                 320

Thr Ser Val Ser Ser Val Thr Gly Glu Val Lys Asp Ile Lys Pro Ala
                325                 330                 335

Gln Thr Tyr Phe Ser Ala Gln Ser Tyr Leu Arg Tyr Gln Gly Thr Lys
            340                 345                 350

Phe Ile Asn Arg Phe Asp Ala Asn Cys Tyr Ile Ala Ile Thr Arg Lys
        355                 360                 365

Leu Asp Thr His Asp Leu Ala Arg Asp Arg Val Asp Ile Thr Glu
    370                 375                 380

Val Leu Ser Thr Ile Gln Gln Pro Ser Leu Ile Ile Gly Ile Gln Ser
385                 390                 395                 400
```

```
Asp Gly Leu Phe Thr Tyr Ser Glu Gln Glu Phe Leu Ala Glu His Ile
                405                 410                 415

Pro Lys Ser Gln Leu Glu Lys Ile Glu Ser Pro Glu Gly His Asp Ala
            420                 425                 430

Phe Leu Leu Glu Phe Lys Leu Ile Asn Lys Leu Ile Val Gln Phe Leu
        435                 440                 445

Lys Thr Asn Cys Lys Ala Ile Thr Asp Ala Ala Pro Arg Ala Trp Gly
    450                 455                 460

Gly Asp Val Gly Asn Asp Glu Thr Lys Thr Ser Val Phe Gly Glu Ala
465                 470                 475                 480

Glu Glu Val Thr Asn Trp
                485

<210> SEQ ID NO 33
<211> LENGTH: 1470
<212> TYPE: DNA
<213> ORGANISM: Schizosaccharomyces pombe
<220> FEATURE:
<221> NAME/KEY: CDS
<222> LOCATION: (1)..(1467)
<223> OTHER INFORMATION: RSO01936

<400> SEQUENCE: 33 atg gaa tct caa tct ccg att gaa tca att gtc ttt act gac tcc tgt       48
Met Glu Ser Gln Ser Pro Ile Glu Ser Ile Val Phe Thr Asp Ser Cys
  1               5                  10                  15 cat ccg tct cag caa gaa aat aaa ttt gtt cag ctt att tca gat caa       96
His Pro Ser Gln Gln Glu Asn Lys Phe Val Gln Leu Ile Ser Asp Gln
             20                  25                  30 aaa att gca att gtt ccc aaa ttt acg ttg gag tgt ggc gac atc ctt      144
Lys Ile Ala Ile Val Pro Lys Phe Thr Leu Glu Cys Gly Asp Ile Leu
         35                  40                  45 tac gat gtt ccc gtt gcc ttc aag act tgg ggt act ttg aat aaa gaa      192
Tyr Asp Val Pro Val Ala Phe Lys Thr Trp Gly Thr Leu Asn Lys Glu
     50                  55                  60 gga aac aat tgt ctt ctt ctt tgt cat gct tta agt ggt tct gct gat      240
Gly Asn Asn Cys Leu Leu Leu Cys His Ala Leu Ser Gly Ser Ala Asp
 65                  70                  75                  80 gct gga gat tgg tgg ggt cct tta ctc ggt cct ggt cgt gcg ttt gat      288
Ala Gly Asp Trp Trp Gly Pro Leu Leu Gly Pro Gly Arg Ala Phe Asp
                 85                  90                  95 cca tca cat ttc ttt atc gta tgc ctt aat tct ctt ggt agc cca tac      336
Pro Ser His Phe Phe Ile Val Cys Leu Asn Ser Leu Gly Ser Pro Tyr
            100                 105                 110 gga agc gcc tct cct gtt aca tgg aac gct gag act cat agt gtt tat      384
Gly Ser Ala Ser Pro Val Thr Trp Asn Ala Glu Thr His Ser Val Tyr
        115                 120                 125 ggg cca gaa ttt cct tta gca acc ata cgt gat gat gta aac atc cat      432
Gly Pro Glu Phe Pro Leu Ala Thr Ile Arg Asp Asp Val Asn Ile His
    130                 135                 140 aaa ctt att tta caa aga ttg ggt gta aag caa att gct atg gca gta      480
Lys Leu Ile Leu Gln Arg Leu Gly Val Lys Gln Ile Ala Met Ala Val
145                 150                 155                 160 ggt ggc tcc atg ggt ggt atg ctg gtt ttg gag tgg gca ttt gat aag      528
Gly Gly Ser Met Gly Gly Met Leu Val Leu Glu Trp Ala Phe Asp Lys
                165                 170                 175 gaa ttt gtg cga tca att gtt ccc att tct acc tct ctt cgt cat tcc      576
Glu Phe Val Arg Ser Ile Val Pro Ile Ser Thr Ser Leu Arg His Ser
            180                 185                 190
```

| | | | | | | | | | | | | | | | | |
|---|---|---|---|---|---|---|---|---|---|---|---|---|---|---|---|---|
| gcg | tgg | tgc | att | agc | tgg | tct | gaa | gcg | caa | cgc | cag | agt | ata | tat | tct | 624 |
| Ala | Trp | Cys | Ile | Ser | Trp | Ser | Glu | Ala | Gln | Arg | Gln | Ser | Ile | Tyr | Ser | |
| | | 195 | | | | | 200 | | | | | 205 | | | | |
| gac | cct | aag | ttt | aat | gat | gga | tac | tac | ggc | ata | gac | gat | cag | cct | gta | 672 |
| Asp | Pro | Lys | Phe | Asn | Asp | Gly | Tyr | Tyr | Gly | Ile | Asp | Asp | Gln | Pro | Val | |
| | 210 | | | | | 215 | | | | | 220 | | | | | |
| agt | ggc | ctt | gga | gct | gct | cgt | atg | tct | gcc | ttg | ttg | aca | tat | cgc | tcc | 720 |
| Ser | Gly | Leu | Gly | Ala | Ala | Arg | Met | Ser | Ala | Leu | Leu | Thr | Tyr | Arg | Ser | |
| 225 | | | | | 230 | | | | | 235 | | | | | 240 | |
| aaa | tgt | tct | ttc | gaa | cgt | cgc | ttt | gcc | cgt | act | gtt | cct | gat | gcg | tct | 768 |
| Lys | Cys | Ser | Phe | Glu | Arg | Arg | Phe | Ala | Arg | Thr | Val | Pro | Asp | Ala | Ser | |
| | | | | 245 | | | | | 250 | | | | | 255 | | |
| cgt | cac | ccc | tat | cca | gat | cgt | tta | ccc | act | cct | ctc | acg | ccc | agt | aat | 816 |
| Arg | His | Pro | Tyr | Pro | Asp | Arg | Leu | Pro | Thr | Pro | Leu | Thr | Pro | Ser | Asn | |
| | | | 260 | | | | | 265 | | | | | 270 | | | |
| gca | cat | tgg | gtc | gtt | cac | aac | gaa | gga | aac | cgt | aat | cgc | cgt | gaa | cga | 864 |
| Ala | His | Trp | Val | Val | His | Asn | Glu | Gly | Asn | Arg | Asn | Arg | Arg | Glu | Arg | |
| | | 275 | | | | | 280 | | | | | 285 | | | | |
| cct | tgt | cga | tcc | aat | gga | tca | tca | cct | act | tct | gaa | agt | gct | tta | aat | 912 |
| Pro | Cys | Arg | Ser | Asn | Gly | Ser | Ser | Pro | Thr | Ser | Glu | Ser | Ala | Leu | Asn | |
| | 290 | | | | | 295 | | | | | 300 | | | | | |
| tcc | ccc | gcc | tct | tct | gtc | tcg | tct | tta | cct | tct | tta | ggt | gcc | tct | cag | 960 |
| Ser | Pro | Ala | Ser | Ser | Val | Ser | Ser | Leu | Pro | Ser | Leu | Gly | Ala | Ser | Gln | |
| 305 | | | | | 310 | | | | | 315 | | | | | 320 | |
| act | aca | gac | agt | tct | tcc | ctt | aac | cag | agt | tcg | tta | tta | aga | cgt | cct | 1008 |
| Thr | Thr | Asp | Ser | Ser | Ser | Leu | Asn | Gln | Ser | Ser | Leu | Leu | Arg | Arg | Pro | |
| | | | | 325 | | | | | 330 | | | | | 335 | | |
| gct | aat | act | tac | ttc | tct | gcg | caa | tcg | tat | tta | cgt | tac | caa | gcg | aag | 1056 |
| Ala | Asn | Thr | Tyr | Phe | Ser | Ala | Gln | Ser | Tyr | Leu | Arg | Tyr | Gln | Ala | Lys | |
| | | | 340 | | | | | 345 | | | | | 350 | | | |
| aag | ttt | gta | agt | cgc | ttt | gat | gct | aat | tgt | tac | att | tcg | att | act | aaa | 1104 |
| Lys | Phe | Val | Ser | Arg | Phe | Asp | Ala | Asn | Cys | Tyr | Ile | Ser | Ile | Thr | Lys | |
| | | 355 | | | | | 360 | | | | | 365 | | | | |
| aag | ttg | gac | acc | cat | gat | att | act | cgt | gga | cgc | ggt | tca | gac | tct | cct | 1152 |
| Lys | Leu | Asp | Thr | His | Asp | Ile | Thr | Arg | Gly | Arg | Gly | Ser | Asp | Ser | Pro | |
| | 370 | | | | | 375 | | | | | 380 | | | | | |
| aag | gaa | gtc | atg | aag | gat | ttg | tct | tta | ccc | gta | ctc | gta | ctc | ggt | att | 1200 |
| Lys | Glu | Val | Met | Lys | Asp | Leu | Ser | Leu | Pro | Val | Leu | Val | Leu | Gly | Ile | |
| 385 | | | | | 390 | | | | | 395 | | | | | 400 | |
| gaa | agc | gat | ggt | ctt | ttc | aca | ttt | gac | gaa | caa | gtt | gaa | att | gcc | aaa | 1248 |
| Glu | Ser | Asp | Gly | Leu | Phe | Thr | Phe | Asp | Glu | Gln | Val | Glu | Ile | Ala | Lys | |
| | | | | 405 | | | | | 410 | | | | | 415 | | |
| tct | ttt | ccc | aat | gct | acc | ttg | gaa | aaa | att | att | tcg | gcc | gaa | ggc | cac | 1296 |
| Ser | Phe | Pro | Asn | Ala | Thr | Leu | Glu | Lys | Ile | Ile | Ser | Ala | Glu | Gly | His | |
| | | | 420 | | | | | 425 | | | | | 430 | | | |
| gac | ggt | ttt | ttg | ctt | gag | ttt | act | caa | gta | aac | tca | cat | att | caa | aaa | 1344 |
| Asp | Gly | Phe | Leu | Leu | Glu | Phe | Thr | Gln | Val | Asn | Ser | His | Ile | Gln | Lys | |
| | | 435 | | | | | 440 | | | | | 445 | | | | |
| ttc | caa | aag | gaa | cat | tta | att | gat | atc | atg | tct | caa | act | aat | tcc | ttt | 1392 |
| Phe | Gln | Lys | Glu | His | Leu | Ile | Asp | Ile | Met | Ser | Gln | Thr | Asn | Ser | Phe | |
| | 450 | | | | | 455 | | | | | 460 | | | | | |
| gag | cga | ctt | gat | tcc | caa | gtt | aat | gat | acc | aac | cgc | gaa | agc | gtt | ttt | 1440 |
| Glu | Arg | Leu | Asp | Ser | Gln | Val | Asn | Asp | Thr | Asn | Arg | Glu | Ser | Val | Phe | |
| 465 | | | | | 470 | | | | | 475 | | | | | 480 | |
| gga | gaa | atg | gaa | gac | ata | acc | tcc | tgg | taa | | | | | | | 1470 |
| Gly | Glu | Met | Glu | Asp | Ile | Thr | Ser | Trp | | | | | | | | |
| | | | | 485 | | | | | | | | | | | | |

<210> SEQ ID NO 34
<211> LENGTH: 489

```
<212> TYPE: PRT
<213> ORGANISM: Schizosaccharomyces pombe

<400> SEQUENCE: 34
```

| | | | | | | | | | | | | | | | |
|---|---|---|---|---|---|---|---|---|---|---|---|---|---|---|---|
| Met | Glu | Ser | Gln | Ser | Pro | Ile | Glu | Ser | Ile | Val | Phe | Thr | Asp | Ser | Cys |
| 1 | | | | 5 | | | | | 10 | | | | | 15 | |
| His | Pro | Ser | Gln | Gln | Glu | Asn | Lys | Phe | Val | Gln | Leu | Ile | Ser | Asp | Gln |
| | | | 20 | | | | | 25 | | | | | 30 | | |
| Lys | Ile | Ala | Ile | Val | Pro | Lys | Phe | Thr | Leu | Glu | Cys | Gly | Asp | Ile | Leu |
| | | 35 | | | | | 40 | | | | | 45 | | | |
| Tyr | Asp | Val | Pro | Val | Ala | Phe | Lys | Thr | Trp | Gly | Thr | Leu | Asn | Lys | Glu |
| | 50 | | | | | 55 | | | | | 60 | | | | |
| Gly | Asn | Asn | Cys | Leu | Leu | Cys | His | Ala | Leu | Ser | Gly | Ser | Ala | Asp |
| 65 | | | | 70 | | | | | 75 | | | | | 80 |
| Ala | Gly | Asp | Trp | Trp | Gly | Pro | Leu | Leu | Gly | Pro | Gly | Arg | Ala | Phe | Asp |
| | | | | 85 | | | | | 90 | | | | | 95 | |
| Pro | Ser | His | Phe | Phe | Ile | Val | Cys | Leu | Asn | Ser | Leu | Gly | Ser | Pro | Tyr |
| | | | 100 | | | | | 105 | | | | | 110 | | |
| Gly | Ser | Ala | Ser | Pro | Val | Thr | Trp | Asn | Ala | Glu | Thr | His | Ser | Val | Tyr |
| | | 115 | | | | | 120 | | | | | 125 | | | |
| Gly | Pro | Glu | Phe | Pro | Leu | Ala | Thr | Ile | Arg | Asp | Asp | Val | Asn | Ile | His |
| | 130 | | | | | 135 | | | | | 140 | | | | |
| Lys | Leu | Ile | Leu | Gln | Arg | Leu | Gly | Val | Lys | Gln | Ile | Ala | Met | Ala | Val |
| 145 | | | | 150 | | | | | 155 | | | | | 160 | |
| Gly | Gly | Ser | Met | Gly | Gly | Met | Leu | Val | Leu | Glu | Trp | Ala | Phe | Asp | Lys |
| | | | 165 | | | | | 170 | | | | | 175 | | |
| Glu | Phe | Val | Arg | Ser | Ile | Val | Pro | Ile | Ser | Thr | Ser | Leu | Arg | His | Ser |
| | | | 180 | | | | | 185 | | | | | 190 | | |
| Ala | Trp | Cys | Ile | Ser | Trp | Ser | Glu | Ala | Gln | Arg | Gln | Ser | Ile | Tyr | Ser |
| | | 195 | | | | | 200 | | | | | 205 | | | |
| Asp | Pro | Lys | Phe | Asn | Asp | Gly | Tyr | Tyr | Gly | Ile | Asp | Asp | Gln | Pro | Val |
| | 210 | | | | | 215 | | | | | 220 | | | | |
| Ser | Gly | Leu | Gly | Ala | Ala | Arg | Met | Ser | Ala | Leu | Leu | Thr | Tyr | Arg | Ser |
| 225 | | | | 230 | | | | | 235 | | | | | 240 | |
| Lys | Cys | Ser | Phe | Glu | Arg | Arg | Phe | Ala | Arg | Thr | Val | Pro | Asp | Ala | Ser |
| | | | 245 | | | | | 250 | | | | | 255 | | |
| Arg | His | Pro | Tyr | Pro | Asp | Arg | Leu | Pro | Thr | Pro | Leu | Thr | Pro | Ser | Asn |
| | | | 260 | | | | | 265 | | | | | 270 | | |
| Ala | His | Trp | Val | Val | His | Asn | Glu | Gly | Asn | Arg | Asn | Arg | Arg | Glu | Arg |
| | | 275 | | | | | 280 | | | | | 285 | | | |
| Pro | Cys | Arg | Ser | Asn | Gly | Ser | Ser | Pro | Thr | Ser | Glu | Ser | Ala | Leu | Asn |
| | 290 | | | | | 295 | | | | | 300 | | | | |
| Ser | Pro | Ala | Ser | Ser | Val | Ser | Ser | Leu | Pro | Ser | Leu | Gly | Ala | Ser | Gln |
| 305 | | | | 310 | | | | | 315 | | | | | 320 | |
| Thr | Thr | Asp | Ser | Ser | Leu | Asn | Gln | Ser | Ser | Leu | Leu | Arg | Arg | Pro |
| | | | 325 | | | | | 330 | | | | | 335 | |
| Ala | Asn | Thr | Tyr | Phe | Ser | Ala | Gln | Ser | Tyr | Leu | Arg | Tyr | Gln | Ala | Lys |
| | | | 340 | | | | | 345 | | | | | 350 | | |
| Lys | Phe | Val | Ser | Arg | Phe | Asp | Ala | Asn | Cys | Tyr | Ile | Ser | Ile | Thr | Lys |
| | | | 355 | | | | | 360 | | | | | 365 | | |
| Lys | Leu | Asp | Thr | His | Asp | Ile | Thr | Arg | Gly | Arg | Gly | Ser | Asp | Ser | Pro |
| | | | 370 | | | | | 375 | | | | | 380 | | |
| Lys | Glu | Val | Met | Lys | Asp | Leu | Ser | Leu | Pro | Val | Leu | Val | Leu | Gly | Ile |
| 385 | | | | 390 | | | | | 395 | | | | | 400 |

```
Glu Ser Asp Gly Leu Phe Thr Phe Asp Glu Gln Val Glu Ile Ala Lys
                405                 410                 415
Ser Phe Pro Asn Ala Thr Leu Glu Lys Ile Ile Ser Ala Glu Gly His
            420                 425                 430
Asp Gly Phe Leu Leu Glu Phe Thr Gln Val Asn Ser His Ile Gln Lys
        435                 440                 445
Phe Gln Lys Glu His Leu Ile Asp Ile Met Ser Gln Thr Asn Ser Phe
    450                 455                 460
Glu Arg Leu Asp Ser Gln Val Asn Asp Thr Asn Arg Glu Ser Val Phe
465                 470                 475                 480
Gly Glu Met Glu Asp Ile Thr Ser Trp
                485

<210> SEQ ID NO 35
<211> LENGTH: 1113
<212> TYPE: DNA
<213> ORGANISM: Xylella almond
<220> FEATURE:
<221> NAME/KEY: CDS
<222> LOCATION: (1)..(1110)
<223> OTHER INFORMATION: RXFX01562

<400> SEQUENCE: 35 atg acc gaa ttt atc cct ccg ggc agc cta ttc cat gcg ctc tcc tct      48
Met Thr Glu Phe Ile Pro Pro Gly Ser Leu Phe His Ala Leu Ser Ser
  1               5                  10                  15 cca ttt gcg atg aag cgt ggc gga caa ctc cac cac gcc cgc atc gct      96
Pro Phe Ala Met Lys Arg Gly Gly Gln Leu His His Ala Arg Ile Ala
             20                  25                  30 tac gaa aca tgg ggc cgc ctc aat gcc agc gcc acc aat gcc att ctg     144
Tyr Glu Thr Trp Gly Arg Leu Asn Ala Ser Ala Thr Asn Ala Ile Leu
         35                  40                  45 atc atg cct ggc tta tca ccc aat gca cat gcc gca cac cat gac agc     192
Ile Met Pro Gly Leu Ser Pro Asn Ala His Ala Ala His His Asp Ser
     50                  55                  60 aat gct gag cca ggc tgg tgg gag tca atg cta ggt cca ggc aaa ccc     240
Asn Ala Glu Pro Gly Trp Trp Glu Ser Met Leu Gly Pro Gly Lys Pro
 65                  70                  75                  80 atc gac aca gac cgt tgg ttc gtg atc tgt gtc aac tca ctt ggt agc     288
Ile Asp Thr Asp Arg Trp Phe Val Ile Cys Val Asn Ser Leu Gly Ser
                 85                  90                  95 tgc aaa gga tcg act ggc cct gca tcg tac aac ccc atc acg cag gcc     336
Cys Lys Gly Ser Thr Gly Pro Ala Ser Tyr Asn Pro Ile Thr Gln Ala
            100                 105                 110 atg tat cgt ttg gac ttt cca gca ctg tca atc gaa gac ggg gcc aac     384
Met Tyr Arg Leu Asp Phe Pro Ala Leu Ser Ile Glu Asp Gly Ala Asn
        115                 120                 125 tcc gca att gaa gtg gta cat gca ctg ggc atc aag caa ctt gcc agc     432
Ser Ala Ile Glu Val Val His Ala Leu Gly Ile Lys Gln Leu Ala Ser
    130                 135                 140 ctg atc ggc aat tca atg ggc ggc atg acg gca ctg gcc atc ctg ctg     480
Leu Ile Gly Asn Ser Met Gly Gly Met Thr Ala Leu Ala Ile Leu Leu
145                 150                 155                 160 tta cat cca gat ata gcc cgc agc cac atc aac atc tca ggc agc gcg     528
Leu His Pro Asp Ile Ala Arg Ser His Ile Asn Ile Ser Gly Ser Ala
                165                 170                 175 cag gca tta ccg ttt tcc atc gcc att cgc tcg cta caa cgc gag gcg     576
Gln Ala Leu Pro Phe Ser Ile Ala Ile Arg Ser Leu Gln Arg Glu Ala
            180                 185                 190
```

```
atc cgc ctg gac ccc cat tgg agg cag gga gac tac gac gac acc cac      624
Ile Arg Leu Asp Pro His Trp Arg Gln Gly Asp Tyr Asp Asp Thr His
        195                 200                 205 tac ccg gaa tcg ggg cta cgc atc gca cgc aaa ctt ggg gtg atc acc      672
Tyr Pro Glu Ser Gly Leu Arg Ile Ala Arg Lys Leu Gly Val Ile Thr
210                 215                 220 tac cgc tcc gcg ctg gaa tgg gac ggg cgt ttt ggc cgg gta cgc ttg      720
Tyr Arg Ser Ala Leu Glu Trp Asp Gly Arg Phe Gly Arg Val Arg Leu
225                 230                 235                 240 gat tcg gac caa acc aac gac aca cca ttc gga ctg gaa ttc caa att      768
Asp Ser Asp Gln Thr Asn Asp Thr Pro Phe Gly Leu Glu Phe Gln Ile
                245                 250                 255 gaa aac tac ttg gaa agc cat gca cac cgc ttc gtg cac acc ttc gac      816
Glu Asn Tyr Leu Glu Ser His Ala His Arg Phe Val His Thr Phe Asp
            260                 265                 270 cca aac tgc tac ctg tac ctg agc cgc tcc atg gac tgg ttc gac gtg      864
Pro Asn Cys Tyr Leu Tyr Leu Ser Arg Ser Met Asp Trp Phe Asp Val
        275                 280                 285 gcc gag tac gcc aat gga gac att ctt gcc ggg ctg gcc agg atc cga      912
Ala Glu Tyr Ala Asn Gly Asp Ile Leu Ala Gly Leu Ala Arg Ile Arg
    290                 295                 300 atc caa cgc gca ctc gcc atc ggt agc cat acc gac atc ctc ttt cca      960
Ile Gln Arg Ala Leu Ala Ile Gly Ser His Thr Asp Ile Leu Phe Pro
305                 310                 315                 320 ata caa cag caa caa caa att gcc gaa ggg cta cgc cgt ggc ggt aca     1008
Ile Gln Gln Gln Gln Gln Ile Ala Glu Gly Leu Arg Arg Gly Gly Thr
                325                 330                 335 cac gcc acc ttc ctg ggc ctt gac tca ccg cag ggg cat gat gcg ttc     1056
His Ala Thr Phe Leu Gly Leu Asp Ser Pro Gln Gly His Asp Ala Phe
            340                 345                 350 ctt gtg gat atc gca aga ttt ggc cct cca gtg aag gaa ttt ctg gac     1104
Leu Val Asp Ile Ala Arg Phe Gly Pro Pro Val Lys Glu Phe Leu Asp
        355                 360                 365 gaa ctg tga                                                         1113
Glu Leu
370
```

<210> SEQ ID NO 36
<211> LENGTH: 370
<212> TYPE: PRT
<213> ORGANISM: Xylella almond

<400> SEQUENCE: 36

```
Met Thr Glu Phe Ile Pro Pro Gly Ser Leu Phe His Ala Leu Ser Ser
 1               5                  10                  15

Pro Phe Ala Met Lys Arg Gly Gly Gln Leu His His Ala Arg Ile Ala
            20                  25                  30

Tyr Glu Thr Trp Gly Arg Leu Asn Ala Ser Ala Thr Asn Ala Ile Leu
        35                  40                  45

Ile Met Pro Gly Leu Ser Pro Asn Ala His Ala

```
Ser Ala Ile Glu Val Val His Ala Leu Gly Ile Lys Gln Leu Ala Ser
    130                 135                 140

Leu Ile Gly Asn Ser Met Gly Gly Met Thr Ala Leu Ala Ile Leu Leu
145                 150                 155                 160

Leu His Pro Asp Ile Ala Arg Ser His Ile Asn Ile Ser Gly Ser Ala
                165                 170                 175

Gln Ala Leu Pro Phe Ser Ile Ala Ile Arg Ser Leu Gln Arg Glu Ala
            180                 185                 190

Ile Arg Leu Asp Pro His Trp Arg Gln Gly Asp Tyr Asp Asp Thr His
        195                 200                 205

Tyr Pro Glu Ser Gly Leu Arg Ile Ala Arg Lys Leu Gly Val Ile Thr
    210                 215                 220

Tyr Arg Ser Ala Leu Glu Trp Asp Gly Arg Phe Gly Arg Val Arg Leu
225                 230                 235                 240

Asp Ser Asp Gln Thr Asn Asp Thr Pro Phe Gly Leu Glu Phe Gln Ile
                245                 250                 255

Glu Asn Tyr Leu Glu Ser His Ala His Arg Phe Val His Thr Phe Asp
            260                 265                 270

Pro Asn Cys Tyr Leu Tyr Leu Ser Arg Ser Met Asp Trp Phe Asp Val
        275                 280                 285

Ala Glu Tyr Ala Asn Gly Asp Ile Leu Ala Gly Leu Ala Arg Ile Arg
    290                 295                 300

Ile Gln Arg Ala Leu Ala Ile Gly Ser His Thr Asp Ile Leu Phe Pro
305                 310                 315                 320

Ile Gln Gln Gln Gln Ile Ala Glu Gly Leu Arg Arg Gly Gly Thr
                325                 330                 335

His Ala Thr Phe Leu Gly Leu Asp Ser Pro Gln Gly His Asp Ala Phe
            340                 345                 350

Leu Val Asp Ile Ala Arg Phe Gly Pro Pro Val Lys Glu Phe Leu Asp
        355                 360                 365

Glu Leu
    370

<210> SEQ ID NO 37
<211> LENGTH: 1113
<212> TYPE: DNA
<213> ORGANISM: Xylella oleander
<220> FEATURE:
<221> NAME/KEY: CDS
<222> LOCATION: (1)..(1110)
<223> OTHER INFORMATION: RXFY01729

<400> SEQUENCE: 37 atg acc gaa ttt atc cct ccg ggc agc cta ttc cat gcg ctc tcc tct      48
Met Thr Glu Phe Ile Pro Pro Gly Ser Leu Phe His Ala Leu Ser Ser
  1               5                  10                  15 cca ttt gcg atg aag cgt ggc gga caa ctc cac cac gcc cgc atc gct      96
Pro Phe Ala Met Lys Arg Gly Gly Gln Leu His His Ala Arg Ile Ala
             20                  25                  30 tac gaa aca tgg ggc cgc ctc aat gcc agc gcc acc aat gcc att ctg     144
Tyr Glu Thr Trp Gly Arg Leu Asn Ala Ser Ala Thr Asn Ala Ile Leu
         35                  40                  45 atc atg cct ggc tta tca ccc aat gca cat gcc gca cat gac agc         192
Ile Met Pro Gly Leu Ser Pro Asn Ala His Ala Ala His His Asp Ser
     50                  55                  60 aat gct gag cca ggc tgg tgg gag tca atg cta ggt cca ggc aaa ccc     240
Asn Ala Glu Pro Gly Trp Trp Glu Ser Met Leu Gly Pro Gly Lys Pro
```

```
                         65                  70                  75                  80
atc gac aca gac cgt tgg ttc gtg atc tgt gtc aac tca ctt ggt agc         288
Ile Asp Thr Asp Arg Trp Phe Val Ile Cys Val Asn Ser Leu Gly Ser
                    85                  90                  95 tgc aaa gga tcg act ggc cct gca tcg tac aac ccc atc acg cag gcc         336
Cys Lys Gly Ser Thr Gly Pro Ala Ser Tyr Asn Pro Ile Thr Gln Ala
                100                 105                 110 atg tat cgt ttg gac ttt cca gca ctg tca atc gaa gac ggg gcc aac         384
Met Tyr Arg Leu Asp Phe Pro Ala Leu Ser Ile Glu Asp Gly Ala Asn
            115                 120                 125 gcc gca att gaa gtg gta cat gca ctg ggc atc aag caa ctt gcc agc         432
Ala Ala Ile Glu Val Val His Ala Leu Gly Ile Lys Gln Leu Ala Ser
        130                 135                 140 ctg atc ggc aat tca atg ggg ggc atg acg aca ctg gcc atc ctg ctg         480
Leu Ile Gly Asn Ser Met Gly Gly Met Thr Thr Leu Ala Ile Leu Leu
145                 150                 155                 160 tta cat cca gat att gcc cgc agc cac atc aac atc tca ggc agc gcg         528
Leu His Pro Asp Ile Ala Arg Ser His Ile Asn Ile Ser Gly Ser Ala
                165                 170                 175 cag gca tta ccg ttt tcc atc gcc att cgc tcg cta caa cgc gag gcg         576
Gln Ala Leu Pro Phe Ser Ile Ala Ile Arg Ser Leu Gln Arg Glu Ala
                180                 185                 190 atc cgc ctg gac ccc cat tgg aag cag gga gac tac gac gac acc cac         624
Ile Arg Leu Asp Pro His Trp Lys Gln Gly Asp Tyr Asp Asp Thr His
            195                 200                 205 tac ccg gaa tcg ggg cta cgc atc gca cgc aaa ctc ggg gtg atc acc         672
Tyr Pro Glu Ser Gly Leu Arg Ile Ala Arg Lys Leu Gly Val Ile Thr
        210                 215                 220 tac cgc tcc gcg ctg gaa tgg gac ggg cgt ttt ggc cgg gta cgc ttg         720
Tyr Arg Ser Ala Leu Glu Trp Asp Gly Arg Phe Gly Arg Val Arg Leu
225                 230                 235                 240 gat tcg gac caa acc aac gac aca cca ttc gga ctg gaa ttc caa att         768
Asp Ser Asp Gln Thr Asn Asp Thr Pro Phe Gly Leu Glu Phe Gln Ile
                245                 250                 255 gaa aac tac ttg gaa agc cat gca cac cgc ttc gtg cac acc ttc gac         816
Glu Asn Tyr Leu Glu Ser His Ala His Arg Phe Val His Thr Phe Asp
                260                 265                 270 cca aac tgc tac ctg tac ctg agc cgc tcc atg gac tgg ttc gac gtg         864
Pro Asn Cys Tyr Leu Tyr Leu Ser Arg Ser Met Asp Trp Phe Asp Val
            275                 280                 285 gcc gag tac gcc aat gga gac att ctt gcc ggg ctg gcc agg atc cga         912
Ala Glu Tyr Ala Asn Gly Asp Ile Leu Ala Gly Leu Ala Arg Ile Arg
        290                 295                 300 atc caa cgc gca ctt gcc atc ggt agc cat acc gac atc ctc ttt cca         960
Ile Gln Arg Ala Leu Ala Ile Gly Ser His Thr Asp Ile Leu Phe Pro
305                 310                 315                 320 ata caa cag caa caa caa att gcc gaa ggg cta cgc cgt ggc ggt aca         1008
Ile Gln Gln Gln Gln Gln Ile Ala Glu Gly Leu Arg Arg Gly Gly Thr
                325                 330                 335 cac gcc acc ttc ctg ggc ctt gac tca ccg cag gga cat gat gcg ttc         1056
His Ala Thr Phe Leu Gly Leu Asp Ser Pro Gln Gly His Asp Ala Phe
                340                 345                 350 ctt gtg gat atc gca gga ttt ggc cct cca gtg aag gaa ttt ctg ggc         1104
Leu Val Asp Ile Ala Gly Phe Gly Pro Pro Val Lys Glu Phe Leu Gly
            355                 360                 365 gaa ctg tga                                                             1113
Glu Leu
370
```

```
<210> SEQ ID NO 38
<211> LENGTH: 370
<212> TYPE: PRT
<213> ORGANISM: Xylella oleander

<400> SEQUENCE: 38

Met Thr Glu Phe Ile Pro Pro Gly Ser Leu Phe His Ala Leu Ser Ser
  1               5                  10                  15

Pro Phe Ala Met Lys Arg Gly Gly Gln Leu His His Ala Arg Ile Ala
             20                  25                  30

Tyr Glu Thr Trp Gly Arg Leu Asn Ala Ser Ala Thr Asn Ala Ile Leu
         35                  40                  45

Ile Met Pro Gly Leu Ser Pro Asn Ala His Ala Ala His His Asp Ser
 50                  55                  60

Asn Ala Glu Pro Gly Trp Trp Glu Ser Met Leu Gly Pro Gly Lys Pro
 65                  70                  75                  80

Ile Asp Thr Asp Arg Trp Phe Val Ile Cys Val Asn Ser Leu Gly Ser
                 85                  90                  95

Cys Lys Gly Ser Thr Gly Pro Ala Ser Tyr Asn Pro Ile Thr Gln Ala
            100                 105                 110

Met Tyr Arg Leu Asp Phe Pro Ala Leu Ser Ile Glu Asp Gly Ala Asn
            115                 120                 125

Ala Ala Ile Glu Val Val His Ala Leu Gly Ile Lys Gln Leu Ala Ser
            130                 135                 140

Leu Ile Gly Asn Ser Met Gly Gly Met Thr Thr Leu Ala Ile Leu Leu
145                 150                 155                 160

Leu His Pro Asp Ile Ala Arg Ser His Ile Asn Ile Ser Gly Ser Ala
                165                 170                 175

Gln Ala Leu Pro Phe Ser Ile Ala Ile Arg Ser Leu Gln Arg Glu Ala
            180                 185                 190

Ile Arg Leu Asp Pro His Trp Lys Gln Gly Asp Tyr Asp Asp Thr His
            195                 200                 205

Tyr Pro Glu Ser Gly Leu Arg Ile Ala Arg Lys Leu Gly Val Ile Thr
210                 215                 220

Tyr Arg Ser Ala Leu Glu Trp Asp Gly Arg Phe Gly Arg Val Arg Leu
225                 230                 235                 240

Asp Ser Asp Gln Thr Asn Asp Thr Pro Phe Gly Leu Glu Phe Gln Ile
                245                 250                 255

Glu Asn Tyr Leu Glu Ser His Ala His Arg Phe Val His Thr Phe Asp
            260                 265                 270

Pro Asn Cys Tyr Leu Tyr Leu Ser Arg Ser Met Asp Trp Phe Asp Val
            275                 280                 285

Ala Glu Tyr Ala Asn Gly Asp Ile Leu Ala Gly Leu Ala Arg Ile Arg
            290                 295                 300

Ile Gln Arg Ala Leu Ala Ile Gly Ser His Thr Asp Ile Leu Phe Pro
305                 310                 315                 320

Ile Gln Gln Gln Gln Gln Ile Ala Glu Gly Leu Arg Arg Gly Gly Thr
                325                 330                 335

His Ala Thr Phe Leu Gly Leu Asp Ser Pro Gln Gly His Asp Ala Phe
            340                 345                 350

Leu Val Asp Ile Ala Gly Phe Gly Pro Pro Val Lys Glu Phe Leu Gly
            355                 360                 365

Glu Leu
    370
```

<210> SEQ ID NO 39
<211> LENGTH: 1578
<212> TYPE: DNA
<213> ORGANISM: Emericella nidulans
<220> FEATURE:
<221> NAME/KEY: CDS
<222> LOCATION: (1)..(1575)
<223> OTHER INFORMATION: REN00010

<400> SEQUENCE: 39

```
atg agt ccg ctg aac ggc gtc gct cgt tcc ttt ccg cgg ccc ttc cag      48
Met Ser Pro Leu Asn Gly Val Ala Arg Ser Phe Pro Arg Pro Phe Gln
 1               5                  10                  15 gcc gtg acc agg cgg cct ttt cga gtt gtc cag ccg gcc atc gcc tgt      96
Ala Val Thr Arg Arg Pro Phe Arg Val Val Gln Pro Ala Ile Ala Cys
             20                  25                  30 ccg tcc aac agc cgg tcg ttt aac cat tct cga tca tta cga tca acg     144
Pro Ser Asn Ser Arg Ser Phe Asn His Ser Arg Ser Leu Arg Ser Thr
         35                  40                  45 ggg tct cag tcc ccc gct cca tcc cca cgc gac tcc tcg aat ccc gcg     192
Gly Ser Gln Ser Pro Ala Pro Ser Pro Arg Asp Ser Ser Asn Pro Ala
     50                  55                  60 ctg tcc ttc cct tgc ctc gac gcc cag gag gcc aag tcc gct ctt ctt     240
Leu Ser Phe Pro Cys Leu Asp Ala Gln Glu Ala Lys Ser Ala Leu Leu
 65                  70                  75                  80 tcc gcg cga tct ctt ggt tca ggc cct gaa ccc tcc tat acc gcc ggc     288
Ser Ala Arg Ser Leu Gly Ser Gly Pro Glu Pro Ser Tyr Thr Ala Gly
                 85                  90                  95 cac cac gaa cga ttc cat tcc gac gaa ccg ctg ctc ctt gat tgg ggc     336
His His Glu Arg Phe His Ser Asp Glu Pro Leu Leu Leu Asp Trp Gly
            100                 105                 110 ggt ttg ctt cca gaa ttt gat atc gca tat gag aca tgg ggc cag ctg     384
Gly Leu Leu Pro Glu Phe Asp Ile Ala Tyr Glu Thr Trp Gly Gln Leu
        115                 120                 125 aac gag aag aag gat aat gtc att ctg ctg cat acc ggt ctg tct gca     432
Asn Glu Lys Lys Asp Asn Val Ile Leu Leu His Thr Gly Leu Ser Ala
    130                 135                 140 tct agc cat gcg cac agc acc gaa gcg aac ccg aag ccc ggc tgg tgg     480
Ser Ser His Ala His Ser Thr Glu Ala Asn Pro Lys Pro Gly Trp Trp
145                 150                 155                 160 gag aaa ttc ata ggt cct ggg aag acg cta gat acg gac aag tac ttt     528
Glu Lys Phe Ile Gly Pro Gly Lys Thr Leu Asp Thr Asp Lys Tyr Phe
                165                 170                 175 gtg atc tgc acc aat gtc ctt gga ggg tgc tac ggt agc acg ggg ccc     576
Val Ile Cys Thr Asn Val Leu Gly Gly Cys Tyr Gly Ser Thr Gly Pro
            180                 185                 190 tcg acg gtg gac ccg tcg gat ggg aag aag tat gct acg cgg ttt ccc     624
Ser Thr Val Asp Pro Ser Asp Gly Lys Lys Tyr Ala Thr Arg Phe Pro
        195                 200                 205 atc ctg aca att gaa gat atg gtg cga gcg cag ttc cgc ctt ttg gac     672
Ile Leu Thr Ile Glu Asp Met Val Arg Ala Gln Phe Arg Leu Leu Asp
    210                 215                 220 cat ctt ggg gtt cgg aaa ctc tac gcg tcc gtc ggc tcc agc atg ggt     720
His Leu Gly Val Arg Lys Leu Tyr Ala Ser Val Gly Ser Ser Met Gly
225                 230                 235                 240 ggt atg cag agt ctt gca gcc ggt gtt ctg ttc cca gag cga gtg ggc     768
Gly Met Gln Ser Leu Ala Ala Gly Val Leu Phe Pro Glu Arg Val Gly
                245                 250                 255 aag att gtg tcg att agc ggt tgt gct cga agc cat ccg tac agc att     816
Lys Ile Val Ser Ile Ser Gly Cys Ala Arg Ser His Pro Tyr Ser Ile
            260                 265                 270
```

```
gct atg cgc cat acc cag cgg cag gtg ttg atg atg gat cca aat tgg      864
Ala Met Arg His Thr Gln Arg Gln Val Leu Met Met Asp Pro Asn Trp
        275                 280                 285 gct cga ggt ttc tac tac gat tcg atc cca cct cat tca ggc atg aag      912
Ala Arg Gly Phe Tyr Tyr Asp Ser Ile Pro Pro His Ser Gly Met Lys
    290                 295                 300 ctc gct cgc gag att gcc acc gtc acg tac cgc agc gga cca gaa tgg      960
Leu Ala Arg Glu Ile Ala Thr Val Thr Tyr Arg Ser Gly Pro Glu Trp
305                 310                 315                 320 gag aaa cgc ttt ggt cgg aaa cgg gct gat ccg agc aaa cag cct gcg     1008
Glu Lys Arg Phe Gly Arg Lys Arg Ala Asp Pro Ser Lys Gln Pro Ala
            325                 330                 335 ctt tgc ccc gac ttt ctc atc gag acg tat ctc gac cac gcc ggt gaa     1056
Leu Cys Pro Asp Phe Leu Ile Glu Thr Tyr Leu Asp His Ala Gly Glu
        340                 345                 350 aaa ttc tgc ttg gaa tac gat gcc aac agc ctg ctc tac atc tcc aag     1104
Lys Phe Cys Leu Glu Tyr Asp Ala Asn Ser Leu Leu Tyr Ile Ser Lys
    355                 360                 365 gcg atg gat ctg ttt gac cta ggg ttg act cag caa ctc gcg acg aag     1152
Ala Met Asp Leu Phe Asp Leu Gly Leu Thr Gln Gln Leu Ala Thr Lys
370                 375                 380 aag cag agg gcg gag gcc cag gcg aag att agc agc gga aca aac act     1200
Lys Gln Arg Ala Glu Ala Gln Ala Lys Ile Ser Ser Gly Thr Asn Thr
385                 390                 395                 400 gtc aat gat gcg tcg tgc agc ctt aca ctt cct gaa cag cca tac cag     1248
Val Asn Asp Ala Ser Cys Ser Leu Thr Leu Pro Glu Gln Pro Tyr Gln
                405                 410                 415 gag cag cca tct gcc tcg aca tcc gcc gag cag tct gct tcc gct tca     1296
Glu Gln Pro Ser Ala Ser Thr Ser Ala Glu Gln Ser Ala Ser Ala Ser
            420                 425                 430 gag acc ggg tcg gct ccg aac gat ctt gtt gcc ggg ctt gcg ccg ctg     1344
Glu Thr Gly Ser Ala Pro Asn Asp Leu Val Ala Gly Leu Ala Pro Leu
        435                 440                 445 aaa gac cat cag gtg ctg gta atc gga gtc gca agc gac att ctc ttc     1392
Lys Asp His Gln Val Leu Val Ile Gly Val Ala Ser Asp Ile Leu Phe
    450                 455                 460 ccg gcg tgg caa cag cgc gag atc gcg gag act ctg att caa gca ggg     1440
Pro Ala Trp Gln Gln Arg Glu Ile Ala Glu Thr Leu Ile Gln Ala Gly
465                 470                 475                 480 aac aag acc gtg gag cat att gag ctg ggc aac gac gtg tct ctc ttt     1488
Asn Lys Thr Val Glu His Ile Glu Leu Gly Asn Asp Val Ser Leu Phe
                485                 490                 495 ggt cat gac aca ttc ctc ctt gat gtc aga acg tcg gag gcg cag ttc     1536
Gly His Asp Thr Phe Leu Leu Asp Val Arg Thr Ser Glu Ala Gln Phe
            500                 505                 510 gca agt tcc gta cta gtc ggc tcg cac ata att gta caa tag             1578
Ala Ser Ser Val Leu Val Gly Ser His Ile Ile Val Gln
        515                 520                 525

<210> SEQ ID NO 40
<211> LENGTH: 525
<212> TYPE: PRT
<213> ORGANISM: Emericella nidulans

<400> SEQUENCE: 40

Met Ser Pro Leu Asn Gly Val Ala Arg Ser Phe Pro Arg Pro Phe Gln
 1               5                  10                  15

Ala Val Thr Arg Arg Pro Phe Arg Val Val Gln Pro Ala Ile Ala Cys
            20                  25                  30
```

-continued

```
Pro Ser Asn Ser Arg Ser Phe Asn His Ser Arg Ser Leu Arg Ser Thr
        35                  40                  45

Gly Ser Gln Ser Pro Ala Pro Ser Pro Arg Asp Ser Ser Asn Pro Ala
    50                  55                  60

Leu Ser Phe Pro Cys Leu Asp Ala Gln Glu Ala Lys Ser Ala Leu Leu
65                  70                  75                  80

Ser Ala Arg Ser Leu Gly Ser Gly Pro Glu Pro Ser Tyr Thr Ala Gly
                85                  90                  95

His His Glu Arg Phe His Ser Asp Glu Pro Leu Leu Leu Asp Trp Gly
                100                 105                 110

Gly Leu Leu Pro Glu Phe Asp Ile Ala Tyr Glu Thr Trp Gly Gln Leu
        115                 120                 125

Asn Glu Lys Lys Asp Asn Val Ile Leu Leu His Thr Gly Leu Ser Ala
    130                 135                 140

Ser Ser His Ala His Ser Thr Glu Ala Asn Pro Lys Pro Gly Trp Trp
145                 150                 155                 160

Glu Lys Phe Ile Gly Pro Gly Lys Thr Leu Asp Thr Asp Lys Tyr Phe
                165                 170                 175

Val Ile Cys Thr Asn Val Leu Gly Gly Cys Tyr Gly Ser Thr Gly Pro
                180                 185                 190

Ser Thr Val Asp Pro Ser Asp Gly Lys Lys Tyr Ala Thr Arg Phe Pro
        195                 200                 205

Ile Leu Thr Ile Glu Asp Met Val Arg Ala Gln Phe Arg Leu Leu Asp
    210                 215                 220

His Leu Gly Val Arg Lys Leu Tyr Ala Ser Val Gly Ser Ser Met Gly
225                 230                 235                 240

Gly Met Gln Ser Leu Ala Ala Gly Val Leu Phe Pro Glu Arg Val Gly
                245                 250                 255

Lys Ile Val Ser Ile Ser Gly Cys Ala Arg Ser His Pro Tyr Ser Ile
                260                 265                 270

Ala Met Arg His Thr Gln Arg Gln Val Leu Met Met Asp Pro Asn Trp
        275                 280                 285

Ala Arg Gly Phe Tyr Tyr Asp Ser Ile Pro Pro His Ser Gly Met Lys
    290                 295                 300

Leu Ala Arg Glu Ile Ala Thr Val Thr Tyr Arg Ser Gly Pro Glu Trp
305                 310                 315                 320

Glu Lys Arg Phe Gly Arg Lys Arg Ala Asp Pro Ser Lys Gln Pro Ala
                325                 330                 335

Leu Cys Pro Asp Phe Leu Ile Glu Thr Tyr Leu Asp His Ala Gly Glu
                340                 345                 350

Lys Phe Cys Leu Glu Tyr Asp Ala Asn Ser Leu Leu Tyr Ile Ser Lys
        355                 360                 365

Ala Met Asp Leu Phe Asp Leu Gly Leu Thr Gln Gln Leu Ala Thr Lys
    370                 375                 380

Lys Gln Arg Ala Glu Ala Gln Ala Lys Ile Ser Ser Gly Thr Asn Thr
385                 390                 395                 400

Val Asn Asp Ala Ser Cys Ser Leu Thr Leu Pro Glu Gln Pro Tyr Gln
                405                 410                 415

Glu Gln Pro Ser Ala Ser Thr Ser Ala Glu Gln Ser Ala Ser Ala Ser
                420                 425                 430

Glu Thr Gly Ser Ala Pro Asn Asp Leu Val Ala Gly Leu Ala Pro Leu
        435                 440                 445

Lys Asp His Gln Val Leu Val Ile Gly Val Ala Ser Asp Ile Leu Phe
```

```
                  450             455             460
Pro Ala Trp Gln Gln Arg Glu Ile Ala Glu Thr Leu Ile Gln Ala Gly
465                 470                 475                 480

Asn Lys Thr Val Glu His Ile Glu Leu Gly Asn Asp Val Ser Leu Phe
                485                 490                 495

Gly His Asp Thr Phe Leu Leu Asp Val Arg Thr Ser Glu Ala Gln Phe
            500                 505                 510

Ala Ser Ser Val Leu Val Gly Ser His Ile Ile Val Gln
        515                 520                 525

<210> SEQ ID NO 41
<211> LENGTH: 1170
<212> TYPE: DNA
<213> ORGANISM: Mesorhizobium loti
<220> FEATURE:
<221> NAME/KEY: CDS
<222> LOCATION: (1)..(1167)
<223> OTHER INFORMATION: NP_104621

<400> SEQUENCE: 41 atg gcc gct ctg cgc gca gga aag acc aac aac gag gcc gac cag ccg      48
Met Ala Ala Leu Arg Ala Gly Lys Thr Asn Asn Glu Ala Asp Gln Pro
 1               5                  10                  15 tcg agc ccg gtg ttg cgc ttc ggg gcg gac aag ccg ctc aag ctc gac      96
Ser Ser Pro Val Leu Arg Phe Gly Ala Asp Lys Pro Leu Lys Leu Asp
                20                  25                  30 gcc ggc acg ctt ttg tcg ccg ttc cag atc gcc tat cag acc tac ggc     144
Ala Gly Thr Leu Leu Ser Pro Phe Gln Ile Ala Tyr Gln Thr Tyr Gly
            35                  40                  45 acg ctg aac gat gcc cgc tcc aat gcc atc ctc gtc tgc cat gcg ctg     192
Thr Leu Asn Asp Ala Arg Ser Asn Ala Ile Leu Val Cys His Ala Leu
        50                  55                  60 acc ggc gac cag cat gtc gcc aac acc aat ccg gtg acc ggc aag ccg     240
Thr Gly Asp Gln His Val Ala Asn Thr Asn Pro Val Thr Gly Lys Pro
 65                  70                  75                  80 gga tgg tgg gaa gtg ctg atc ggc ccc ggc agg atc atc gac acc aac     288
Gly Trp Trp Glu Val Leu Ile Gly Pro Gly Arg Ile Ile Asp Thr Asn
                 85                  90                  95 cgt ttc ttc gtc atc tgc tcc aac gtc atc ggc ggt tgt ctg ggc tcc     336
Arg Phe Phe Val Ile Cys Ser Asn Val Ile Gly Gly Cys Leu Gly Ser
                100                 105                 110 acc ggc ccg gcc tcg acc aac ccc gcc acc ggc aag ccc tac ggg ctc     384
Thr Gly Pro Ala Ser Thr Asn Pro Ala Thr Gly Lys Pro Tyr Gly Leu
            115                 120                 125 gac ctg ccg gtc atc acc atc cgc gat atg gtg cgc gcg cag cag atg     432
Asp Leu Pro Val Ile Thr Ile Arg Asp Met Val Arg Ala Gln Gln Met
        130                 135                 140 ctg atc gat cat ttc ggc atc gag aaa ctg ttc tgc gtg ctc ggc ggc     480
Leu Ile Asp His Phe Gly Ile Glu Lys Leu Phe Cys Val Leu Gly Gly
145                 150                 155                 160 tcg atg ggc gga atg cag gtg ctg gaa tgg gcg tcg agc tac ccc gag     528
Ser Met Gly Gly Met Gln Val Leu Glu Trp Ala Ser Ser Tyr Pro Glu
                165                 170                 175 cgc gtc ttt tcg gca ctg ccg atc gcc acc ggc gcg cgc cat tcc tcg     576
Arg Val Phe Ser Ala Leu Pro Ile Ala Thr Gly Ala Arg His Ser Ser
                180                 185                 190 cag aac atc gcc ttc cac gag gtc ggc cgg cag gct gtc atg gcc gat     624
Gln Asn Ile Ala Phe His Glu Val Gly Arg Gln Ala Val Met Ala Asp
            195                 200                 205 ccg gac tgg cac ggc ggc aaa tat ttc gaa aac ggc aaa cgc ccg gaa     672
```

```
                Pro Asp Trp His Gly Gly Lys Tyr Phe Glu Asn Gly Lys Arg Pro Glu
                    210                 215                 220 aag ggc ctg gcg gta gcg cgc atg gcc gcc cac ata acc tat ctg tcg          720
Lys Gly Leu Ala Val Ala Arg Met Ala Ala His Ile Thr Tyr Leu Ser
225                 230                 235                 240 gaa gcc gcc ctg cac cgg aaa ttc ggc cgc aat ctg cag gat cgc gag          768
Glu Ala Ala Leu His Arg Lys Phe Gly Arg Asn Leu Gln Asp Arg Glu
                245                 250                 255 gcg ctg acc ttc ggc ttc gac gcc gac ttc cag atc gaa agc tat ctg          816
Ala Leu Thr Phe Gly Phe Asp Ala Asp Phe Gln Ile Glu Ser Tyr Leu
            260                 265                 270 cgc cac caa ggc atg acc ttc gtc gac cgc ttc gac gcc aat tcc tat          864
Arg His Gln Gly Met Thr Phe Val Asp Arg Phe Asp Ala Asn Ser Tyr
        275                 280                 285 ctc tac atg acg cgg tcg atg gac tat ttc gac ctc gcc gcc gat cat          912
Leu Tyr Met Thr Arg Ser Met Asp Tyr Phe Asp Leu Ala Ala Asp His
    290                 295                 300 ggc ggg cgg ctg gcg gat gcc ttt gcc ggc acc aaa acc cgc ttc tgc          960
Gly Gly Arg Leu Ala Asp Ala Phe Ala Gly Thr Lys Thr Arg Phe Cys
305                 310                 315                 320 ctg gtg tcc ttc acc tcg gat tgg ttg ttt ccg acc gaa gag agc cgc         1008
Leu Val Ser Phe Thr Ser Asp Trp Leu Phe Pro Thr Glu Glu Ser Arg
                325                 330                 335 tcg atc gtg cac gcg ctc aac gcc gcc ggc gcg tcc gtg tcc ttc gtc         1056
Ser Ile Val His Ala Leu Asn Ala Ala Gly Ala Ser Val Ser Phe Val
            340                 345                 350 gaa atc gag acc gac cgc ggc cac gat gcc ttc ctg ctc gac gag ccg         1104
Glu Ile Glu Thr Asp Arg Gly His Asp Ala Phe Leu Leu Asp Glu Pro
        355                 360                 365 gaa ctg ttc gcc gcc atc aac ggc ttc atc ggc tcc gcg gcg cgg gcg         1152
Glu Leu Phe Ala Ala Ile Asn Gly Phe Ile Gly Ser Ala Ala Arg Ala
    370                 375                 380 aga ggg cta agc gca tga                                                 1170
Arg Gly Leu Ser Ala
385

<210> SEQ ID NO 42
<211> LENGTH: 389
<212> TYPE: PRT
<213> ORGANISM: Mesorhizobium loti

<400> SEQUENCE: 42

Met Ala Ala Leu Arg Ala Gly Lys Thr Asn Asn Glu Ala Asp Gln Pro
1               5                   10                  15

Ser Ser Pro Val Leu Arg Phe Gly Ala Asp Lys Pro Leu Lys Leu Asp
                20                  25                  30

Ala Gly Thr Leu Leu Ser Pro Phe Gln Ile Ala Tyr Gln Thr Tyr Gly
            35                  40                  45

Thr Leu Asn Asp Ala Arg Ser Asn Ala Ile Leu Val Cys His Ala Leu
        50                  55                  60

Thr Gly Asp Gln His Val Ala Asn Thr Asn Pro Val Thr Gly Lys Pro
65                  70                  75                  80

Gly Trp Trp Glu Val Leu Ile Gly Pro Gly Arg Ile Ile Asp Thr Asn
                85                  90                  95

Arg Phe Phe Val Ile Cys Ser Asn Val Ile Gly Gly Cys Leu Gly Ser
                100                 105                 110

Thr Gly Pro Ala Ser Thr Asn Pro Ala Thr Gly Lys Pro Tyr Gly Leu
            115                 120                 125
```

-continued

```
Asp Leu Pro Val Ile Thr Ile Arg Asp Met Val Arg Ala Gln Gln Met
    130                 135                 140

Leu Ile Asp His Phe Gly Ile Glu Lys Leu Phe Cys Val Leu Gly Gly
145                 150                 155                 160

Ser Met Gly Gly Met Gln Val Leu Glu Trp Ala Ser Ser Tyr Pro Glu
                165                 170                 175

Arg Val Phe Ser Ala Leu Pro Ile Ala Thr Gly Ala Arg His Ser Ser
            180                 185                 190

Gln Asn Ile Ala Phe His Glu Val Gly Arg Gln Ala Val Met Ala Asp
        195                 200                 205

Pro Asp Trp His Gly Gly Lys Tyr Phe Glu Asn Gly Lys Arg Pro Glu
210                 215                 220

Lys Gly Leu Ala Val Ala Arg Met Ala Ala His Ile Thr Tyr Leu Ser
225                 230                 235                 240

Glu Ala Ala Leu His Arg Lys Phe Gly Arg Asn Leu Gln Asp Arg Glu
                245                 250                 255

Ala Leu Thr Phe Gly Phe Asp Ala Asp Phe Gln Ile Glu Ser Tyr Leu
            260                 265                 270

Arg His Gln Gly Met Thr Phe Val Asp Arg Phe Asp Ala Asn Ser Tyr
        275                 280                 285

Leu Tyr Met Thr Arg Ser Met Asp Tyr Phe Asp Leu Ala Ala Asp His
    290                 295                 300

Gly Gly Arg Leu Ala Asp Ala Phe Ala Gly Thr Lys Thr Arg Phe Cys
305                 310                 315                 320

Leu Val Ser Phe Thr Ser Asp Trp Leu Phe Pro Thr Glu Glu Ser Arg
                325                 330                 335

Ser Ile Val His Ala Leu Asn Ala Ala Gly Ala Ser Val Ser Phe Val
            340                 345                 350

Glu Ile Glu Thr Asp Arg Gly His Asp Ala Phe Leu Leu Asp Glu Pro
        355                 360                 365

Glu Leu Phe Ala Ala Ile Asn Gly Phe Ile Gly Ser Ala Ala Arg Ala
    370                 375                 380

Arg Gly Leu Ser Ala
385
```

<210> SEQ ID NO 43
<211> LENGTH: 1155
<212> TYPE: DNA
<213> ORGANISM: acremonium crysogenum
<220> FEATURE:
<221> NAME/KEY: CDS
<222> LOCATION: (1)..(1152)
<223> OTHER INFORMATION: P39058

<400> SEQUENCE: 43

```
tgt cgc ctc aga tcg cca atc gct tcg agg ctt cgc tag atg ccc aag      48
Cys Arg Leu Arg Ser Pro Ile Ala Ser Arg Leu Arg Xaa Met Pro Lys
  1               5                  10                  15 aca tag cca gaa tat cgc tct tca cac tgg aat ctg gcg tca tcc ttc      96
Thr Xaa Pro Glu Tyr Arg Ser Ser His Trp Asn Leu Ala Ser Ser Phe
             20                  25                  30 gcg atg tac ccg tgg cat aca aat cgt ggg gtc gca tga atg tct caa     144
Ala Met Tyr Pro Trp His Thr Asn Arg Gly Val Ala Xaa Met Ser Gln
         35                  40                  45 ggg ata act gcg tca tcg tct gcc aca cct tga cga gca gcg ccc atg     192
Gly Ile Thr Ala Ser Ser Ser Ala Thr Pro Xaa Arg Ala Ala Pro Met
     50                  55                  60
```

-continued

| | |
|---|---|
| tca cct cgt ggt ggc cca cac tgt ttg gcc aag gca ggg ctt tcg ata<br>Ser Pro Arg Gly Gly Pro His Cys Leu Ala Lys Ala Gly Leu Ser Ile<br>65                      70                      75                      80 | 240 |
| cct ctc gct act tca tca tct gcc taa att atc tcg gga gcc cct ttg<br>Pro Leu Ala Thr Ser Ser Ser Ala Xaa Ile Ile Ser Gly Ala Pro Leu<br>                      85                      90                      95 | 288 |
| gga gtg ctg gac cat gtt cac cgg acc ccg atg cag aag gcc agc gcc<br>Gly Val Leu Asp His Val His Arg Thr Pro Met Gln Lys Ala Ser Ala<br>                100                    105                    110 | 336 |
| cgt acg ggg cca agt ttc ctc gca cga cga ttc gag atg atg ttc gta<br>Arg Thr Gly Pro Ser Phe Leu Ala Arg Arg Phe Glu Met Met Phe Val<br>        115                    120                    125 | 384 |
| ttc atc gcc agg tgc tcg aca ggt tag gcg tca ggc aaa ttg ctg ccg<br>Phe Ile Ala Arg Cys Ser Thr Gly Xaa Ala Ser Gly Lys Leu Leu Pro<br>130                      135                    140 | 432 |
| tag tcg gcg cat cca tgg gtg gaa tgc aca ctc tgg aat ggg cct tct<br>Xaa Ser Ala His Pro Trp Val Glu Cys Thr Leu Trp Asn Gly Pro Ser<br>145                      150                    155                    160 | 480 |
| ttg gtc ccg agt acg tgc gaa aga ttg tgc cca tcg cga cat cat gcc<br>Leu Val Pro Ser Thr Cys Glu Arg Leu Cys Pro Ser Arg His His Ala<br>                165                    170                    175 | 528 |
| gtc aga gcg gct ggt gcg cag ctt ggt tcg aga cac aga ggc agt gca<br>Val Arg Ala Ala Gly Ala Gln Leu Gly Ser Arg His Arg Gly Ser Ala<br>                180                    185                    190 | 576 |
| tct atg atg acc cca agt acc tgg acg ggg agt acg acg tag acg acc<br>Ser Met Met Thr Pro Ser Thr Trp Thr Gly Ser Thr Thr Xaa Thr Thr<br>        195                    200                    205 | 624 |
| agc ctg tcc ggg ggc tcg aaa cag cgc gca aga ttg cga atc tca cgt<br>Ser Leu Ser Gly Gly Ser Lys Gln Arg Ala Arg Leu Arg Ile Ser Arg<br>210                      215                    220 | 672 |
| aca aga gca aac ctg cga tgg acg agc gct tcc ata tgg ctc cag gag<br>Thr Arg Ala Asn Leu Arg Trp Thr Ser Ala Ser Ile Trp Leu Gln Glu<br>225                      230                    235                    240 | 720 |
| tcc aag ccg gcc gga ata tca gca gcc agg atg cga aga agg aaa tca<br>Ser Lys Pro Ala Gly Ile Ser Ala Ala Arg Met Arg Arg Arg Lys Ser<br>                      245                    250                    255 | 768 |
| acg gca cag aca gcg gca aca gcc acc gtg ctg gcc agc cca ttg aag<br>Thr Ala Gln Thr Ala Ala Thr Ala Thr Val Leu Ala Ser Pro Leu Lys<br>                260                    265                    270 | 816 |
| ccg tat ctt cct atc tcc ggt acc agg ccc aga agt ttg ccg cga gct<br>Pro Tyr Leu Pro Ile Ser Gly Thr Arg Pro Arg Ser Leu Pro Arg Ala<br>        275                    280                    285 | 864 |
| tcg acg cca act gct aca tcg cca tga cac tca agt tcg aca ccc acg<br>Ser Thr Pro Thr Ala Thr Ser Pro Xaa His Ser Ser Thr Pro Thr<br>290                      295                    300 | 912 |
| aca tca gca gag gcc ggg cag gat caa tcc cgg agg ctc tgg caa tga<br>Thr Ser Ala Glu Ala Gly Gln Asp Gln Ser Arg Arg Leu Trp Gln Xaa<br>305                      310                    315                    320 | 960 |
| tta cac aac cag cgt tga tca ttt gcg cca ggt cag acg tcg tgt act<br>Leu His Asn Gln Arg Xaa Ser Phe Ala Pro Gly Gln Thr Val Cys Thr<br>                      325                    330                    335 | 1008 |
| cgt ttg acg agc acg ttg aga tgg ggc gca gta tcc caa aca gtc gtc<br>Arg Leu Thr Ser Thr Leu Arg Trp Gly Ala Val Ser Gln Thr Val Val<br>                340                    345                    350 | 1056 |
| ttt gcg tgg tgg aca cga atg agg gtc atg act tct ttg taa tgg aag<br>Phe Ala Trp Trp Thr Arg Met Arg Val Met Thr Ser Leu Xaa Trp Lys<br>                355                    360                    365 | 1104 |
| cgg aca agg tta atg atg ccg tca gag gat tcc tcg atc agt cat taa<br>Arg Thr Arg Leu Met Met Pro Ser Glu Asp Ser Ser Ile Ser His Xaa<br>370                      375                    380 | 1152 |

```
tgt                                                          1155
```

<210> SEQ ID NO 44
<211> LENGTH: 384
<212> TYPE: PRT
<213> ORGANISM: acremonium crysogenum
<220> FEATURE:
<221> NAME/KEY: unsure
<222> LOCATION: 13 .. 13
<223> OTHER INFORMATION: All occurrences of Xaa indicate any amino acid
<220> FEATURE:
<221> NAME/KEY: unsure
<222> LOCATION: 18 .. 18
<223> OTHER INFORMATION: All occurrences of Xaa indicate any amino acid
<220> FEATURE:
<221> NAME/KEY: unsure
<222> LOCATION: 45 .. 45
<223> OTHER INFORMATION: All occurrences of Xaa indicate any amino acid
<220> FEATURE:
<221> NAME/KEY: unsure
<222> LOCATION: 59 .. 59
<223> OTHER INFORMATION: All occurrences of Xaa indicate any amino acid
<220> FEATURE:
<221> NAME/KEY: unsure
<222> LOCATION: 89 .. 89
<223> OTHER INFORMATION: All occurrences of Xaa indicate any amino acid
<220> FEATURE:
<221> NAME/KEY: unsure
<222> LOCATION: 137 .. 137
<223> OTHER INFORMATION: All occurrences of Xaa indicate any amino acid
<220> FEATURE:
<221> NAME/KEY: unsure
<222> LOCATION: 145 .. 145
<223> OTHER INFORMATION: All occurrences of Xaa indicate any amino acid
<220> FEATURE:
<221> NAME/KEY: unsure
<222> LOCATION: 206 .. 206
<223> OTHER INFORMATION: All occurrences of Xaa indicate any amino acid
<220> FEATURE:
<221> NAME/KEY: unsure
<222> LOCATION: 297 .. 297
<223> OTHER INFORMATION: All occurrences of Xaa indicate any amino acid
<220> FEATURE:
<221> NAME/KEY: unsure
<222> LOCATION: 320 .. 320
<223> OTHER INFORMATION: All occurrences of Xaa indicate any amino acid
<220> FEATURE:
<221> NAME/KEY: unsure
<222> LOCATION: 326 .. 326
<223> OTHER INFORMATION: All occurrences of Xaa indicate any amino acid
<220> FEATURE:
<221> NAME/KEY: unsure
<222> LOCATION: 366 .. 366
<223> OTHER INFORMATION: All occurrences of Xaa indicate any amino acid
<220> FEATURE:
<221> NAME/KEY: unsure
<222> LOCATION: 384 .. 384
<223> OTHER INFORMATION: All occurrences of Xaa indicate any amino acid

<400> SEQUENCE: 44

```
Cys Arg Leu Arg Ser Pro Ile Ala Ser Arg Leu Arg Xaa Met Pro Lys
  1               5                  10                  15

Thr Xaa Pro Glu Tyr Arg Ser Ser His Trp Asn Leu Ala Ser Ser Phe
             20                  25                  30

Ala Met Tyr Pro Trp His Thr Asn Arg Gly Val Ala Xaa Met Ser Gln
         35                  40                  45

Gly Ile Thr Ala Ser Ser Ser Ala Thr Pro Xaa Arg Ala Ala Pro Met
     50                  55                  60

Ser Pro Arg Gly Gly Pro His Cys Leu Ala Lys Ala Gly Leu Ser Ile
 65                  70                  75                  80

Pro Leu Ala Thr Ser Ser Ser Ala Xaa Ile Ile Ser Gly Ala Pro Leu
```

-continued

```
                    85                  90                  95
Gly Val Leu Asp His Val His Arg Thr Pro Met Gln Lys Ala Ser Ala
                100                 105                 110
Arg Thr Gly Pro Ser Phe Leu Ala Arg Arg Phe Glu Met Met Phe Val
            115                 120                 125
Phe Ile Ala Arg Cys Ser Thr Gly Xaa Ala Ser Gly Lys Leu Leu Pro
        130                 135                 140
Xaa Ser Ala His Pro Trp Val Glu Cys Thr Leu Trp Asn Gly Pro Ser
145                 150                 155                 160
Leu Val Pro Ser Thr Cys Glu Arg Leu Cys Pro Ser Arg His His Ala
                165                 170                 175
Val Arg Ala Ala Gly Ala Gln Leu Gly Ser Arg His Arg Gly Ser Ala
                180                 185                 190
Ser Met Met Thr Pro Ser Thr Trp Thr Gly Ser Thr Thr Xaa Thr Thr
            195                 200                 205
Ser Leu Ser Gly Gly Ser Lys Gln Arg Ala Arg Leu Arg Ile Ser Arg
    210                 215                 220
Thr Arg Ala Asn Leu Arg Trp Thr Ser Ala Ser Ile Trp Leu Gln Glu
225                 230                 235                 240
Ser Lys Pro Ala Gly Ile Ser Ala Ala Arg Met Arg Arg Arg Lys Ser
                245                 250                 255
Thr Ala Gln Thr Ala Ala Thr Ala Thr Val Leu Ala Ser Pro Leu Lys
            260                 265                 270
Pro Tyr Leu Pro Ile Ser Gly Thr Arg Pro Arg Ser Leu Pro Arg Ala
        275                 280                 285
Ser Thr Pro Thr Ala Thr Ser Pro Xaa His Ser Ser Thr Pro Thr
    290                 295                 300
Thr Ser Ala Glu Ala Gly Gln Asp Gln Ser Arg Arg Leu Trp Gln Xaa
305                 310                 315                 320
Leu His Asn Gln Arg Xaa Ser Phe Ala Pro Gly Gln Thr Val Cys Thr
                325                 330                 335
Arg Leu Thr Ser Thr Leu Arg Trp Gly Ala Val Ser Gln Thr Val Val
            340                 345                 350
Phe Ala Trp Trp Thr Arg Met Arg Val Met Thr Ser Leu Xaa Trp Lys
        355                 360                 365
Arg Thr Arg Leu Met Met Pro Ser Glu Asp Ser Ser Ile Ser His Xaa
    370                 375                 380
```

<210> SEQ ID NO 45
<211> LENGTH: 1077
<212> TYPE: DNA
<213> ORGANISM: Pseudomonas putida
<220> FEATURE:
<221> NAME/KEY: CDS
<222> LOCATION: (1)..(1074)
<223> OTHER INFORMATION: AAK49778

<400> SEQUENCE: 45

```
atg tca act gtc ttt ccc gaa gat tcc gtc ggt ctg gta gta cgg caa      48
Met Ser Thr Val Phe Pro Glu Asp Ser Val Gly Leu Val Val Arg Gln
  1               5                  10                  15 acc tcc cgg ttc gat gaa ccg ctg gca ctg gcc tgt ggc cgt tca ctg      96
Thr Ser Arg Phe Asp Glu Pro Leu Ala Leu Ala Cys Gly Arg Ser Leu
             20                  25                  30 gcc agt tac gaa ctg gtc tac gag acc tat ggc acc ctg aac gcc agc     144
Ala Ser Tyr Glu Leu Val Tyr Glu Thr Tyr Gly Thr Leu Asn Ala Ser
         35                  40                  45
```

```
gcg agc aac gcc gtg ctg atc tgc cat gcc ctg tcc ggc cac cac cat      192
Ala Ser Asn Ala Val Leu Ile Cys His Ala Leu Ser Gly His His His
 50                  55                  60 gcc gct ggc tac cat gcc gcc acc gac cgc aag ccg ggc tgg tgg gac      240
Ala Ala Gly Tyr His Ala Ala Thr Asp Arg Lys Pro Gly Trp Trp Asp
 65                  70                  75                  80 agc tgc atc ggc ccc gga aaa ccg atc gat acc aac cgc ttc ttc gtg      288
Ser Cys Ile Gly Pro Gly Lys Pro Ile Asp Thr Asn Arg Phe Phe Val
                 85                  90                  95 gtc agc ctg aac aac ctc ggc ggc tgc aac ggc agc acc ggc ccc agc      336
Val Ser Leu Asn Asn Leu Gly Gly Cys Asn Gly Ser Thr Gly Pro Ser
            100                 105                 110 agt gtc aac cca gcc acc ggt aaa ccc tat ggc gcc gag ttc ccg gta      384
Ser Val Asn Pro Ala Thr Gly Lys Pro Tyr Gly Ala Glu Phe Pro Val
            115                 120                 125 ttg acc gtg gaa gac tgg gtg cac agc cag gca cgg ctg gcc gac cgc      432
Leu Thr Val Glu Asp Trp Val His Ser Gln Ala Arg Leu Ala Asp Arg
        130                 135                 140 ctg ggc atc cag cag tgg gca gct atc gtc ggc ggt agc ctg ggt ggc      480
Leu Gly Ile Gln Gln Trp Ala Ala Ile Val Gly Gly Ser Leu Gly Gly
145                 150                 155                 160 atg cag gcg ctg caa tgg acg atg acc tac ccc gag cgc gta cgc cac      528
Met Gln Ala Leu Gln Trp Thr Met Thr Tyr Pro Glu Arg Val Arg His
                165                 170                 175 tgc gtc gac att gcc tcg gcc ccc aag ctg tcg gcg cag aac atc gcc      576
Cys Val Asp Ile Ala Ser Ala Pro Lys Leu Ser Ala Gln Asn Ile Ala
                180                 185                 190 ttc aac gag gtg gcg cgt cag gcc att ctt acc gac cct gag tac cgc      624
Phe Asn Glu Val Ala Arg Gln Ala Ile Leu Thr Asp Pro Glu Tyr Arg
            195                 200                 205 aga ggc tcg ttt cca gga cca ggt gtg atc ccc aag cgc ggc ctg atg      672
Arg Gly Ser Phe Pro Gly Pro Gly Val Ile Pro Lys Arg Gly Leu Met
        210                 215                 220 ctg gca cgg atg gtc ggc cac att acc tat ctg tcc gat gat tcg atg      720
Leu Ala Arg Met Val Gly His Ile Thr Tyr Leu Ser Asp Asp Ser Met
225                 230                 235                 240 ggt gaa aaa ttc ggc cga gag ctg aaa gcg aca agc tca act acg act      768
Gly Glu Lys Phe Gly Arg Glu Leu Lys Ala Thr Ser Ser Thr Thr Thr
                245                 250                 255 tcc aca gcg tcg agt tcc agg tcg aaa gct acc tgc gct atc agg gcg      816
Ser Thr Ala Ser Ser Ser Arg Ser Lys Ala Thr Cys Ala Ile Arg Ala
                260                 265                 270 agg agt ttt ccg gcc gtt tcg acg cca aca cct acc ttg atg acc aag      864
Arg Ser Phe Pro Ala Val Ser Thr Pro Thr Pro Thr Leu Met Thr Lys
            275                 280                 285 gca ctg gac tat ttc gac ccg gcc gcc acg cac ggt ggt gat ctg gcc      912
Ala Leu Asp Tyr Phe Asp Pro Ala Ala Thr His Gly Gly Asp Leu Ala
        290                 295                 300 gcc acc ctg gcc cac gtc acg gcg gac tac tgc atc tgt cgt tca cca      960
Ala Thr Leu Ala His Val Thr Ala Asp Tyr Cys Ile Cys Arg Ser Pro
305                 310                 315                 320 ccg act gcg ctt ctc tcc ggc ccg ttc gcg cga gat cgt cga cgc gct     1008
Pro Thr Ala Leu Leu Ser Gly Pro Phe Ala Arg Asp Arg Arg Arg Ala
                325                 330                 335 gat ggc cgc gcg caa gaa cgt ctg cta cct gga gat cga ttc gcc cta     1056
Asp Gly Arg Ala Gln Glu Arg Leu Leu Pro Gly Asp Arg Phe Ala Leu
            340                 345                 350 cgg gca cga tgc att tcc tga                                         1077
Arg Ala Arg Cys Ile Ser
```

```
<210> SEQ ID NO 46
<211> LENGTH: 358
<212> TYPE: PRT
<213> ORGANISM: Pseudomonas putida

<400> SEQUENCE: 46

Met Ser Thr Val Phe Pro Glu Asp Ser Val Gly Leu Val Val Arg Gln
  1               5                  10                  15

Thr Ser Arg Phe Asp Glu Pro Leu Ala Leu Ala Cys Gly Arg Ser Leu
             20                  25                  30

Ala Ser Tyr Glu Leu Val Tyr Glu Thr Tyr Gly Thr Leu Asn Ala Ser
         35                  40                  45

Ala Ser Asn Ala Val Leu Ile Cys His Ala Leu Ser Gly His His His
     50                  55                  60

Ala Ala Gly Tyr His Ala Ala Thr Asp Arg Lys Pro Gly Trp Trp Asp
 65                  70                  75                  80

Ser Cys Ile Gly Pro Gly Lys Pro Ile Asp Thr Asn Arg Phe Phe Val
                 85                  90                  95

Val Ser Leu Asn Asn Leu Gly Gly Cys Asn Gly Ser Thr Gly Pro Ser
            100                 105                 110

Ser Val Asn Pro Ala Thr Gly Lys Pro Tyr Gly Ala Glu Phe Pro Val
        115                 120                 125

Leu Thr Val Glu Asp Trp Val His Ser Gln Ala Arg Leu Ala Asp Arg
    130                 135                 140

Leu Gly Ile Gln Gln Trp Ala Ala Ile Val Gly Gly Ser Leu Gly Gly
145                 150                 155                 160

Met Gln Ala Leu Gln Trp Thr Met Thr Tyr Pro Glu Arg Val Arg His
                165                 170                 175

Cys Val Asp Ile Ala Ser Ala Pro Lys Leu Ser Ala Gln Asn Ile Ala
            180                 185                 190

Phe Asn Glu Val Ala Arg Gln Ala Ile Leu Thr Asp Pro Glu Tyr Arg
        195                 200                 205

Arg Gly Ser Phe Pro Gly Pro Gly Val Ile Pro Lys Arg Gly Leu Met
    210                 215                 220

Leu Ala Arg Met Val Gly His Ile Thr Tyr Leu Ser Asp Asp Ser Met
225                 230                 235                 240

Gly Glu Lys Phe Gly Arg Glu Leu Lys Ala Thr Ser Ser Thr Thr Thr
                245                 250                 255

Ser Thr Ala Ser Ser Ser Arg Ser Lys Ala Thr Cys Ala Ile Arg Ala
            260                 265                 270

Arg Ser Phe Pro Ala Val Ser Thr Pro Thr Pro Thr Leu Met Thr Lys
        275                 280                 285

Ala Leu Asp Tyr Phe Asp Pro Ala Ala Thr His Gly Gly Asp Leu Ala
    290                 295                 300

Ala Thr Leu Ala His Val Thr Ala Asp Tyr Cys Ile Cys Arg Ser Pro
305                 310                 315                 320

Pro Thr Ala Leu Leu Ser Gly Pro Phe Ala Arg Asp Arg Arg Arg Ala
                325                 330                 335

Asp Gly Arg Ala Gln Glu Arg Leu Leu Pro Gly Asp Arg Phe Ala Leu
            340                 345                 350

Arg Ala Arg Cys Ile Ser
        355
```

<210> SEQ ID NO 47
<211> LENGTH: 52
<212> TYPE: DNA
<213> ORGANISM: Artificial sequence
<220> FEATURE:
<223> OTHER INFORMATION: Description of the artificial sequence:PCR
      primer

<400> SEQUENCE: 47
cccgggatcc gctagcggcg cgccggccgg cccggtgtga aataccgcac ag         52

<210> SEQ ID NO 48
<211> LENGTH: 53
<212> TYPE: DNA
<213> ORGANISM: Artificial sequence
<220> FEATURE:
<223> OTHER INFORMATION: Description of the artificial sequence:PCR
      primer
<400> SEQUENCE: 48
tctagactcg agcggccgcg gccggccttt aaattgaaga cgaaagggcc tcg         53

<210> SEQ ID NO 49
<211> LENGTH: 47
<212> TYPE: DNA
<213> ORGANISM: Artificial sequence
<220> FEATURE:
<223> OTHER INFORMATION: Description of the artificial sequence:PCR
      primer
<400> SEQUENCE: 49
gagatctaga cccggggatc cgctagcggg ctgctaaagg aagcgga              47

<210> SEQ ID NO 50
<211> LENGTH: 38
<212> TYPE: DNA
<213> ORGANISM: Artificial sequence
<220> FEATURE:
<223> OTHER INFORMATION: Description of the artificial sequence:PCR
      primer
<400> SEQUENCE: 50
gagaggcgcg ccgctagcgt gggcgaagaa ctccagca                        38

<210> SEQ ID NO 51
<211> LENGTH: 34
<212> TYPE: DNA
<213> ORGANISM: Artificial sequence
<220> FEATURE:
<223> OTHER INFORMATION: Description of the artificial sequence:PCR
      primer
<400> SEQUENCE: 51
gagagggcgg ccgcgcaaag tcccgcttcg tgaa                            34

<210> SEQ ID NO 52
<211> LENGTH: 34
<212> TYPE: DNA
<213> ORGANISM: Artificial sequence
<220> FEATURE:
<223> OTHER INFORMATION: Description of the artificial sequence:PCR
      primer
<400> SEQUENCE: 52
gagagggcgg ccgctcaagt cggtcaagcc acgc                            34

<210> SEQ ID NO 53
<211> LENGTH: 140
<212> TYPE: DNA

```
<213> ORGANISM: Artificial sequence
<220> FEATURE:
<223> OTHER INFORMATION: Description of the artificial sequence:PCR
      primer
<400> SEQUENCE: 53
tcgaatttaa atctcgagag gcctgacgtc gggcccggta ccacgcgtca tatgactagt    60
tcggacctag ggatatcgtc gacatcgatg ctcttctgcg ttaattaaca attgggatcc   120
tctagacccg ggatttaaat                                                140

<210> SEQ ID NO 54
<211> LENGTH: 140
<212> TYPE: DNA
<213> ORGANISM: Artificial sequence
<220> FEATURE:
<223> OTHER INFORMATION: Description of the artificial sequence:PCR
      primer
<400> SEQUENCE: 54
gatcatttaa atcccgggtc tagaggatcc caattgttaa ttaacgcaga agagcatcga    60
tgtcgacgat atccctaggt ccgaactagt catatgacgc gtggtaccgg gcccgacgtc   120
aggcctctcg agatttaaat                                                140

<210> SEQ ID NO 55
<211> LENGTH: 33
<212> TYPE: DNA
<213> ORGANISM: Artificial sequence
<220> FEATURE:
<223> OTHER INFORMATION: Description of the artificial sequence:PCR
      primer
<400> SEQUENCE: 55
gagagcggcc gccgatcctt tttaacccat cac                                  33

<210> SEQ ID NO 56
<211> LENGTH: 32
<212> TYPE: DNA
<213> ORGANISM: Artificial sequence
<220> FEATURE:
<223> OTHER INFORMATION: Description of the artificial sequence:PCR
      primer
<400> SEQUENCE: 56
aggagcggcc gccatcggca ttttcttttg cg                                   32

<210> SEQ ID NO 57
<211> LENGTH: 5091
<212> TYPE: DNA
<213> ORGANISM: Artificial sequence
<220> FEATURE:
<223> OTHER INFORMATION: Description of the artificial sequence:plasmid

<400> SEQUENCE: 57
gccgcgactg ccttcgcgaa gccttgcccc gcggaaattt cctccaccga gttcgtgcac    60 accctatgc caagcttctt tcaccctaaa ttcgagagat tggattctta ccgtggaaat   120
tcttcgcaaa aatcgtcccc tgatcgccct tgcgacgttg gcgtcggtgc cgctggttgc   180
gcttggcttg accgacttga tcagcggccg ctcgatttaa atctcgagag gcctgacgtc   240
gggcccggta ccacgcgtca tatgactagt tcggacctag ggatatcgtc gacatcgatg   300
ctcttctgcg ttaattaaca attgggatcc tctagacccg ggatttaaat cgctagcggg   360
ctgctaaagg aagcggaaca cgtagaaagc cagtccgcag aaacggtgct gaccccggat   420
gaatgtcagc tactgggcta tctggacaag ggaaaacgca agcgcaaaga gaaagcaggt   480
agcttgcagt gggcttacat ggcgatagct agactgggcg gttttatgga cagcaagcga   540
```

-continued

```
accggaattg ccagctgggg cgccctctgg taaggttggg aagccctgca aagtaaactg      600
gatggctttc ttgccgccaa ggatctgatg gcgcagggga tcaagatctg atcaagagac      660
aggatgagga tcgtttcgca tgattgaaca agatggattg cacgcaggtt ctccggccgc      720
ttgggtggag aggctattcg gctatgactg gcacaacag  acaatcggct gctctgatgc      780
cgccgtgttc cggctgtcag cgcaggggcg cccggttctt tttgtcaaga ccgacctgtc      840
cggtgccctg aatgaactgc aggacgaggc agcgcggcta tcgtggctgg ccacgacggg      900
cgttccttgc gcagctgtgc tcgacgttgt cactgaagcg ggaagggact ggctgctatt      960
gggcgaagtg ccgggcagg  atctcctgtc atctcacctt gctcctgccg agaaagtatc     1020
catcatggct gatgcaatgc ggcggctgca tacgcttgat ccggctacct gcccattcga     1080
ccaccaagcg aaacatcgca tcgagcgagc acgtactcgg atggaagccg gtcttgtcga     1140
tcaggatgat ctggacgaag agcatcaggg gctcgcgcca gccgaactgt tcgccaggct     1200
caaggcgcgc atgcccgacg gcgaggatct cgtcgtgacc catggcgatg cctgcttgcc     1260
gaatatcatg gtggaaaatg gccgcttttc tggattcatc gactgtggcc ggctgggtgt     1320
ggcggaccgc tatcaggaca tagcgttggc tacccgtgat attgctgaag agcttggcgg     1380
cgaatgggct gaccgcttcc tcgtgcttta cggtatcgcc gctcccgatt cgcagcgcat     1440
cgccttctat cgccttcttg acgagttctt ctgagcggga ctctgggggtt cgaaatgacc     1500 gaccaagcga cgcccaacct gccatcacga gatttcgatt ccaccgccgc cttctatgaa     1560
aggttgggct tcggaatcgt tttccgggac gccggctgga tgatcctcca gcgcgggat      1620 ctcatgctgg agttcttcgc ccacgctagc ggcgcgccgg ccggcccggt gtgaaatacc     1680
gcacagatgc gtaaggagaa ataccgcat  caggcgctct ccgcttcct  cgctcactga     1740 ctcgctgcgc tcggtcgttc ggctgcggcg agcggtatca gctcactcaa aggcggtaat     1800
acggttatcc acagaatcag gggataacgc aggaaagaac atgtgagcaa aaggccagca     1860
aaaggccagg aaccgtaaaa aggccgcgtt gctggcgttt ttccataggc tccgcccccc     1920
tgacgagcat cacaaaaatc gacgctcaag tcagaggtgg cgaaacccga caggactata     1980
aagataccag gcgtttcccc ctggaagctc cctcgtgcgc tctcctgttc cgaccctgcc     2040
gcttaccgga tacctgtccg cctttctccc ttcgggaagc gtggcgcttt ctcatagctc     2100
acgctgtagg tatctcagtt cggtgtaggt cgttcgctcc aagctgggct gtgtgcacga     2160
accccccgtt cagcccgacc gctgcgcctt atccggtaac tatcgtcttg agtccaaccc     2220
ggtaagacac gacttatcgc cactggcagc agccactggt aacaggatta gcagagcgag     2280
gtatgtaggc ggtgctacag agttcttgaa gtggtggcct aactacggct acactagaag     2340
gacagtattt ggtatctgcg ctctgctgaa gccagttacc ttcggaaaaa gagttggtag     2400
ctcttgatcc ggcaaacaaa ccaccgctgg tagcggtggt ttttttgttt gcaagcagca     2460
gattacgcgc agaaaaaaag gatctcaaga agatcctttg atcttttcta cggggtctga     2520
cgctcagtgg aacgaaaact cacgttaagg gattttggtc atgagattat caaaaaggat     2580
cttcacctag atccttttaa aggccggccg cggccgcgca aagtcccgct tcgtgaaaat     2640
tttcgtgccg cgtgattttc cgccaaaaac tttaacgaac gttcgttata atggtgtcat     2700
gaccttcacg acgaagtact aaaattggcc cgaatcatca gctatggatc tctctgatgt     2760
cgcgctggag tccgacgcgc tcgatgctgc cgtcgattta aaaacggtga tcggattttt     2820
ccgagctctc gatacgacgg acgcgccagc atcacgagac tgggccagtg ccgcgagcga     2880
```

```
cctagaaact ctcgtggcgg atcttgagga gctggctgac gagctgcgtg ctcggccagc    2940
gccaggagga cgcacagtag tggaggatgc aatcagttgc gcctactgcg gtggcctgat    3000
tcctccccgg cctgacccgc gaggacggcg cgcaaaatat tgctcagatg cgtgtcgtgc    3060
cgcagccagc cgcgagcgcg ccaacaaacg ccacgccgag gagctggagg cggctaggtc    3120
gcaaatggcg ctggaagtgc gtcccccgag cgaaattttg gccatggtcg tcacagagct    3180
ggaagcggca gcgagaatta tcgcgatcgt ggcggtgccc gcaggcatga caaacatcgt    3240
aaatgccgcg tttcgtgtgc cgtggccgcc caggacgtgt cagcgccgcc accacctgca    3300
ccgaatcggc agcagcgtcg cgcgtcgaaa agcgcacag gcggcaagaa gcgataagct     3360
gcacgaatac ctgaaaaatg ttgaacgccc cgtgagcggt aactcacagg gcgtcggcta    3420
acccccagtc caaacctggg agaaagcgct caaaaatgac tctagcggat tcacgagaca    3480
ttgacacacc ggcctggaaa ttttccgctg atctgttcga cacccatccc gagctcgcgc    3540
tgcgatcacg tggctggacg agcgaagacc gccgcgaatt cctcgctcac ctgggcagag    3600
aaaatttcca gggcagcaag acccgcgact cgccagcgc ttggatcaaa gacccggaca     3660
cggagaaaca cagccgaagt tataccgagt tggttcaaaa tcgcttgccc ggtgccagta    3720
tgttgctctg acgcacgcgc agcacgcagc cgtgcttgtc ctggacattg atgtgccgag    3780
ccaccaggcc ggcgggaaaa tcgagcacgt aaacccgag gtctacgcga ttttggagcg     3840
ctgggcacgc ctggaaaaag cgccagcttg gatcggcgtg aatccactga gcgggaaatg    3900
ccagctcatc tggctcattg atccggtgta tgccgcagca ggcatgagca gcccgaatat    3960
gcgcctgctg gctgcaacga ccgaggaaat gacccgcgtt ttcggcgctg accaggcttt    4020
ttcacatagg ctgagccgtg gccactgcac tctccgacga tcccagccgt accgctggca    4080
tgcccagcac aatcgcgtgg atcgcctagc tgatcttatg gaggttgctc gcatgatctc    4140
aggcacagaa aaacctaaaa aacgctatga gcaggagttt tctagcggac gggcacgtat    4200
cgaagcggca agaaaagcca ctgcggaagc aaaagcactt gccacgcttg aagcaagcct    4260
gccgagcgcc gctgaagcgt ctggagagct gatcgacggc gtccgtgtcc tctggactgc    4320
tccagggcgt gccgcccgtg atgagacggc ttttcgccac gctttgactg tgggatacca    4380
gttaaaagcg gctggtgagc gcctaaaaga caccaagggt catcgagcct acgagcgtgc    4440
ctacaccgtc gctcaggcgg tcggaggagg ccgtgagcct gatctgccgc cggactgtga    4500
ccgccagacg gattggccgc gacgtgtgcg cggctacgtc gctaaaggcc agccagtcgt    4560
ccctgctcgt cagacagaga cgcagagcca gccgaggcga aaagctctgg ccactatggg    4620
aagacgtggc ggtaaaaagg ccgcagaacg ctggaaagac ccaaacagtg agtacgcccg    4680
agcacagcga gaaaaactag ctaagtccag tcaacgacaa gctaggaaag ctaaaggaaa    4740
tcgcttgacc attgcaggtt ggtttatgac tgttgaggga gagactggct cgtggccgac    4800
aatcaatgaa gctatgtctg aatttagcgt gtcacgtcag accgtgaata gagcacttaa    4860
ggtctgcggg cattgaactt ccacgaggac gccgaaagct tcccagtaaa tgtgccatct    4920
cgtaggcaga aaacgcttcc cccgtagggt ctctctcttg gcctcctttc taggtcgggc    4980
tgattgctct tgaagctctc taggggggct cacaccatag gcagataacg ttccccaccg    5040
gctcgcctcg taagcgcaca aggactgctc ccaaagatct tcaaagccac t             5091
```

<210> SEQ ID NO 58
<211> LENGTH: 4323
<212> TYPE: DNA
<213> ORGANISM: Artificial sequence
<220> FEATURE:
<223> OTHER INFORMATION: Description of the artificial sequence:plasmid

<400> SEQUENCE: 58

```
tctctcagcg tatggttgtc gcctgagctg tagttgcctt catcgatgaa ctgctgtaca      60
ttttgatacg tttttccgtc accgtcaaag attgatttat aatcctctac accgttgatg     120
ttcaaagagc tgtctgatgc tgatacgtta acttgtgcag ttgtcagtgt ttgtttgccg     180
taatgtttac cggagaaatc agtgtagaat aaacggattt ttccgtcaga tgtaaatgtg     240
gctgaacctg accattcttg tgtttggtct tttaggatag aatcatttgc atcgaatttg     300
tcgctgtctt taaagacgcg gccagcgttt ttccagctgt caatagaagt ttcgccgact     360
ttttgataga acatgtaaat cgatgtgtca tccgcatttt taggatctcc ggctaatgca     420
aagacgatgt ggtagccgtg atagtttgcg acagtgccgt cagcgttttg taatggccag     480
ctgtcccaaa cgtccaggcc ttttgcagaa gagatatttt taattgtgga cgaatcaaat     540
tcagaaactt gatatttttc atttttttgc tgttcaggga tttgcagcat atcatggcgt     600
gtaatatggg aaatgccgta tgtttcctta tatggctttt ggttcgtttc tttcgcaaac     660
gcttgagttg cgcctcctgc cagcagtgcg gtagtaaagg ttaatactgt tgcttgtttt     720
gcaaactttt tgatgttcat cgttcatgtc tccttttta tgtactgtgt tagcggtctg     780
cttcttccag ccctcctgtt tgaagatggc aagttagtta cgcacaataa aaaaagacct     840
aaaatatgta agggtgacg ccaaagtata cactttgccc tttacacatt ttaggtcttg     900
cctgctttat cagtaacaaa cccgcgcgat ttactttcg acctcattct attagactct     960
cgtttggatt gcaactggtc tatttcctc ttttgtttga tagaaaatca taaaaggatt    1020
tgcagactac gggcctaaag aactaaaaaa tctatctgtt tcttttcatt ctctgtattt    1080
tttatagttt ctgttgcatg gcataaagt tgccttttta atcacaattc agaaaatatc    1140
ataatatctc atttcactaa ataatagtga acggcaggta tatgtgatgg gttaaaaagg    1200
atcggcggcc gctcgattta aatctcgaga ggcctgacgt cgggcccggt accacgcgtc    1260
atatgactag ttcggaccta gggatatcgt cgacatcgat gctcttctgc gttaattaac    1320
aattgggatc ctctagaccc gggatttaaa tcgctagcgg gctgctaaag aagcggaac    1380
acgtagaaag ccagtccgca gaaacggtgc tgaccccgga tgaatgtcag ctactgggct    1440
atctggacaa gggaaaacgc aagcgcaaag agaaagcagg tagcttgcag tgggcttaca    1500
tggcgatagc tagactgggc ggttttatgg acagcaagcg aaccggaatt gccagctggg    1560
gcgccctctg gtaaggttgg gaagccctgc aaagtaaact ggatggcttt cttgccgcca    1620
aggatctgat ggcgcagggg atcaagatct gatcaagaga caggatgagg atcgtttcgc    1680
atgattgaac aagatggatt gcacgcaggt tctccggccg cttgggtgga gaggctattc    1740
ggctatgact gggcacaaca gacaatcggc tgctctgatg ccgccgtgtt ccggctgtca    1800
gcgcagggc gcccggttct ttttgtcaag accgacctgt ccggtgccct gaatgaactg    1860
caggacgagg cagcgcggct atcgtggctg gccacgacgg gcgttccttg cgcagctgtg    1920
ctcgacgttg tcactgaagc gggaagggac tggctgctat tgggcgaagt gccggggcag    1980
gatctcctgt catctcacct tgctcctgcc gagaaagtat ccatcatggc tgatgcaatg    2040
cggcggctgc atacgcttga tccggctacc tgcccattcg accaccaagc gaaacatcgc    2100
atcgagcgag cacgtactcg gatggaagcc ggtcttgtcg atcaggatga tctggacgaa    2160
gagcatcagg ggctcgcgcc agccgaactg ttcgccaggc tcaaggcgcg catgcccgac    2220
```

-continued

```
ggcgaggatc tcgtcgtgac ccatggcgat gcctgcttgc cgaatatcat ggtggaaaat    2280
ggccgctttt ctggattcat cgactgtggc cggctgggtg tggcggaccg ctatcaggac    2340
atagcgttgg ctacccgtga tattgctgaa gagcttggcg gcgaatgggc tgaccgcttc    2400
ctcgtgcttt acggtatcgc cgctcccgat tcgcagcgca tcgccttcta tcgccttctt    2460
gacgagttct tctgagcggg actctggggt tcgaaatgac cgaccaagcg acgcccaacc    2520
tgccatcacg agatttcgat tccaccgccg ccttctatga aggttgggc ttcggaatcg     2580
ttttccggga cgccggctgg atgatcctcc agcgcgggga tctcatgctg gagttcttcg    2640
cccacgctag cggcgcgccg gccggcccgg tgtgaaatac cgcacagatg cgtaaggaga    2700
aaataccgca tcaggcgctc ttccgcttcc tcgctcactg actcgctgcg ctcggtcgtt    2760
cggctgcggc gagcggtatc agctcactca aaggcggtaa tacggttatc cacagaatca    2820
ggggataacg caggaaagaa catgtgagca aaaggccagc aaaaggccag gaaccgtaaa    2880
aaggccgcgt tgctggcgtt tttccatagg ctccgccccc ctgacgagca tcacaaaaat    2940
cgacgctcaa gtcagaggtg gcgaaacccg acaggactat aaagatacca ggcgtttccc    3000
cctggaagct ccctcgtgcg ctctcctgtt ccgaccctgc cgcttaccgg atacctgtcc    3060
gcctttctcc cttcgggaag cgtggcgctt tctcatagct cacgctgtag gtatctcagt    3120
tcggtgtagg tcgttcgctc caagctgggc tgtgtgcacg aacccccgt tcagcccgac     3180
cgctgcgcct tatccggtaa ctatcgtctt gagtccaacc cggtaagaca cgacttatcg    3240
ccactggcag cagccactgg taacaggatt agcagagcga gtatgtagg cggtgctaca     3300
gagttcttga agtggtggcc taactacggc tacactagaa ggacagtatt tggtatctgc    3360
gctctgctga agccagttac cttcggaaaa agagttggta gctcttgatc cggcaaacaa    3420
accaccgctg gtagcggtgg tttttttgtt tgcaagcagc agattacgcg cagaaaaaaa    3480
ggatctcaag aagatccttt gatcttttct acggggtctg acgctcagtg gaacgaaaac    3540
tcacgttaag ggattttggt catgagatta tcaaaaagga tcttcaccta gatccttttta   3600
aaggccggcc gcggccgcca tcggcatttt cttttgcgtt tttatttgtt aactgttaat    3660
tgtccttgtt caaggatgct gtctttgaca acagatgttt cttgcctttt gatgttcagc    3720
aggaagctcg gcgcaaacgt tgattgtttg tctgcgtaga atcctctgtt tgtcatatag    3780
cttgtaatca cgacattgtt tcctttcgct tgaggtacag cgaagtgtga gtaagtaaag    3840
gttacatcgt taggatcaag atccattttt aacacaaggc cagttttgtt cagcggcttg    3900
tatgggccag ttaaagaatt agaaacataa ccaagcatgt aaatatcgtt agacgtaatg    3960
ccgtcaatcg tcattttga tccgcgggag tcagtgaaca ggtaccattt gccgttcatt     4020
ttaaagacgt tcgcgcgttc aatttcatct gttactgtgt tagatgcaat cagcggtttc    4080
atcactttt tcagtgtgta atcatcgttt agctcaatca taccgagagc gccgtttgct     4140
aactcagccg tgcgtttttt atcgctttgc agaagttttt gactttcttg acggaagaat    4200
gatgtgcttt tgccatagta tgctttgtta aataaagatt cttcgccttg gtagccatct    4260
tcagttccag tgtttgcttc aaatactaag tatttgtggc ctttatcttc tacgtagtga    4320
gga                                                                  4323
```

<210> SEQ ID NO 59
<211> LENGTH: 35
<212> TYPE: DNA
<213> ORGANISM: Artificial sequence
<220> FEATURE:
<223> OTHER INFORMATION: Description of the artificial sequence:PCR

```
                          Primer

<400> SEQUENCE: 59
gagagagaga cgcgtcccag tggctgagac gcatc                              35

<210> SEQ ID NO 60
<211> LENGTH: 34
<212> TYPE: DNA
<213> ORGANISM: Artificial sequence
<220> FEATURE:
<223> OTHER INFORMATION: Description of the artificial sequence:PCR
      Primer

<400> SEQUENCE: 60
ctctctctgt cgacgaattc aatcttacgg cctg                               34

<210> SEQ ID NO 61
<211> LENGTH: 5860
<212> TYPE: DNA
<213> ORGANISM: Artificial sequence
<220> FEATURE:
<223> OTHER INFORMATION: Description of the artificial sequence:plasmid

<400> SEQUENCE: 61
cccggtacca cgcgtcccag tggctgagac gcatccgcta aagccccagg aaccctgtgc     60
agaaagaaaa cactcctctg gctaggtaga cacagtttat aaaggtagag ttgagcgggt    120
aactgtcagc acgtagatcg aaaggtgcac aaaggtggcc ctggtcgtac agaaatatgg    180
cggttcctcg cttgagagtg cggaacgcat agaaacgtc gctgaacgga tcgttgccac     240
caagaaggct ggaaatgatg tcgtggttgt ctgctccgca atgggagaca ccacggatga    300
acttctagaa cttgcagcgg cagtgaatcc cgttccgcca gctcgtgaaa tggatatgct    360
cctgactgct ggtgagcgta tttctaacgc tctcgtcgcc atggctattg agtcccttgg    420
cgcagaagcc caatctttca cgggctctca ggctggtgtg ctcaccaccg agcgccacgg    480
aaacgcacgc attgttgatg tcactccagg tcgtgtgcgt gaagcactcg atgagggcaa    540
gatctgcatt gttgctggtt tccagggtgt taataaagaa acccgcgatg tcaccacgtt    600
gggtcgtggt ggttctgaca ccactgcagt tgcgttggca gctgctttga acgctgatgt    660
gtgtgagatt tactcggacg ttgacggtgt gtataccgct gacccgcgca tcgttcctaa    720
tgcacagaag ctggaaaagc tcagcttcga agaaatgctg aacttgctg ctgttggctc     780 caagattttg gtgctgcgca gtgttgaata cgctcgtgca ttcaatgtgc acttcgcgt     840 acgctcgtct tatagtaatg atcccggcac tttgattgcc ggctctatgg aggatattcc    900 tgtgaagaa gcagtcctta ccggtgtcgc aaccgacaag tccgaagcca agtaaccgt      960 tctgggtatt tccgataagc caggcgaggc tgcgaaggtt ttccgtgcgt tggctgatgc   1020
agaaatcaac attgacatgg ttctgcagaa cgtctcttct gtagaagacg gcaccaccga   1080
catcaccttc acctgccctc gttccgacgg ccgccgcgcg atggagatct tgaagaagct   1140
tcaggttcag ggcaactgga ccaatgtgct ttacgacgac caggtcggca agtctccct    1200 cgtgggtgct ggcatgaagt ctcacccagg tgttaccgca gagttcatgg aagctctgcg   1260
cgatgtcaac gtgaacatcg aattgatttc cacctctgag attcgtattt ccgtgctgat   1320
ccgtgaagat gatctggatg ctgctgcacg tgcattgcat gagcagttcc agctgggcgg   1380
cgaagacgaa gccgtcgttt atgcaggcac cggacgctaa agttttaaag gagtagttt    1440 acaatgacca ccatcgcagt tgttggtgca accggccagg tcggccaggt tatgcgcacc   1500
```

```
cttttggaag agcgcaattt cccagctgac actgttcgtt tctttgcttc cccacgttcc    1560
gcaggccgta agattgaatt cgtcgacatc gatgctcttc tgcgttaatt aacaattggg    1620
atcctctaga cccgggattt aaatcgctag cgggctgcta aaggaagcgg aacacgtaga    1680
aagccagtcc gcagaaacgg tgctgacccc ggatgaatgt cagctactgg gctatctgga    1740
caagggaaaa cgcaagcgca aagagaaagc aggtagcttg cagtgggctt acatggcgat    1800
agctagactg ggcggtttta tggacagcaa gcgaaccgga attgccagct ggggcgccct    1860
ctggtaaggt tgggaagccc tgcaaagtaa actggatggc tttcttgccg ccaaggatct    1920 gatgcgcag gggatcaaga tctgatcaag agacaggatg aggatcgttt cgcatgattg     1980
aacaagatgg attgcacgca ggttctccgg ccgcttgggt ggagaggcta ttcggctatg    2040
actgggcaca acagacaatc ggctgctctg atgccgccgt gttccggctg tcagcgcagg    2100
ggcgcccggt tctttttgtc aagaccgacc tgtccggtgc cctgaatgaa ctgcaggacg    2160
aggcagcgcg gctatcgtgg ctggccacga cgggcgttcc ttgcgcagct gtgctcgacg    2220
ttgtcactga agcgggaagg gactggctgc tattgggcga agtgccgggg caggatctcc    2280
tgtcatctca ccttgctcct gccgagaaag tatccatcat ggctgatgca atgcggcggc    2340
tgcatacgct tgatccggct acctgcccat tcgaccacca agcgaaacat cgcatcgagc    2400
gagcacgtac tcggatggaa gccggtcttg tcgatcagga tgatctggac gaagagcatc    2460
aggggctcgc gccagccgaa ctgttcgcca ggctcaaggc gcgcatgccc gacggcgagg    2520
atctcgtcgt gacccatggc gatgcctgct tgccgaatat catggtggaa aatggccgct    2580
tttctggatt catcgactgt ggccggctgg gtgtggcgga ccgctatcag gacatagcgt    2640
tggctacccg tgatattgct gaagagcttg gcggcgaatg ggctgaccgc ttcctcgtgc    2700
tttacggtat cgccgctccc gattcgcagc gcatcgcctt ctatcgcctt cttgacgagt    2760
tcttctgagc gggactctgg ggttcgaaat gaccgaccaa gcgacgccca acctgccatc    2820
acgagatttc gattccaccg ccgccttcta tgaaaggttg gcttcggaa tcgttttccg     2880 ggacgccggc tggatgatcc tccagcgcgg ggatctcatg ctggagttct cgcccacgc     2940 tagcggcgcg ccggccggcc cggtgtgaaa taccgcacag atgcgtaagg agaaaatacc    3000
gcatcaggcg ctcttccgct tcctcgctca ctgactcgct gcgctcggtc gttcggctgc    3060
ggcgagcggt atcagctcac tcaaaggcgg taatacggtt atccacagaa tcaggggata    3120
acgcaggaaa gaacatgtga gcaaaaggcc agcaaaaggc caggaaccgt aaaaaggccg    3180
cgttgctggc gttttccat aggctccgcc ccctgacga gcatcacaaa aatcgacgct     3240
caagtcagag gtggcgaaac ccgacaggac tataaagata ccaggcgttt ccccctggaa    3300
gctccctcgt gcgctctcct gttccgaccc tgccgcttac cggatacctg tccgcctttc    3360
tcccttcggg aagcgtggcg ctttctcata gctcacgctg taggtatctc agttcggtgt    3420
aggtcgttcg ctccaagctg ggctgtgtgc acgaaccccc cgttcagccc gaccgctgcg    3480
ccttatccgg taactatcgt cttgagtcca acccggtaag acacgactta tcgccactgg    3540
cagcagccac tggtaacagg attagcagag cgaggtatgt aggcggtgct acagagttct    3600
tgaagtggtg gcctaactac ggctacacta aaggacagt atttggtatc tgcgctctgc     3660
tgaagccagt taccttcgga aaagagttg gtagctcttg atccggcaaa caaaccaccg     3720
ctggtagcgg tggttttttt gtttgcaagc agcagattac gcgcagaaaa aaggatctc     3780 aagaagatcc tttgatcttt tctacggggt ctgacgctca gtggaacgaa aactcacgtt    3840
aagggatttt ggtcatgaga ttatcaaaaa ggatcttcac ctagatcctt ttaaaggccg    3900
```

```
gccgcggccg ccatcggcat tttcttttgc gttttattt gttaactgtt aattgtcctt      3960
gttcaaggat gctgtctttg acaacagatg ttttcttgcc tttgatgttc agcaggaagc      4020
tcggcgcaaa cgttgattgt tgtctgcgt agaatcctct gtttgtcata tagcttgtaa       4080
tcacgacatt gtttcctttc gcttgaggta cagcgaagtg tgagtaagta aaggttacat      4140
cgttaggatc aagatccatt tttaacacaa ggccagtttt gttcagcggc ttgtatgggc      4200
cagttaaaga attagaaaca taaccaagca tgtaaatatc gttagacgta atgccgtcaa      4260
tcgtcatttt tgatccgcgg gagtcagtga acaggtacca tttgccgttc attttaaaga     4320
cgttcgcgcg ttcaatttca tctgttactg tgttagatgc aatcagcggt ttcatcactt     4380
ttttcagtgt gtaatcatcg tttagctcaa tcataccgag agcgccgttt gctaactcag     4440
ccgtgcgttt tttatcgctt tgcagaagtt tttgactttc ttgacggaag aatgatgtgc     4500
ttttgccata gtatgctttg ttaaataaag attcttcgcc ttggtagcca tcttcagttc     4560
cagtgtttgc ttcaaatact aagtatttgt ggcctttatc ttctacgtag tgaggatctc     4620
tcagcgtatg gttgtcgcct gagctgtagt tgccttcatc gatgaactgc tgtacatttt     4680
gatacgtttt tccgtcaccg tcaaagattg atttataatc ctctacaccg ttgatgttca     4740
aagagctgtc tgatgctgat acgttaactt gtgcagttgt cagtgtttgt ttgccgtaat     4800
gtttaccgga gaaatcagtg tagaataaac ggattttttcc gtcagatgta aatgtggctg    4860
aacctgacca ttcttgtgtt tggtctttta ggatagaatc atttgcatcg aatttgtcgc     4920
tgtctttaaa gacgcggcca gcgttttttcc agctgtcaat agaagtttcg ccgacttttt   4980
gatagaacat gtaaatcgat gtgtcatccg catttttagg atctccggct aatgcaaaga     5040
cgatgtggta gccgtgatag tttgcgacag tgccgtcagc gttttgtaat ggccagctgt     5100
cccaaacgtc caggccttttt gcagaagaga tattttttaat tgtggacgaa tcaaattcag   5160
aaacttgata ttttttcattt ttttgctgtt cagggatttg cagcatatca tggcgtgtaa   5220
tatgggaaat gccgtatgtt tccttatatg gcttttggtt cgtttctttc gcaaacgctt     5280
gagttgcgcc tcctgccagc agtgcggtag taaaggttaa tactgttgct tgttttgcaa     5340 acttttttgat gttcatcgtt catgtctcct tttttatgta ctgtgttagc ggtctgcttc   5400 ttccagcccct cctgtttgaa gatggcaagt tagttacgca caataaaaaa agacctaaaa   5460
tatgtaaggg gtgacgccaa agtatacact ttgcccttta cacattttag gtcttgcctg     5520
ctttatcagt aacaaacccg cgcgatttac ttttcgacct cattctatta gactctcgtt     5580
tggattgcaa ctggtctatt ttcctctttt gtttgataga aaatcataaa aggatttgca     5640
gactacgggc ctaaagaact aaaaaatcta tctgtttctt ttcattctct gtatttttta    5700
tagtttctgt tgcatgggca taaagttgcc tttttaatca caattcagaa aatatcataa    5760
tatctcattt cactaaataa tagtgaacgg caggtatatg tgatgggtta aaaaggatcg     5820
gcggccgctc gatttaaatc tcgagaggcc tgacgtcggg                          5860
```

<210> SEQ ID NO 62
<211> LENGTH: 38
<212> TYPE: DNA
<213> ORGANISM: Artificial sequence
<220> FEATURE:
<223> OTHER INFORMATION: Description of the artificial sequence:PCR Primer
<400> SEQUENCE: 62

```
cggcaccacc gacatcatct tcacctgccc tcgttccg                              38
```

<210> SEQ ID NO 63
<211> LENGTH: 38
<212> TYPE: DNA
<213> ORGANISM: Artificial sequence
<220> FEATURE:
<223> OTHER INFORMATION: Description of the artificial sequence:PCR Primer

<400> SEQUENCE: 63

```
cggaacgagg gcaggtgaag atgatgtcgg tggtgccg                              38
```

<210> SEQ ID NO 64
<211> LENGTH: 1266
<212> TYPE: DNA
<213> ORGANISM: LysC mutant
<220> FEATURE:
<221> NAME/KEY: CDS
<222> LOCATION: (1)..(1266)

<400> SEQUENCE: 64

```
gtg gcc ctg gtc gta cag aaa tat ggc ggt tcc tcg ctt gag agt gcg     48
Val Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct     96
Glu Arg Ile Arg Asn Val Ala Glu Arg Ile Val Ala Thr Lys Lys Ala
            20                  25                  30 gga aat gat gtc gtg gtt gtc tgc tcc gca atg gga gac acc acg gat   144
Gly Asn Asp Val Val Val Val Cys Ser Ala Met Gly Asp Thr Thr Asp
        35                  40                  45 gaa ctt cta gaa ctt gca gcg gca gtg aat ccc gtt ccg cca gct cgt   192
Glu Leu Leu Glu Leu Ala Ala Ala Val Asn Pro Val Pro Pro Ala Arg
    50                  55                  60 gaa atg gat atg ctc ctg act gct ggt gag cgt att tct aac gct ctc   240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg   288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc   336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc   384
Ile Val Asp Val Thr Pro Gly Arg Val Arg Glu Ala Leu Asp Glu Gly
        115                 120                 125 aag atc tgc att gtt gct ggt ttc cag ggt gtt aat aaa gaa acc cgc   432
Lys Ile Cys Ile Val Ala Gly Phe Gln Gly Val Asn Lys Glu Thr Arg
    130                 135                 140 gat gtc acc acg ttg ggt cgt ggt ggt tct gac acc act gca gtt gcg   480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt   528
Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag   576
Asp Gly Val Tyr Thr Ala Asp Pro Arg Ile Val Pro Asn Ala Gln Lys
            180                 185                 190 ctg gaa aag ctc agc ttc gaa gaa atg ctg gaa ctt gct gct gtt ggc   624
Leu Glu Lys Leu Ser Phe Glu Glu Met Leu Glu Leu Ala Ala Val Gly
        195                 200                 205 tcc aag att ttg gtg ctg cgc agt gtt gaa tac gct cgt gca ttc aat   672
Ser Lys Ile Leu Val Leu Arg Ser Val Glu Tyr Ala Arg Ala Phe Asn
    210                 215                 220
```

```
gtg cca ctt cgc gta cgc tcg tct tat agt aat gat ccc ggc act ttg      720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc      768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att      816
Gly Val Ala Thr Asp Lys Ser Glu Ala Lys Val Thr Val Leu Gly Ile
            260                 265                 270 tcc gat aag cca ggc gag gct gcg aag gtt ttc cgt gcg ttg gct gat      864
Ser Asp Lys Pro Gly Glu Ala Ala Lys Val Phe Arg Ala Leu Ala Asp
        275                 280                 285 gca gaa atc aac att gac atg gtt ctg cag aac gtc tct tct gta gaa      912
Ala Glu Ile Asn Ile Asp Met Val Leu Gln Asn Val Ser Ser Val Glu
    290                 295                 300 gac ggc acc acc gac atc atc ttc acc tgc cct cgt tcc gac ggc cgc      960
Asp Gly Thr Thr Asp Ile Ile Phe Thr Cys Pro Arg Ser Asp Gly Arg
305                 310                 315                 320 cgc gcg atg gag atc ttg aag aag ctt cag gtt cag ggc aac tgg acc     1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct     1056
Asn Val Leu Tyr Asp Asp Gln Val Gly Lys Val Ser Leu Val Gly Ala
                340                 345                 350 ggc atg aag tct cac cca ggt gtt acc gca gag ttc atg gaa gct ctg     1104
Gly Met Lys Ser His Pro Gly Val Thr Ala Glu Phe Met Glu Ala Leu
            355                 360                 365 cgc gat gtc aac gtg aac atc gaa ttg att tcc acc tct gag att cgt     1152
Arg Asp Val Asn Val Asn Ile Glu Leu Ile Ser Thr Ser Glu Ile Arg
        370                 375                 380 att tcc gtg ctg atc cgt gaa gat gat ctg gat gct gct gca cgt gca     1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat     1248
Leu His Glu Gln Phe Gln Leu Gly Gly Glu Asp Glu Ala Val Val Tyr
                405                 410                 415 gca ggc acc gga cgc taa                                             1266
Ala Gly Thr Gly Arg
            420

<210> SEQ ID NO 65
<211> LENGTH: 421
<212> TYPE: PRT
<213> ORGANISM: LysC mutant

<400> SEQUENCE: 65

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
                20                  25                  30

Gly Asn Asp Val Val Val Cys Ser Ala Met Gly Asp Thr Thr Asp
            35                  40                  45

Glu Leu Leu Glu Leu Ala Ala Val Asn Pro Val Pro Pro Ala Arg
        50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95
```

```
Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Ile Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 66
<211> LENGTH: 5860
<212> TYPE: DNA
<213> ORGANISM: Artificial sequence
<220> FEATURE:
<223> OTHER INFORMATION: Description of the artificial sequence:plasmid

<400> SEQUENCE: 66
cccggtacca cgcgtcccag tggctgagac gcatccgcta aagccccagg aaccctgtgc        60
agaaagaaaa cactcctctg gctaggtaga cacagtttat aaaggtagag ttgagcgggt       120
aactgtcagc acgtagatcg aaaggtgcac aaaggtggcc ctggtcgtac agaaatatgg       180
```

```
cggttcctcg cttgagagtg cggaacgcat tagaaacgtc gctgaacgga tcgttgccac    240
caagaaggct ggaaatgatg tcgtggttgt ctgctccgca atgggagaca ccacggatga    300
acttctagaa cttgcagcgg cagtgaatcc cgttccgcca gctcgtgaaa tggatatgct    360
cctgactgct ggtgagcgta tttctaacgc tctcgtcgcc atggctattg agtcccttgg    420
cgcagaagcc caatctttca cgggctctca ggctggtgtg ctcaccaccg agcgccacgg    480
aaacgcacgc attgttgatg tcactccagg tcgtgtgcgt gaagcactcg atgagggcaa    540
gatctgcatt gttgctggtt tccagggtgt taataaagaa acccgcgatg tcaccacgtt    600
gggtcgtggt ggttctgaca ccactgcagt tgcgttggca gctgctttga acgctgatgt    660
gtgtgagatt tactcggacg ttgacggtgt gtataccgct gacccgcgca tcgttcctaa    720
tgcacagaag ctgaaaaagc tcagcttcga agaaatgctg gaacttgctg ctgttggctc    780
caagattttg gtgctgcgca gtgttgaata cgctcgtgca ttcaatgtgc cacttcgcgt    840
acgctcgtct tatagtaatg atcccggcac tttgattgcc ggctctatgg aggatattcc    900
tgtggaagaa gcagtcctta ccggtgtcgc aaccgacaag tccgaagcca agtaaccgt     960 tctgggtatt tccgataagc caggcgaggc tgcgaaggtt ttccgtgcgt tggctgatgc    1020
agaaatcaac attgacatgg ttctgcagaa cgtctcttct gtagaagacg gcaccaccga    1080
catcatcttc acctgccctc gttccgacgg ccgccgcgcg atggagatct gaagaagct     1140 tcaggttcag ggcaactgga ccaatgtgct ttacgacgac caggtcggca agtctccct     1200 cgtgggtgct ggcatgaagt ctcacccagg tgttaccgca gagttcatgg aagctctgcg    1260
cgatgtcaac gtgaacatcg aattgatttc cacctctgag attcgtattt ccgtgctgat    1320
ccgtgaagat gatctggatg ctgctgcacg tgcattgcat gagcagttcc agctgggcgg    1380
cgaagacgaa gccgtcgttt atgcaggcac cggacgctaa agttttaaag gagtagtttt    1440
acaatgacca ccatcgcagt tgttggtgca accggccagg tcggccaggt tatgcgcacc    1500
cttttggaag agcgcaattt cccagctgac actgttcgtt tctttgcttc cccacgttcc    1560
gcaggccgta agattgaatt cgtcgacatc gatgctcttc tgcgttaatt aacaattggg    1620
atcctctaga cccgggattt aaatcgctag cgggctgcta aggaagcgg aacacgtaga    1680 aagccagtcc gcagaaacgg tgctgacccc ggatgaatgt cagctactgg gctatctgga    1740
caagggaaaa cgcaagcgca aagagaaagc aggtagcttg cagtgggctt acatggcgat    1800
agctagactg gcggtttta tggacagcaa gcgaaccgga attgccagct ggggcgccct    1860
ctggtaaggt tgggaagccc tgcaaagtaa actggatggc tttcttgccg ccaaggatct    1920
gatggcgcag gggatcaaga tctgatcaag agacaggatg aggatcgttt cgcatgattg    1980
aacaagatgg attgcacgca ggttctccgg ccgcttgggt ggagaggcta ttcggctatg    2040
actgggcaca acagacaatc ggctgctctg atgccgccgt gttccggctg tcagcgcagg    2100
ggcgcccggt tctttttgtc aagaccgacc tgtccggtgc cctgaatgaa ctgcaggacg    2160
aggcagcgcg gctatcgtgg ctggccacga cgggcgttcc ttgcgcagct gtgctcgacg    2220
ttgtcactga agcgggaagg gactggctgc tattgggcga agtgccgggg caggatctcc    2280
tgtcatctca ccttgctcct gccgagaaag tatccatcat ggctgatgca atgcggcggc    2340
tgcatacgct tgatccggct acctgcccat tcgaccacca agcgaaacat cgcatcgagc    2400
gagcacgtac tcggatggaa gccggtcttg tcgatcagga tgatctggac gaagagcatc    2460
aggggctcgc gccagccgaa ctgttcgcca ggctcaaggc gcgcatgccc gacgcgagg     2520 atctcgtcgt gacccatggc gatgcctgct tgccgaatat catggtggaa aatggccgct    2580
```

-continued

| | |
|---|---|
| tttctggatt catcgactgt ggccggctgg gtgtggcgga ccgctatcag gacatagcgt | 2640 |
| tggctacccg tgatattgct gaagagcttg gcggcgaatg ggctgaccgc ttcctcgtgc | 2700 |
| tttacggtat cgccgctccc gattcgcagc gcatcgcctt ctatcgcctt cttgacgagt | 2760 |
| tcttctgagc gggactctgg ggttcgaaat gaccgaccaa gcgacgccca acctgccatc | 2820 |
| acgagatttc gattccaccg ccgccttcta tgaaaggttg ggcttcggaa tcgttttccg | 2880 |
| ggacgccggc tggatgatcc tccagcgcgg ggatctcatg ctggagttct tcgcccacgc | 2940 |
| tagcggcgcg ccgccggcc cggtgtgaaa taccgcacag atgcgtaagg agaaaatacc | 3000 |
| gcatcaggcg ctcttccgct tcctcgctca ctgactcgct gcgctcggtc gttcggctgc | 3060 |
| ggcgagcggt atcagctcac tcaaaggcgg taatacggtt atccacagaa tcaggggata | 3120 |
| acgcaggaaa gaacatgtga gcaaaaggcc agcaaaaggc caggaaccgt aaaaaggccg | 3180 |
| cgttgctggc gtttttccat aggctccgcc cccctgacga gcatcacaaa aatcgacgct | 3240 |
| caagtcagag gtggcgaaac ccgacaggac tataaagata ccaggcgttt ccccctggaa | 3300 |
| gctccctcgt gcgctctcct gttccgaccc tgccgcttac cggatacctg tccgcctttc | 3360 |
| tcccttcggg aagcgtggcg ctttctcata gctcacgctg taggtatctc agttcggtgt | 3420 |
| aggtcgttcg ctccaagctg ggctgtgtgc acgaaccccc cgttcagccc gaccgctgcg | 3480 |
| ccttatccgg taactatcgt cttgagtcca acccggtaag acacgactta tcgccactgg | 3540 |
| cagcagccac tggtaacagg attagcagag cgaggtatgt aggcggtgct acagagttct | 3600 |
| tgaagtggtg gcctaactac ggctacacta gaaggacagt atttggtatc tgcgctctgc | 3660 |
| tgaagccagt taccttcgga aaaagagttg gtagctcttg atccggcaaa caaaccaccg | 3720 |
| ctggtagcgg tggttttttt gtttgcaagc agcagattac gcgcagaaaa aaaggatctc | 3780 |
| aagaagatcc tttgatcttt tctacggggt ctgacgctca gtggaacgaa aactcacgtt | 3840 |
| aagggatttt ggtcatgaga ttatcaaaaa ggatcttcac ctagatcctt ttaaaggccg | 3900 |
| gccgcggccg ccatcggcat tttcttttgc gttttattt gttaactgtt aattgtcctt | 3960 |
| gttcaaggat gctgtctttg acaacagatg ttttcttgcc tttgatgttc agcaggaagc | 4020 |
| tcggcgcaaa cgttgattgt ttgtctgcgt agaatcctct gtttgtcata tagcttgtaa | 4080 |
| tcacgacatt gtttccttc gcttgaggta cagcgaagtg tgagtaagta aaggttacat | 4140 |
| cgttaggatc aagatccatt tttaacacaa ggccagtttt gttcagcggc ttgtatgggc | 4200 |
| cagtaaaga attagaaaca taaccaagca tgtaaatatc gttagacgta atgccgtcaa | 4260 |
| tcgtcatttt tgatccgcgg gagtcagtga acaggtacca tttgccgttc attttaaaga | 4320 |
| cgttcgcgcg ttcaatttca tctgttactg tgttagatgc aatcagcggt ttcatcactt | 4380 |
| ttttcagtgt gtaatcatcg tttagctcaa tcataccgag agcgccgttt gctaactcag | 4440 |
| ccgtgcgttt tttatcgctt tgcagaagtt tttgactttc ttgacggaag aatgatgtgc | 4500 |
| ttttgccata gtatgctttg ttaaataaag attcttcgcc ttggtagcca tcttcagttc | 4560 |
| cagtgttgc ttcaaatact aagtatttgt ggcctttatc ttctacgtag tgaggatctc | 4620 |
| tcagcgtatg gttgtcgcct gagctgtagt tgccttcatc gatgaactgc tgtacatttt | 4680 |
| gatacgtttt tccgtcaccg tcaaagatt atttataatc ctctacaccg ttgatgttca | 4740 |
| aagagctgtc tgatgctgat acgttaactt gtgcagttgt cagtgtttgt ttgccgtaat | 4800 |
| gtttaccgga gaaatcagtg tagaataaac ggatttttcc gtcagatgta aatgtggctg | 4860 |
| aacctgacca ttcttgtgtt tggtctttta ggatagaatc atttgcatcg aatttgtcgc | 4920 |

-continued

```
tgtctttaaa gacgcggcca gcgttttcc agctgtcaat agaagtttcg ccgactttt        4980 gatagaacat gtaaatcgat gtgtcatccg cattttagg atctccggct aatgcaaaga        5040
cgatgtggta gccgtgatag tttgcgacag tgccgtcagc gttttgtaat ggccagctgt      5100
cccaaacgtc caggcctttt gcagaagaga tattttaat tgtggacgaa tcaaattcag       5160
aaacttgata tttttcattt ttttgctgtt cagggatttg cagcatatca tggcgtgtaa      5220
tatgggaaat gccgtatgtt tccttatatg gcttttggtt cgtttctttc gcaaacgctt     5280
gagttgcgcc tcctgccagc agtgcggtag taaaggttaa tactgttgct tgttttgcaa      5340 acttttgat gttcatcgtt catgtctcct ttttatgta ctgtgttagc ggtctgcttc        5400
ttccagccct cctgtttgaa gatggcaagt tagttacgca caataaaaaa agacctaaaa     5460
tatgtaaggg gtgacgccaa agtatacact ttgcccttta cacattttag gtcttgcctg     5520
ctttatcagt aacaaacccg cgcgatttac ttttcgacct cattctatta gactctcgtt     5580
tggattgcaa ctggtctatt ttcctctttt gtttgataga aaatcataaa aggatttgca     5640
gactacgggc ctaaagaact aaaaaatcta tctgtttctt ttcattctct gtatttttta     5700
tagtttctgt tgcatgggca taagttgcc tttttaatca caattcagaa aatatcataa      5760
tatctcattt cactaaataa tagtgaacgg caggtatatg tgatgggtta aaaaggatcg     5820
gcggccgctc gatttaaatc tcgagaggcc tgacgtcggg                            5860
```

<210> SEQ ID NO 67
<211> LENGTH: 29
<212> TYPE: DNA
<213> ORGANISM: Artificial sequence
<220> FEATURE:
<223> OTHER INFORMATION: Description of the artificial sequence:PCR
      primer

<400> SEQUENCE: 67

```
gagactcgag gttggctggt catcatagg                                        29
```

<210> SEQ ID NO 68
<211> LENGTH: 34
<212> TYPE: DNA
<213> ORGANISM: Artificial sequence
<220> FEATURE:
<223> OTHER INFORMATION: Description of the artificial sequence:PCR
      primer

<400> SEQUENCE: 68

```
gaagagagca tatgtcagcg ctctagtttg gttc                                  34
```

<210> SEQ ID NO 69
<211> LENGTH: 6472
<212> TYPE: DNA
<213> ORGANISM: Artificial sequence
<220> FEATURE:
<223> OTHER INFORMATION: Description of the artificial sequence:plasmid

<400> SEQUENCE: 69

```
tcgaggttgg ctggtcatca taggaatcaa cctggccact ttatggtggg caccaccgtc      60
gcaaacaaca tatcttgcag caggcgtgtc gattctttcc gccatcattg tttggtttct     120
tcccggcgca cacccgctat ggaatcgccg tcgcattgct tcacgcaaac aacagtccac     180
cggtagacgt cgacaagccc ccaaacgatc aagccaccct caaacggcgg aatttagcca     240
acaacaatag actagacaga gctgtccatg tagcatgaac tcgattatca actgccacga     300
gaggtcgggg tcatgctcac caccacaggg acgctcacgc accaaaaaat cggagacttt     360
```

-continued

```
tacaccgaag ccggagcgac gcttcacgac gtaaccatcg cctaccaagc atggggccac    420
tacaccggca ccaatctcat cgttctcgaa catgccctga ccggcgactc taacgctatt    480
tcatggtggg acggactgat tggccctggc aaagcactcg acaccaaccg ctactgcatc    540
ctatgcacca acgtgctcgg aggatgcaaa ggatccaccg gaccgagcag tccacaccca    600
gacgaaaaac catggggatc cagatttcca gcccttcaa tccgtgacct tgtcaatgcc    660
gaaaaacaac ttttcgacca cctcggcatc aataaaattc acgcaatcat cggcggatcc    720
atgggaggcg cacgcaccct cgaatgggct gcactccacc cacacatgat gacgactgga    780
ttcgtcatag cagtctcagc acgcgcaagc gcttggcaaa tcggtattca aactgcacaa    840
atcagcgcca tagaactcga cccccactgg aacggcggcg attactacag cggtcacgca    900
ccatgggaag gaatcgccgc cgctcgccgg atcgcccacc tcacctatcg cggcgaacta    960
gaaatagacg aacgattcgg cacttccgca caacacggtg aaaacccact cggccccttc   1020
cgagatccac atcaacgttt tgcggtcacg agctacctcc aacaccaagg catcaaactc   1080
gctcaacgat tcgatgcagg tagttacgtc gtgcttaccg aagccctcaa tcgtcatgac   1140
atcggacgcg gccgaggcgg actcaacaaa gccctcagcg caatcacagt ccccatcatg   1200
attgctggcg ttgataccga tattctctac ccctatcacc agcaagaaca cctatcacga   1260
aatctaggca acctactcgc tatggcaaaa atcagctcac cagtaggcca cgacgctttc   1320
ctcacagaat tccgacaaat ggagcgaatc ctaagacatt tcatggagct ttcggaagga   1380
atcgacgatt ccttccgaac caaactagag cgctgacata tgactagttc ggacctaggg   1440
atatcgtcga catcgatgct cttctgcgtt aattaacaat tgggatcctc tagacccggg   1500
atttaaatcg ctagcgggct gctaaaggaa gcggaacacg tagaaagcca gtccgcagaa   1560
acggtgctga ccccggatga atgtcagcta ctgggctatc tggacaaggg aaaacgcaag   1620
cgcaaagaga aagcaggtag cttgcagtgg gcttacatgg cgatagctag actgggcggt   1680
tttatggaca gcaagcgaac cggaattgcc agctggggcg ccctctggta aggttgggaa   1740
gccctgcaaa gtaaactgga tggctttctt gccgccaagg atctgatggc cagggatc   1800 aagatctgat caagagacag gatgaggatc gtttcgcatg attgaacaag atggattgca   1860
cgcaggttct ccgccgcttg ggtggagag ctattcggc tatgactggg cacaacagac   1920
aatcggctgc tctgatgccg ccgtgttccg gctgtcagcg caggggcgcc cggttctttt   1980
tgtcaagacc gacctgtccg gtgccctgaa tgaactgcag gacgaggcag cgcggctatc   2040
gtggctggcc acgacgggcg ttccttgcgc agctgtgctc gacgttgtca ctgaagcggg   2100
aagggactgg ctgctattgg gcgaagtgcc ggggcaggat ctcctgtcat ctcaccttgc   2160
tcctgccgag aaagtatcca tcatggctga tgcaatgcgg cggctgcata cgcttgatcc   2220
ggctacctgc ccattcgacc accaagcgaa acatcgcatc gagcgagcac gtactcggat   2280
ggaagccggt cttgtcgatc aggatgatct ggacgaagag catcaggggc tcgcgccagc   2340
cgaactgttc gccaggctca aggcgcgcat gcccgacggc gaggatctcg tcgtgaccca   2400
tggcgatgcc tgcttgccga atatcatggt ggaaaatggc cgcttttctg gattcatcga   2460
ctgtggccgg ctgggtgtgg cggaccgcta tcaggacata gcgttggcta cccgtgatat   2520
tgctgaagag cttggcggcg aatgggctga ccgcttcctc gtgctttacg gtatcgccgc   2580
tcccgattcg cagcgcatcg ccttctatcg ccttcttgac gagttcttct gagcgggact   2640
ctggggttcg aaatgaccga ccaagcgacg cccaacctgc catcacgaga tttcgattcc   2700
```

-continued

```
accgccgcct tctatgaaag gttgggcttc ggaatcgttt tccgggacgc cggctggatg    2760
atcctccagc gcggggatct catgctggag ttcttcgccc acgctagcgg cgcgccggcc    2820
ggcccggtgt gaaataccgc acagatgcgt aaggagaaaa taccgcatca ggcgctcttc    2880
cgcttcctcg ctcactgact cgctgcgctc ggtcgttcgg ctgcggcgag cggtatcagc    2940
tcactcaaag gcggtaatac ggttatccac agaatcaggg gataacgcag gaaagaacat    3000
gtgagcaaaa ggccagcaaa aggccaggaa ccgtaaaaag gccgcgttgc tggcgttttt    3060
ccataggctc cgcccccctg acgagcatca caaaaatcga cgctcaagtc agaggtggcg    3120
aaacccgaca ggactataaa gataccaggc gtttccccct ggaagctccc tcgtgcgctc    3180
tcctgttccg accctgccgc ttaccggata cctgtccgcc tttctccctt cgggaagcgt    3240
ggcgctttct catagctcac gctgtaggta tctcagttcg gtgtaggtcg ttcgctccaa    3300
gctgggctgt gtgcacgaac cccccgttca gcccgaccgc tgcgccttat ccggtaacta    3360
tcgtcttgag tccaacccgg taagacacga cttatcgcca ctggcagcag ccactggtaa    3420
caggattagc agagcgaggt atgtaggcgg tgctacagag ttcttgaagt ggtggcctaa    3480
ctacggctac actagaagga cagtatttgg tatctgcgct ctgctgaagc cagttacctt    3540
cggaaaaaga gttggtagct cttgatccgg caaacaaacc accgctggta gcggtggttt    3600
ttttgtttgc aagcagcaga ttacgcgcag aaaaaaagga tctcaagaag atcctttgat    3660
cttttctacg gggtctgacg ctcagtggaa cgaaaactca cgttaaggga ttttggtcat    3720
gagattatca aaaaggatct tcacctagat ccttttaaag gccggccgcg gccgcgcaaa    3780
gtcccgcttc gtgaaaattt tcgtgccgcg tgattttccg ccaaaaactt taacgaacgt    3840
tcgttataat ggtgtcatga ccttcacgac gaagtactaa aattggcccg aatcatcagc    3900
tatggatctc tctgatgtcg cgctggagtc cgacgcgctc gatgctgccg tcgatttaaa    3960
aacggtgatc ggattttttcc gagctctcga tacgacggac gcgccagcat cacgagactg    4020
ggccagtgcc gcgagcgacc tagaaactct cgtggcggat cttgaggagc tggctgacga    4080
gctgcgtgct cggccagcgc caggaggacg cacagtagtg gaggatgcaa tcagttgcgc    4140
ctactgcggt ggcctgattc ctccccggcc tgacccgcga ggacggcgcg caaaatattg    4200
ctcagatgcg tgtcgtgccg cagccagccg cgagcgcgcc aacaaacgcc acgccgagga    4260
gctggaggcg gctaggtcgc aaatggcgct ggaagtgcgt cccccgagcg aaattttggc    4320
catggtcgtc acagagctgg aagcggcagc gagaattatc gcgatcgtgg cggtgcccgc    4380
aggcatgaca aacatcgtaa atgccgcgtt tcgtgtgccg tggccgccca ggacgtgtca    4440
gcgccgccac cacctgcacc gaatcggcag cagcgtcgcg cgtcgaaaaa gcgcacaggc    4500
ggcaagaagc gataagctgc acgaatacct gaaaaatgtt gaacgccccg tgagcggtaa    4560
ctcacagggc gtcggctaac ccccagtcca aacctgggag aaagcgctca aaaatgactc    4620
tagcggattc acgagacatt gacacaccgg cctggaaatt ttccgctgat ctgttcgaca    4680
cccatcccga gctcgcgctg cgatcacgtg gctggacgag cgaagaccgc gcgaattcc    4740 tcgctcacct gggcagagaa aatttccagg gcagcaagac ccgcgacttc gccagcgctt    4800
ggatcaaaga cccggacacg gagaaacaca gccgaagtta taccgagttg gttcaaaatc    4860
gcttgcccgt gccagtatg ttgctctgac gcacgcgcag cacgcagccg tgcttgtcct    4920
ggacattgat gtgccgagcc accaggccgg cgggaaaatc gagcacgtaa accccgaggt    4980
ctacgcgatt ttggagcgct gggcacgcct ggaaaaagcg ccagcttgga tcggcgtgaa    5040
tccactgagc gggaaatgcc agctcatctg gctcattgat ccggtgtatg ccgcagcagg    5100
```

```
catgagcagc ccgaatatgc gcctgctggc tgcaacgacc gaggaaatga cccgcgtttt    5160
cggcgctgac caggctttt cacataggct gagccgtggc cactgcactc tccgacgatc    5220
ccagccgtac cgctggcatg cccagcacaa tcgcgtggat cgcctagctg atcttatgga    5280
ggttgctcgc atgatctcag gcacagaaaa acctaaaaaa cgctatgagc aggagttttc    5340
tagcggacgg gcacgtatcg aagcggcaag aaaagccact gcggaagcaa aagcacttgc    5400
cacgcttgaa gcaagcctgc cgagcgccgc tgaagcgtct ggagagctga tcgacggcgt    5460
ccgtgtcctc tggactgctc cagggcgtgc cgcccgtgat gagacggctt ttcgccacgc    5520
tttgactgtg ggataccagt taaaagcggc tggtgagcgc ctaaaagaca ccaagggtca    5580
tcgagcctac gagcgtgcct acaccgtcgc tcaggcggtc ggaggaggcc gtgagcctga    5640
tctgccgccg gactgtgacc gccagacgga ttggccgcga cgtgtgcgcg gctacgtcgc    5700
taaaggccag ccagtcgtcc ctgctcgtca gacagagacg cagagccagc cgaggcgaaa    5760
agctctggcc actatgggaa gacgtggcgg taaaaaggcc gcagaacgct ggaaagaccc    5820
aaacagtgag tacgcccgag cacagcgaga aaaactagct aagtccagtc aacgacaagc    5880
taggaaagct aaaggaaatc gcttgaccat tgcaggttgg tttatgactg ttgagggaga    5940
gactggctcg tggccgacaa tcaatgaagc tatgtctgaa tttagcgtgt cacgtcagac    6000
cgtgaataga gcacttaagg tctgcgggca ttgaacttcc acgaggacgc cgaaagcttc    6060
ccagtaaatg tgccatctcg taggcagaaa acggttcccc cgtagggtct ctctcttggc    6120
ctcctttcta ggtcgggctg attgctcttg aagctctcta gggggctca caccataggc     6180 agataacgtt ccccaccggc tcgcctcgta agcgcacaag gactgctccc aaagatcttc    6240
aaagccactg ccgcgactgc cttcgcgaag ccttgccccg cggaaatttc ctccaccgag    6300
ttcgtgcaca cccctatgcc aagcttcttt caccctaaat tcgagagatt ggattcttac    6360
cgtggaaatt cttcgcaaaa atcgtcccct gatcgccctt gcgacgttgg cgtcggtgcc    6420
gctggttgcg cttggcttga ccgacttgat cagcggccgc tcgatttaaa tc            6472
```

METHOD FOR ZYMOTIC PRODUCTION OF FINE CHEMICALS (META) CONTAINING SULPHUR

RELATED APPLICATIONS

This application is a national stage application (under 35 U.S.C. 371) of PCT/EP2003/009452 filed Aug. 26, 2003, which claims benefit of German application 102 39 073.8 filed Aug. 26, 2002.

The invention relates to a method for the fermentative production of sulfur-containing fine chemicals, in particular L-methionine, by using bacteria which express a nucleotide sequence coding for a homoserine O-acetyltransferase (metA) gene.

PRIOR ART

Sulfur-containing fine chemicals such as, for example, methionine, homocysteine, S-adenosylmethionine, glutathione, cysteine, biotin, thiamine, lipoic acid are produced in cells via natural metabolic processes and are used in many branches of industry, including the food, animal feed, cosmetics and pharmaceutical industries. These substances which are collectively referred to "sulfur-containing fine chemicals" include organic acids, both proteinogenic and nonproteinogenic amino acids, vitamins and cofactors. They are most expediently produced on a large scale by means of cultivating bacteria which have been developed in order to produce and secrete large amounts of the substance desired in each case. Organisms which are particularly suitable for this purpose are coryneform bacteria, Gram-positive nonpathogenic bacteria.

It is known that amino acids are produced by fermentation of strains of coryneform bacteria, in particular *Corynebacterium glutamicum*. Due to the great importance, the production processes are constantly improved. Process improvements can relate to measures regarding technical aspects of the fermentation, such as, for example, stirring and oxygen supply, or to the nutrient media composition such as, for example, sugar concentration during fermentation or to the work-up to give the product, for example by ion exchange chromatography, or to the intrinsic performance properties of the microorganism itself.

A number of mutant strains which produce an assortment of desirable compounds from the group of sulfur-containing fine chemicals have been developed via strain selection. The performance properties of said microorganisms are improved with respect to the production of a particular molecule by applying methods of mutagenesis, selection and mutant selection. However, this is a time-consuming and difficult process. In this way strains are obtained, for example, which are resistant to antimetabolites such as, for example, the methionine analogs α-methylmethionine, ethionine, norleucine, n-acetylnorleucine, S-trifluoromethylhomocysteine, 2-amino-5-heprenoitic acid, selenomethionine, methioninesulfoximine, methoxine, 1-aminocyclopentanecarboxylic acid or which are auxotrophic for metabolites important for regulation and which produce sulfur-containing fine chemicals such as, for example, L-methionine.

Methods of recombinant DNA technology have also been used for some years to improve *Corynebacterium* strains producing L-amino acids by amplifying individual amino-acid biosynthesis genes and investigating the effect on amino acid production.

BRIEF DESCRIPTION OF THE INVENTION

It is an object of the present invention to provide a novel method for the improved fermentative production of sulfur-containing fine chemicals, in particular L-methionine.

We have found that this object is achieved by providing a method for the fermentative production of a sulfur-containing fine chemical, comprising the expression of a heterologous nucleotide sequence coding for a protein with metA activity in a coryneform bacterium.

The invention firstly relates to a method for the fermentative production of at least one sulfur-containing fine chemical, which comprises the following steps:

a) fermentation of a coryneform bacteria culture producing the desired sulfur-containing fine chemical, the coryneform bacteria expressing at least one heterologous nucleotide sequence which codes for a protein with homoserine O-acetyltransferase (meta) activity;

b) concentration of the sulfur-containing fine chemical in the medium or in the bacterial cells, and c) isolation of the sulfur-containing fine chemical, which preferably comprises L-methionine.

The above heterologous meta-encoding nucleotide sequence is preferably less than 100% and preferably more than 70%, homologous to the meta-encoding sequence from *Corynebacterium glutamicum* ATCC 13032. The meta-encoding sequence is derived preferably from any of the following organisms of list I:

| List I | |
|---|---|
| *Corynebacterium diphteriae* | ATCC 14779 |
| *Mycobacterium leprae* | ATCC 43910 |
| *Mycobacterium tuberculosis* CDC1551 | ATCC 25584 |
| *Chlorobium tepidum* | ATCC 49652 |
| *Pseudomonas aeruginosa* | ATCC 17933 |
| *Caulobacter crescentus* | ATCC 19089 |
| *Neisseria gonorrhoeae* | ATCC 53420 |
| *Neisseria meningitidis* | ATCC 53414 |
| *Pseudomonas fluorescens* | ATCC 13525 |
| *Burkholderia cepacia* | ATCC 25416 |
| *Nitrosomonas europaea* | ATCC 19718 |
| *Haemophilus influenzae* | ATCC 51907 |
| *Halobacterium* sp NRC1 | ATCC 33170 |
| *Thermus thermophilus* | ATCC 27634 |
| *Deinococcus radiodurans* | ATCC 13939 |
| *Saccharomyces cerevisiae* | ATCC 10751 |
| *Schizosaccharomyces pombe* | ATCC 24969 |
| *Xylella fastidiosa* | ATCC 35881 |
| *Emericella nidulans* | ATCC 36104 |
| *Mesorhizobium loti* | ATCC 35173 |
| *Acremonium crysogenum* | ATCC 11550 |
| *Pseudomonas putida* | ATCC 47054 |
| *Staphylococcus aureus* | ATCC 35556 |

ATCC: American Type Culture Collection, Rockville, MD, USA

The metA-encoding sequence used according to the invention preferably comprises a coding sequence according to SEQ ID NO:1, 3, 5, 7, 9, 11, 13, 15, 17, 19, 21, 23, 25, 27, 29, 31, 33, 35, 37, 39, 41, 43 and 45 or a nucleotide sequence homologous thereto which codes for a protein with metA activity.

Moreover, the metA-encoding sequence used according to the invention preferably codes for a protein with metA activity, said protein comprising an amino acid sequence according to SEQ ID NO:2, 4, 6, 8, 10, 12, 14, 16, 18, 20, 22, 24, 26, 28, 30, 32, 34, 36, 38, 40, 42, 44 and 46 or an amino acid sequence homologous thereto which represents a protein with metA activity.

The coding metA sequence is preferably a DNA or an RNA which can be replicated in coryneform bacteria or is stably integrated into the chromosome.

According to a preferred embodiment, the method of the invention is carried out by a) using a bacterial strain transformed with a plasmid vector which carries at least one copy of the coding metA sequence under the control of regulatory sequences or
b) using a strain in which the coding metA sequence has been integrated into the bacterial chromosome.

Furthermore, preference is given to overexpressing the coding metA sequence for the fermentation.

It may also be desirable to ferment bacteria in which additionally at least one further gene of the biosynthetic pathway of the desired sulfur-containing fine chemical has been amplified; and/or in which at least one metabolic pathway, which reduces production of the desired sulfur-containing fine chemical has, at least partially, been switched off.

It may also be desirable to ferment bacteria in which additionally the activity of at least one further gene of the biosynthetic pathway of the desired sulfur-containing fine chemical is not undesirably influenced by metabolic metabolites.

Therefore, according to another embodiment of the method of the invention, coryneform bacteria are fermented in which, at the same time, at least one of the genes selected from among a) the gene lysC, which encodes an aspartate kinase,
b) the gene asd, which encodes an aspartate-semialdehyde dehydrogenase,
c) the glyceraldehyde-3-phosphate dehydrogenase-encoding gene gap,
d) the 3-phosphoglycerate kinase-encoding gene pgk,
e) the pyruvate carboxylase-encoding gene pyc,
f) the triose phosphate isomerase-encoding gene tpi,
g) the methionine synthase-encoding gene metH,
h) the cystathionine gamma-synthase-encoding gene metB,
i) the cystathionine gamma-lyase-encoding gene metC,
j) the serine hydroxymethyltransferase-encoding gene glyA,
k) the O-acetylhomoserine sulfhydrylase-encoding gene metY,
l) the methylene tetrahydrofolate reductase-encoding gene metF,
m) the phosphoserine aminotransferase-encoding gene serC,
n) the phosphoserine phosphatase-encoding gene serB,
o) the serine acetyl transferase-encoding gene cysE,
p) the homoserine dehydrogenase-encoding gene hom is overexpressed.

According to another embodiment of the method of the invention, coryneform bacteria are fermented in which, at the same time, at least one of the genes selected from among genes of the abovementioned group a) to p) is mutated in such a way that the activity of the corresponding proteins is influenced by metabolic metabolites to a smaller extent, if at all, compared to nonmutated proteins and that in particular the inventive production of the fine chemical is not adversely affected.

According to another embodiment of the method of the invention, coryneform bacteria are fermented in which, at the same time, at least one of the genes selected from among q) the homoserine kinase-encoding gene thrB,
r) the threonine dehydratase-encoding gene ilvA,
s) the threonine synthase-encoding gene thrC,
t) the meso-diaminopimelate D-dehydrogenase-encoding gene ddh,
u) the phosphoenolpyruvate carboxykinase-encoding gene pck,
v) the glucose-6-phosphate 6-isomerase-encoding gene pgi,
w) the pyruvate oxidase-encoding gene poxB,
x) the dihydrodipicolinate synthase-encoding gene dapA,
y) the dihydrodipicolinate reductase-encoding gene dapB; or
z) the diaminopicolinate decarboxylase-encoding gene lysA is attenuated, in particular by reducing the rate of expression of the corresponding gene.

According to another embodiment of the method of the invention, coryneform bacteria are fermented in which, at the same time, at least one of the genes of the above groups q) to z) is mutated in such a way that the enzymic activity of the corresponding protein is partially or completely reduced.

Preference is given to using, in the method of the invention, microorganisms of the species *Corynebacterium glutamicum*.

The invention further relates to a method for producing an L-methionine-containing animal feed additive from fermentation broths, which comprises the following steps:

a) culturing and fermentation of an L-methionine-producing microorganism in a fermentation medium;
b) removal of water from the L-methionine-containing fermentation broth;
c) removal of from 0 to 100% by weight of the biomass formed during fermentation; and
d) drying of the fermentation broth obtained according to b) and/or c), in order to obtain the animal feed additive in the desired powder or granule form.

The invention likewise relates to the coding metA sequences isolated from the above microorganisms for the first time, to the homoserine O-acetyltransferase encoded thereby and to the functional homologs of these polynucleotides and proteins, respectively.

Figure 1:
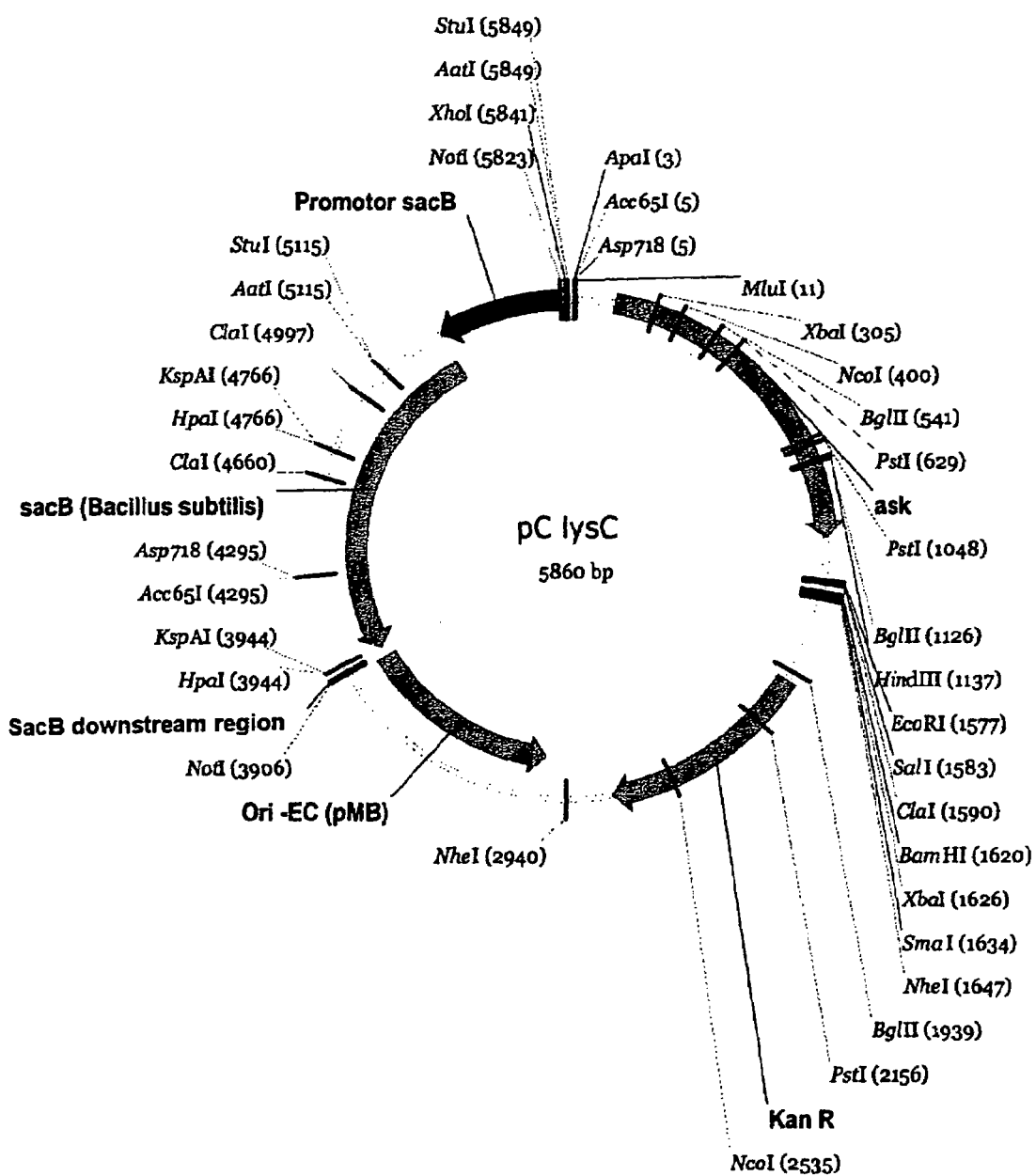
FIG. 1 shows the plasmid map of plasmid pCIS lysC.

DETAILED DESCRIPTION OF THE INVENTION a) General Terms

Proteins with homoserine O-acetyltransferase activity, also referred to as metA (EC 2.3.1.31), are described as being proteins which are capable of converting homoserine and acetyl coenzyme A into O-acetylhomoserine. The skilled worker distinguishes between the activity of homoserine O-acetyltransferase and that of homoserine O-succinyltransferase, but also referred to as metA in the literature. In the latter enzyme, succinyl coenzyme A and not acetyl coenzyme A acts as the substrate for the reaction. The skilled worker can detect the enzymatic activity of homoserine O-acetyltransferase by means of enzyme assays, protocols for which may be: Park S D. Lee J Y. Kim Y. Kim J H. Lee H S. Molecules & Cells. 8(3): 286–94, 1998.

Within the scope of the present invention, the term "sulfur-containing fine chemical" includes any chemical compound which contains at least one covalently bound sulfur atom and is accessible by a fermentation method of the invention. Nonlimiting examples thereof are methionine, homocysteine, S-adenosylmethionine, in particular methionine and S-adenosylmethionine.

Within the scope of the present invention, the terms "L-methionine", "methionine", homocysteine and S-adenosylmethionine also include the corresponding salts such as, for example, methionine hydrochloride or methionine sulfate.

"Polynucleotides" in general refers to polyribonucleotides (RNA) and polydeoxyribonucleotides (DNA) which may be unmodified RNA and DNA respectively, or modified RNA and DNA, respectively.

According to the invention, "polypeptides" means peptides or proteins which contain two or more amino acids linked via peptide bonds.

The term "metabolic metabolite" refers to chemical compounds which occur in the metabolism of organisms as intermediates or else final products and which, apart from their property as chemical building blocks, may also have a modulating effect on enzymes and on their catalytic activity. It is known from the literature that such metabolic metabolites may act on the activity of enzymes in both an inhibiting and a stimulating manner (Biochemistry, Stryer, Lubert, 1995 W. H. Freeman & Company, New York, N.Y.). The possibility of producing in organisms enzymes in which the influence of metabolic metabolites has been modified by measures such as mutation of the genomic DNA by UV radiation, ionizing radiation or mutagenic substances and subsequent selection for particular phenotypes has also been described in the literature (Sahm H., Eggeling L., de Graaf A A., Biological Chemistry 381 (9–10):899–910, 2000; Eikmanns B J., Eggeling L., Sahm H., Antonie van Leeuwenhoek., 64:145–63, 1993–94). These altered properties may also be achieved by specific measurements. The skilled worker knows that it is also possible specifically to modify in enzyme genes particular nucleotides of the DNA coding for the protein in such a way that the protein resulting from the expressed DNA sequence has certain new properties, for example that the modulating effect of metabolic metabolites on the unmodified protein has changed.

The terms "express" and "amplification" or "overexpression" describe in the context of the invention the production of or increase in intracellular activity of one or more enzymes encoded by the corresponding DNA in a microorganism. For this purpose, for example, it is possible to introduce a gene into an organism, to replace an existing gene by another gene, to increase the copy number of the gene or genes, to use a strong promoter or to use a gene which codes for a corresponding enzyme having a high activity, and these measures can be combined, where appropriate.

b) metA Proteins of the Invention

The invention likewise includes "functional equivalents" of the specifically disclosed metA enzymes of organisms in the above list 1.

Within the scope of the present invention, "functional equivalents" or analogs of the specifically disclosed polypeptides are polypeptides different therefrom, which furthermore have the desired biological activity such as, for example, substrate specificity.

According to the invention, "functional equivalents" means in particular mutants which have in at least one of the abovementioned sequence positions an amino acid other than the specifically mentioned amino acid, but which have nevertheless one of the abovementioned biological activities. "Functional equivalents" thus also include the mutants obtainable by one or more amino acid additions, substitutions, deletions and/or inversions, it being possible for said modifications to occur at any position in the sequence as long as they result in a mutant having the property profile of the invention. There is functional equivalence in particular also when the reaction patterns of mutant and unmodified polypeptide match qualitatively, i.e. identical substrates are converted with different rates, for example.

"Functional equivalents" naturally also comprise polypeptides which are obtainable from other organisms, and naturally occurring variants. For example, homologous sequence regions can be found by sequence comparison, and equivalent enzymes can be established following the specific guidelines of the invention.

"Functional equivalents" likewise comprise fragments, preferably individual domains or sequence motifs, of the polypeptides of the invention, which have the desired biological function, for example.

"Functional equivalents" are also fusion proteins which have one of the abovementioned polypeptide sequences or functional equivalents derived therefrom and at least one further heterologous sequence functionally different therefrom in functional N- or C-terminal linkage (i.e. with negligible functional impairment of the functions of the fusion protein parts). Nonlimiting examples of such heterologous sequences are, for example, signal peptides, enzymes, immunoglobulins, surface antigens, receptors or receptor ligands.

According to the invention, "functional equivalents" include homologs of the specifically disclosed proteins. These have at least 20%, or about 30%, 40%, 50%, preferably at least about 60%, 65%, 70%, or 75%, in particular at least 85%, such as, for example, 90%, 95% or 99%, homology to one of the specifically disclosed sequences, calculated by the algorithm of Pearson and Lipman, Proc. Natl. Acad., Sci. (USA) 85(8), 1988, 2444–2448.

Homologs of the proteins or polypeptides of the invention can be generated by mutagenesis, for example by point mutation or truncation of the protein. The term "homolog", as used herein, relates to a variant form of the protein, which acts as agonist or antagonist of the protein activity.

Homologs of the proteins of the invention can be identified by screening combinatorial libraries of mutants such as, for example, truncation mutants. It is possible, for example, to generate a variegated library of protein variants by combinatory mutagenesis at the nucleic acid level, for example by enzymatic ligation of a mixture of synthetic oligonucleotides. There is a multiplicity of methods which can be used for preparing libraries of potential homologs from a degenerate oligonucleotide sequence. Chemical synthesis of a degenerate gene sequence can be carried out in an automatic DNA synthesizer, and the synthetic gene can then be ligated into a suitable expression vector. The use of a degenerate set of genes makes it possible to provide whole sequences which encode the desired set of potential protein sequences in one mixture. Methods for synthesizing degenerate oligonucleotides are known to the skilled worker (for example, Narang, S. A., (1983) Tetrahedron 39:3; Itakura et al., (1984) Annu. Rev. Biochem. 53:323; Itakura et al., (1984) Science 198:1056; Ike et al., (1983) Nucleic Acids Res. 11:477).

In addition, libraries of fragments of the protein codon can be used to generate a variegated population of protein fragments for screening and for subsequent selection of homologs of a protein of the invention. In one embodiment, a library of coding sequence fragments can be generated by treating a double-stranded PCR fragment of a coding sequence with a nuclease under conditions under which nicking occurs only about once per molecule, denaturing the double-stranded DNA, renaturing the DNA to form double-stranded DNA which may comprise sense/antisense pairs of various nicked products, removing single-stranded sections from newly formed duplexes by treatment with S1 nuclease and ligating the resulting fragment library into an expression vector. It is possible by this method to devise an expression library which encodes N-terminal, C-terminal and internal fragments of the protein of the invention, which has different sizes.

Several techniques are known in the prior art for screening gene products from combinatorial libraries which have been produced by point mutations or truncation and for screening DNA libraries for gene products with a selected property. These techniques can be adapted to rapid screening of gene libraries which have been generated by combinatorial mutagenesis of homologs of the invention. The most frequently used techniques for screening large gene libraries undergoing high-throughput analysis comprise the cloning of the gene library into replicable expression vectors, transformation of suitable cells with the resulting vector library and expression of the combinatorial genes under conditions under which detection of the desired activity facilitates isolation of the vector encoding the gene whose product has been detected. Recursive ensemble mutagenesis (REM), a technique which increases the frequency of functional mutants in the libraries, can be used in combination with the screening tests in order to identify homologs (Arkin und Yourvan (1992) PNAS 89:7811–7815; Delgrave et al. (1993) Protein Engineering 6(3):327–331 c) Polynucleotides of the Invention

The invention also relates to nucleic acid sequences (single- and double-stranded DNA and RNA sequences such as, for example cDNA and mRNA) coding for one of the above metA enzymes and the functional equivalents thereof which are obtainable, for example, also by use of artificial nucleotide analogs.

The invention relates both to isolated nucleic acid molecules which code for polypeptides or proteins of the invention or for biologically active sections thereof, and to nucleic acid fragments which can be used, for example, for use as hybridization probes or primers for identifying or amplifying coding nucleic acids of the invention.

Moreover, the nucleic acid molecules of the invention may contain untranslated sequences from the 3' and/or 5' ends of the coding region of the gene.

An "isolated" nucleic acid molecule is separated from other nucleic acid molecules which are present in the natural source of the nucleic acid and may moreover be essentially free of other cellular material or culture medium if it is prepared by recombinant techniques, or free of chemical precursors or other chemicals if it is chemically synthesized.

The invention furthermore comprises the nucleic acid molecules complementary to the specifically described nucleotide sequences or a section thereof.

The nucleotide sequences of the invention make it possible to generate probes and primers which can be used for identifying and/or cloning homologous sequences in other cell types and organisms. Such probes and primers usually complete a nucleotide sequence region which hybridizes under stringent conditions to at least about 12, preferably at least about 25, such as, for example 40, 50 or 75, consecutive nucleotides of a sense strand of a nucleic acid sequence of the invention or of a corresponding antisense strand.

Further nucleic acid sequences of the invention are derived from SEQ ID NO:1, 3, 5, 7, 9, 11, 13, 15, 17, 19, 21, 23, 25, 27, 29, 31, 33, 35, 37, 39, 41, 43 or 45 and differ therefrom through addition, substitution, insertion or deletion of one or more nucleotides, but still code for polypeptides having the desired profile of properties. These may be polynucleotides which are identical to above sequences in at least about 50%, 55%, 60%, 65%, 70%, 80% or 90%, preferably in at least about 95%, 96%, 97%, 98% or 99%, of the sequence positions.

The invention also includes those nucleic acid sequences which comprise "silent" mutations or are modified, by comparison with a specifically mentioned sequence, in accordance with the codon usage of a specific source or host organism, as well as naturally occurring variants such as, for example, splice variants or allelic variants. The invention likewise relates to sequences which are obtainable by conservative nucleotide substitutions (i.e. the relevant amino acid is replaced by an amino acid of the same charge, size, polarity and/or solubility).

The invention also relates to molecules derived from specifically disclosed nucleic acids through sequence polymorphisms. These genetic polymorphisms may exist because of the natural variation between individuals within a population. These natural variations usually result in a variance of from 1 to 5% in the nucleotide sequence of a gene.

The invention furthermore also comprises nucleic acid sequences which hybridize with or are complementary to the abovementioned coding sequences. These polynucleotides can be found on screening of genomic or cDNA libraries, and where appropriate, be amplified therefrom by means of PCR using suitable primers, and then, for example, be isolated with suitable probes. Another possibility is to transform suitable microorganisms with polynucleotides or vectors of the invention, multiply the microorganisms and thus the polynucleotides, and then isolate them. An additional possibility is to synthesize polynucleotides of the invention by chemical routes.

The property of being able to "hybridize" to polynucleotides means the ability of a polynucleotide or oligonucleotide to bind under stringent conditions to an almost complementary sequence, while there are no unspecific bindings between noncomplementary partners under these conditions. For this purpose, the sequences should be 70–100%, preferably 90–100%, complementary. The property of complementary sequences being able to bind specifically to one another is made use of, for example, in the Northern or Southern blot technique or in PCR or RT-PCR in the case of primer binding. Oligonucleotides with a length of 30 base pairs or more are usually employed for this purpose. Stringent conditions means, for example, in the Northern blot technique the use of a washing solution at 50–70° C., preferably 60–65° C., for example 0.1×SSC buffer with 0.1% SDS (20×SSC; 3M NaCl, 0.3M Na citrate, pH 7.0) for eluting nonspecifically hybridized cDNA probes or oligonucleotides. In this case, as mentioned above, only nucleic acids with a high degree of complementarity remain bound to one another. The setting up of stringent conditions is known to the skilled worker and is described, for example, in Ausubel et al., Current Protocols in Molecular Biology, John Wiley & Sons, N.Y. (1989), 6.3.1–6.3.6.

d) Isolation of the Coding metA Gene

The metA genes coding for the enzyme homoserine O-acetyltransferase can be isolated from the organisms of the above list I in a manner known per se.

In order to isolate the metA genes or else other genes of the organisms of the above list 1, first a gene library of this organism is generated in *Escherichia coli* (*E. coli*). The generation of gene libraries is described in detail in generally known textbooks and manuals. Examples which may be mentioned are the textbook by Winnacker: Gene und Klone, Eine Einführung in die Gentechnologie (Verlag Chemie, Weinheim, Germany, 1990), and the manual by Sambrook et al.: Molecular Cloning, A Laboratory Manual (Cold Spring Harbor Laboratory Press, 1989). A very well-known gene library is that of *E. coli* K-12 strain W3110, which was generated in λ vectors by Kohara et al. (Cell 50, 495–508 (198)).

In order to produce a gene library from organisms of list I in *E. coli*, cosmids such as the cosmid vector SuperCos I (Wahl et al., 1987, Proceedings of the National Academy of Sciences USA, 84: 2160–2164), or else plasmids such as pBR322 (BoliVal; Life Sciences, 25, 807–818 (1979)) or pUC9 (Vieira et al., 1982, Gene, 19: 259–268) can be used. Suitable hosts are in particular those *E. coli* strains which are restriction and recombination defective. An example of this is the strain DH5αmcr which has been described by Grant et al. (Proceedings of the National Academy of Sciences USA, 87 (1990) 46454649). The long DNA fragments cloned with the aid of cosmids may then in turn be subcloned into common vectors suitable for sequencing and subsequently be sequenced, as described, for example, in Sanger et al. (proceedings of the National Academy of Sciences of the United States of America, 74: 5463–5467, 1977).

The DNA sequences obtained can then be studied using known algorithms or sequence analysis programs such as, for example, those by Staden (Nucleic Acids Research 14,217–232(1986)), by Marck (Nucleic Acids Research 16,1829–1836 (1988)) or the GCG program by Butler (Methods of Biochemical Analysis 39, 74–97 (1998)).

The meta-encoding DNA sequences from organisms according to the above list I were found. In particular, DNA sequences according to SEQ ID NO:1, 3, 5, 7, 9, 11, 13, 15, 17, 19, 21, 23, 25, 27, 29, 31, 33, 35, 37, 39, 41, 43 and 45, were found. Furthermore, the amino acid sequences of the corresponding proteins were derived from said DNA sequences present, using the above-described methods. SEQ ID NO:2, 4, 6, 8, 10, 12, 14, 16, 18, 20, 22, 24, 26, 28, 30, 32, 34, 36, 38, 40, 42, 44 and 46 depict the resulting amino acid sequences of the metA gene products.

Coding DNA sequences which result from the sequences according to SEQ ID NO:1, 3, 5, 7, 9, 11, 13, 15, 17, 19, 21, 23, 25, 27, 29, 31, 33, 35, 37, 39, 41, 43 and 45 due to the degeneracy of the genetic code are likewise subject of the invention. In the same way, the invention relates to DNA sequences which hybridize with said sequences or parts of sequences derived therefrom.

Instructions for identifying DNA sequences by means of hybridization can be found by the skilled worker, inter alia, in the manual "The DIG System Users Guide fur Filter Hybridization" from Boehringer Mannheim GmbH (Mannheim, Germany, 1993) and in Liebl et al. (International Journal of Systematic Bacteriology (1991) 41: 255–260). Instructions for amplifying DNA sequences with the aid of the polymerase chain reaction (PCR) can be found by the skilled worker, inter alia, in the manual by Gait: Oligonucleotide synthesis: A Practical Approach (IRL Press, Oxford, UK, 1984) and in Newton and Graham: PCR (Spektrum Akademischer Verlag, Heidelberg, Germany, 1994).

It is furthermore known that changes at the N- and/or C-terminus of a protein do not substantially impair its function or may even stabilize said function. Information on this can be found by the skilled worker, inter alia, in Ben-Bassat et al. (Journal of Bacteriology 169: 751–757 (1987)), in O'Regan et al. (Gene 77: 237–251 (1989), in Sahin-Toth et al. (Protein Sciences 3: 240–247 (1994)), in Hochuli et al. (Biotechnology 6:1321–1325 (1988)) and in known textbooks of genetics and molecular biology.

Amino acid sequences which result accordingly from SEQ ID NO:2, 4, 6, 8, 10, 12, 14, 16, 18, 20, 22, 24, 26, 28, 30, 32, 34, 36, 38, 40, 42, 44 and 46 are likewise part of the invention.

e) Host Cells Used According to the Invention

The invention further relates to microorganisms serving as host cells, in particular coryneform bacteria, which contain a vector, in particular a shuttle vector or plasmid vector, carrying at least one metA gene as defined by the invention or in which a metA gene of the invention is expressed or amplified.

These microorganisms can produce sulfur-containing fine chemicals, in particular L-methionine, from glucose, sucrose, lactose, fructose, maltose, molasses, starch, cellulose or from glycerol and ethanol. Said microorganisms are preferably coryneform bacteria, in particular of the genus *Corynebacterium*. Of the genus *Corynebacterium*, mention must be made in particular of the species *Corynebacterium glutamicum* which is known in the art for its ability to produce L-amino acids.

Examples of suitable strains of coryneform bacteria, which may be mentioned, are those of the genus *Corynebacterium*, in particular of the species *Corynebacterium glutamicum* (*C. glutamicum*), such as
*Corynebacterium glutamicum* ATCC 13032,
*Corynebacterium acetoglutamicum* ATCC 15806,
*Corynebacterium acetoacidophilum* ATCC 13870,
*Corynebacterium thermoaminogenes* FERM BP-1539,
*Corynebacterium melassecola* ATCC 17965
or
of the genus *Brevibacterium*, such as
*Brevibacterium flavum* ATCC 14067
*Brevibacterium lactofermentum* ATCC 13869 and
*Brevibacterium divaricatum* ATCC 14020;

Or strains derived therefrom such as
*Corynebacterium glutamicum* KFCC10065
*Corynebacterium glutamicum* ATCC21608
which likewise produce the desired fine chemical or the precursor(s) thereof.

The abbreviation KFCC means the Korean Federation of Culture Collection, the abbreviation ATCC means the American Type Strain Culture Collection, the abbreviation FERM BP refers to the Collection of the National Institute of Bioscience and Human Technology, Agency of Industrial Science and Technology, Japan.

f) Carrying Out the Fermentation of the Invention

According to the invention, it was found that coryneform bacteria, after overexpression of a meta gene from organisms of the list I, produce sulfur-containing fine chemicals, in particular L-methionine, in an advantageous manner.

To achieve overexpression, the skilled worker can take different measures individually or in combination. Thus it is possible to increase the copy number of the appropriate genes or to mutate the promoter and regulatory region or the ribosomal binding site which is located upstream of the structural gene. Expression cassettes which are incorporated upstream of the structural gene act in the same way. Inducible promoters make it additionally possible to increase expression during the course of the fermentative L-methionine production. Expression is likewise improved by measures which extend the life span of the mRNA. Furthermore, the enzymic activity is likewise enhanced by preventing degradation of the enzyme protein. The genes or gene constructs may be either present in plasmids with varying copy number or integrated and amplified in the chromosome. A further possible alternative is to achieve overexpression of the relevant genes by changing the media composition and management of the culture.

Instructions for this can be found by the skilled worker, inter alia, in Martin et al. (Biontechnology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102,93–98 (1991)), in the European patent 0472869, in U.S. Pat. No. 4,601,893, in Schwarzer and Pühler (Biotechnology 9,84–87 (1991)), in Remscheid et al. (Applied and Environmental Microbiology60,126–132 (1994), in LaBarre et al. (Journal of Bacteriology 175, 1001–1007 (1993)), in the patent application WO 96/15246, in Malumbres et al. (Gene 134,15–24 (1993)), in the Japanese published specification JP-A-10-229891, in Jensen und Hammer (Biotechnology and Bioengineering 58, 191–195 (1998)), in Makrides (Microbiological Reviews 60: 512–538 (1996) and in known textbooks of genetics and molecular biology.

The invention therefore also relates to expression constructs comprising a nucleic acid sequence coding for a polypeptide of the invention under the genetic control of regulatory nucleic acid sequences; and to vectors comprising at least one of said expression constructs. Such constructs of the invention preferably include a promoter 5' upstream of the particular coding sequence and a terminator sequence 3' downstream and also, where appropriate, further regulatory elements, in each case operatively linked to the coding sequence. An "operative linkage" means the sequential arrangement of promoter, coding sequence, terminator and, where appropriate, further regulatory elements such that each of the regulatory elements can properly carry out its function in the expression of the coding sequence. Examples of operatively linkable sequences are activating sequences and enhancers and the like. Further regulatory elements include selectable markers, amplification signals, origins of replication and the like. Suitable regulatory sequences are described, for example in Goeddel, Gene Expression Technology: Methods in Enzymology 185, Academic Press, San Diego, Calif. (1990).

In addition to the artificial regulatory sequences, the natural regulatory sequence may still be present upstream of the actual structural gene. Genetic modification can, where appropriate, switch off this natural regulation and increase or decrease expression of the genes. However, the gene construct may also have a simpler design, i.e. no additional regulatory signals are inserted upstream of the structural gene and the natural promoter with its regulation is not removed. Instead, the natural regulatory sequence is mutated such that regulation no longer takes place and gene expression is increased or reduced. The gene construct may contain one or more copies of the nucleic acid sequences.

Examples of useful promoters are: ddh, amy, lysC, dapA, lysA from *Corynebacterium glutamicum* promoters, but also Gram-positive promoters SPO2, as are described in *Bacillus Subtilis* and Its Closest Relatives, Sonenshein, Abraham L., Hoch, James A., Losick, Richard; ASM Press, District of Columbia, Washington and Patek M. Eikmanns B J., Patek J., Sahm H., Microbiology. 142 1297–309, 1996 or else the cos, tac, trp, tet, trp-tet, lpp, lac, lpp-lac, laclq, T7, T5, T3, gal, trc, ara, SP6, λ-PR and λ-PL promoters which are advantageously applied in Gram-negative bacteria. Preference is also give to using inducible promoters such as, for example light- and, in particular, temperature-inducible promoters such as the $P_rP_l$ promoter. It is in principle possible to use all natural promoters with their regulatory sequences. In addition, it is also possible to use advantageously synthetic promoters.

The regulatory sequences mentioned are intended to make specific expression of the nucleic acid sequences possible. Depending on the host organism, this may mean, for example, that the gene is expressed or overexpressed only after induction, or that it is immediately expressed and/or overexpressed.

In this connection, the regulatory sequences and factors may preferably have a beneficial effect on, and thus increase or decrease, expression. Thus, it is possible and advantageous to enhance the regulatory elements at the transcriptional level by using strong transcription signals such as promoters and/or enhancers. However, it is also possible besides this to enhance translation by, for example, improving the stability of the mRNA.

An expression cassette is prepared by fusing a suitable promoter, a suitable Shine-Dalgarno sequence, to a metA nucleotide sequence and a suitable termination signal. For this purpose, common recombination and cloning techniques are used, such as those described, for example, in Current Protocols in Molecular Biology, 1993, John Wiley & Sons, Incorporated, New York, N.Y., PCR Methods, Gelfand, David H., Innis, Michael A., Sninsky, John J., 1999, Academic Press, Incorporated, California, San Diego, PCR Cloning Protocols, Methods in Molecular Biology Ser., Vol. 192, 2nd ed., Humana Press, New Jersey, Totowa. T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman und L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The recombinant nucleic acid construct or gene construct is expressed in a suitable host organism by inserting it advantageously into a host-specific vector which makes optimal expression of the genes in the host possible. Vectors are well known to the skilled worker and can be found, for example, in "Cloning Vectors" (Pouwels P. H. et al., Hrsg, Elsevier, Amsterdam-New York-Oxford, 1985). The term "vectors" means, apart from plasmids, also all other vectors known to the skilled worker, such as, for example, phages, transposons, IS elements, plasmids, cosmids and linear or circular DNA. These vectors can replicate autonomously in the host organism or are replicated chromosomally.

MetA genes of the invention were amplified by overexpressing them by way of example with the aid of episomal plasmids. Suitable plasmids are those which are replicated in coryneform bacteria.

Numerous known plasmid vectors such as, for example, pZ1 (Menkel et al., Applied and Environmental Microbiology (1989) 64: 549–554), pEKEx1 (Eikmanns et al., Gene 102: 93–98 (1991)) or pHS2–1 (Sonnen et al., Gene 107: 69–74 (1991)) are based on the cryptic plasmids pHM1519, pBL1 or pGA1. Other plasmid vectors such as, for example, pCLiK5MCS, or those based on pCG4 (U.S. Pat. No. 4,489,160) or pNG2 (Serwold-Davis et al., FEMS Microbiology Letters 66, 119–124 (1990)) or pAG1 (U.S. Pat. No. 5,158,891) may be used in the same way.

Suitable plasmid vectors are furthermore also those with the aid of which it is possible to apply the method of gene amplification by integration into the chromosome, as has been described, for example, by Remscheid et al. (Applied and Environmental Microbiology 60,126–132 (1994)) for the duplication and amplification of the hom-thrB operon. In this method, the complete gene is cloned into a plasmid vector which can replicate in a host (typically E. coli) but not in C. glutamicum. Suitable vectors are, for example, pSUP301 (Simon et al., Bio/Technology 1, 784–791 (1983)), pK18mob or pK19mob (Schäfer et al., Gene 145, 69–73 (1994)), Bernard et al., Journal of Molecular Biology, 234: 534–541 (1993)), pEM1 (Schrumpf et al., 1991, Journal of Bacteriology 173:4510–4516) or pBGS8 (Spratt et al., 1986, Gene 41: 337–342). The plasmid vector containing the gene to be amplified is then transferred into the desired C. glutamicum strain via transformation. Methods for transformation are described, for example, in Thierbach et al. (Applied Microbiology and Biotechnology 29, 356–362 (1988)), Dunican and Shivnan (Biotechnology 7, 1067–1070 (1989)) and Tauch et al. (FEMS Microbiological Letters 123, 343–347 (1994)).

The activity of enzymes can be influenced by mutations in the corresponding genes in such a way that the rate of the enzymic reaction is partly or completely reduced. Examples of such mutations are known to the skilled worker (Motoyama H., Yano H., Terasaki Y., Anazawa H., Applied & Environmental Microbiology. 67:3064–70, 2001, Eikmanns B J., Eggeling L., Sahm H., Antonie van Leeuwenhoek. 64:145–63, 1993–94.)

Additionally, it may be advantageous for the production of sulfur-containing fine chemicals, in particular L-methionine, to amplify, in addition to expression and amplification of a metA gene of the invention, one or more enzymes of the respective biosynthetic pathway, the cysteine pathway, of aspartate-semialdehyde synthesis, of glycolysis, of anaplerosis, of the pentose phosphate metabolism, the citrate acid cycle or the amino acid export.

Thus, one or more of the following genes can be amplified to produce sulfur-containing fine chemicals, in particular L-methionine:

the gene lysC, which encodes an aspartate kinase (EP 1 108 790 A2; DNA-SEQ NO. 281), the gene asd, which encodes an aspartate-semialdehyde dehydrogenase (EP 1 108 790 A2; DNA-SEQ NO. 282), the glyceraldehyde-3-phosphate dehydrogenase-encoding gene gap (Eikmanns (1992), Journal of Bacteriology 174: 6076–6086), the 3-phosphoglycerate kinase-encoding gene pgk (Eikmanns (1992), Journal of Bacteriology 174: 6076–6086), the pyruvate carboxylase-encoding gene pyc (Eikmanns (1992), Journal of Bacteriology 174: 6076–6086), the triose phosphate isomerase-encoding gene tpi (Eikmanns (1992), Journal of Bacteriology 174: 6076–6086), the methionine synthase-encoding gene metH (EP 1 108 790 A2), the cystathionine gamma-synthase-encoding gene metB (EP 1 108 790 A2; DNA-SEQ NO. 3491), the cystathionine gamma-lyase-encoding gene metC (EP 1 108 790 A2; DNA-SEQ NO. 3061), the serine hydroxymethyltransferase-encoding gene glyA (EP 1 108 790 A2; DNA-SEQ NO. 1110), the O-acetylhomoserine sulfhydrylase-encoding gene metY (EP 1 108 790 A2; DNA-SEQ NO. 726), the methylene tetrahydrofolate reductase-encoding gene metF (EP 1 108 790 A2; DNA-SEQ NO. 2379), the phosphoserine aminotransferase-encoding gene serC (EP 1 108 790 A2; DNA-SEQ NO. 928), a phosphoserine phosphatase-encoding gene serB (EP 1 108 790 A2; DNA-SEQ NO. 334, DNA-SEQ NO. 467, DNA-SEQ NO. 2767), the serine acetyltransferase-encoding gene cysE (EP 1 108 790 A2; DNA-SEQ NO. 2818), the gene hom, which encodes a homoserine dehydrogenase (EP 1 108 790 A2; DNA-SEQ NO. 1306)

Thus, it may be advantageous for the production of sulfur-containing fine chemicals, in particular L-methionine, in coryneform bacteria to mutate, at the same time, at least one of the genes below, so that the activity of the corresponding proteins, compared to that of unmutated proteins, is influenced by a metabolic metabolite to a lesser extent or not at all:

the gene lysC, which encodes an aspartate kinase (EP 1 108 790 A2; DNA-SEQ NO. 281), the pyruvate carboxylase-encoding gene pyc (Eikmanns (1992), Journal of Bacteriology 174: 6076–6086), the methionine-synthase-encoding gene metH (EP 1 108 790 A2), the cystathionine gamma-synthase-encoding gene metB (EP 1 108 790 A2; DNA-SEQ NO. 3491), the cystathionine gamma-lyase-encoding gene metC (EP 1 108 790 A2; DNA-SEQ NO. 3061), the serine hydroxymethyltransferase-encoding gene glyA (EP 1 108 790 A2; DNA-SEQ NO. 1110), the O-acetyl-homoserine-sulfhydrylase-encoding gene metY (EP 1 108 790 A2; DNA-SEQ NO. 726), the methylene tetrahydrofolate reductase-encoding gene metF (EP 1 108 790 A2; DNA-SEQ NO. 2379), the phosphoserine aminotransferase-encoding gene serC (EP 1 108 790 A2; DNA-SEQ NO. 928), a phosphoserine phosphatase-encoding gene serB (EP 1 108 790 A2; DNA-SEQ NO. 334, DNA-SEQ NO. 467, DNA-SEQ NO. 2767), the serine acetyl transferase-encoding gene cysE (EP 1 108 790 A2; DNA-SEQ NO. 2818), the gene hom, which encodes a homoserine dehydrogenase (EP 1 108 790 A2; DNA-SEQ NO. 1306)

It may be furthermore advantageous for the production of sulfur-containing fine chemicals, in particular L-methionine, in addition to expression and amplification of one of the metA genes of the invention, to attenuate one or more of the following genes, in particular to reduce expression thereof, or to switch them off:

the homoserine kinase-encoding gene thrB (EP 1 108 790 A2; DNA-SEQ NO. 3453), the threonine dehydratase-encoding gene ilvA (EP 1 108 790 A2; DNA-SEQ NO. 2328), the threonine synthase-encoding gene thrC (EP 1 108 790 A2; DNA-SEQ NO. 3486), the meso-diaminopimelate D-dehydrogenase-encoding gene ddh (EP 1 108 790 A2; DNA-SEQ NO. 3494), the phosphoenolpyruvate carboxykinase-encoding gene pck (EP 1 108 790 A2; DNA-SEQ NO. 3157), the glucose-6-phosphate 6-isomerase-encoding gene pgi (EP 1 108 790 A2; DNA-SEQ NO. 950), the pyruvate oxidase-encoding gene poxB (EP 1 108 790 A2; DNA-SEQ NO. 2873), the dihydrodipicolinate synthase-encoding gene dapA (EP 1 108 790 A2; DNA-SEQ NO. 3476), the dihydrodipicolinate reductase-encoding gene dapB (EP 1 108 790 A2; DNA-SEQ NO. 3477)

the diaminopicolinate decarboxylase-encoding gene lysA (EP 1 108 790 A2; DNA-SEQ NO. 3451)

It may be furthermore advantageous for the production of sulfur-containing fine chemicals, in particular L-methionine, in addition to expression and amplification of one of the metA genes of the invention in coryneform bacteria, to mutate, at the same time, at least one of the following genes in such a way that the enzymic activity of the corresponding protein is partly or completely reduced:

the homoserine kinase-encoding gene thrB (EP 1 108 790 A2; DNA-SEQ NO. 3453), the threonine dehydratase-encoding gene ilvA (EP 1 108 790 A2; DNA-SEQ NO. 2328), the threonine synthase-encoding gene thrC (EP 1 108 790 A2; DNA-SEQ NO. 3486), the meso-diaminopimelate D-dehydrogenase-encoding gene ddh (EP 1 108 790 A2; DNA-SEQ NO. 3494), the phosphoenolpyruvate carboxykinase-encoding gene pck (EP 1 108 790 A2; DNA-SEQ NO. 3157), the glucose-6-phosphate 6-isomerase-encoding gene pgi (EP 1 108 790 A2; DNA-SEQ NO. 950), the pyruvate oxidase-encoding gene poxB (EP 1 108 790 A2; DNA-SEQ NO. 2873), the dihydrodipicolinate synthase-encoding gene dapA (EP 1 108 790 A2; DNA-SEQ NO. 3476), the dihydrodipicolinate reductase-encoding gene dapB (EP 1 108 790 A2; DNA-SEQ NO. 3477)

the diaminopicolinate decarboxylase-encoding gene lysA (EP 1 108 790 A2; DNA-SEQ NO. 3451)

It may be furthermore advantageous for the production of sulfur-containing fine chemicals, in particular L-methionine, apart from expression and amplification of a metA gene of the invention, to eliminate unwanted secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention may be cultured continuously or batchwise or in a fed batch or repeated fed batch process to produce sulfur-containing fine chemicals, in particular L-methionine. An overview of known cultivation methods can be found in the textbook by Chmiel (Bioprozeβtechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must satisfy the demands of the particular strains in a suitable manner. The textbook "Manual of Methods fur General Bacteriology" by the American Society for Bacteriology (Washington D.C., USA, 1981) contains descriptions of culture media for various microorganisms.

Said media which can be used according to the invention usually comprise one or more carbon sources, nitrogen sources, inorganic salts, vitamins and/or trace elements.

Preferred carbon sources are sugars such as mono-, di- or polysaccharides. Examples of very good carbon sources are glucose, fructose, mannose, galactose, ribose, sorbose, ribulose, lactose, maltose, sucrose, raffinose, starch and cellulose. Sugars may also be added to the media via complex compounds such as molasses or other byproducts of sugar refining. It may also be advantageous to add mixtures of different carbon sources. Other possible carbon sources are oils and fats such as, for example, soybean oil, sunflower oil, peanut oil and coconut fat, fatty acids such as, for example, palmitic acid, stearic acid and linoleic acid, alcohols such as, for example, glycerol, methanol and ethanol and organic acids such as, for example acetic acid and lactic acid.

Nitrogen sources are usually organic or inorganic hydrogen compounds or materials containing said compounds. Examples of nitrogen sources include ammonia gas or ammonium salts such as ammonium sulfate, ammonium chloride, ammonium phosphate, ammonium carbonate and ammonium nitrate, nitrates, urea, amino acids and complex nitrogen sources such as cornsteep liquor, soybean flour, soybean protein, yeast extract, meat extract and others. The nitrogen sources may be used singly or as mixture.

Inorganic salt compounds which may be included in the media comprise the chloride, phosphorus or sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents include dihydroxyphenols such as catechol or protocatechuate and organic acids such as citric acid.

The fermentation media used according to the invention usually also contain other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media heavily depends on the particular experiment and is decided upon individually for each specific case. Information on the optimization of media can be found in the textbook "Applied Microbiol. Physiology, A Practical Approach" (Editors. P. M. Rhodes, P. F. Stanbury, IRL Press (1997) pp. 53–73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by sterile filtration. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, air into the culture. The temperature of the culture is normally 20° C. to 45° C. The culture is continued until formation of the desired product is at a maximum. This aim is normally achieved within 10 to 160 hours.

The fermentation broths obtained in this way, in particular those containing L-methionine, usually contain a dry biomass of from 7.5 to 25% by weight.

An additional advantage is to carry out the fermentation under sugar limitation, at least at the end, but in particular over at least 30% of the fermentation period. This means that during this time the concentration of utilizable sugar in the fermentation medium is maintained at or reduced to >0 to 3 g/l.

The fermentation broth is then processed further. The biomass may, according to requirement, be removed completely or partially from the fermentation broth by separation methods such as, for example, centrifugation, filtration, decanting or a combination of these methods or be left completely in said broth.

Subsequently, the fermentation broth may be thickened or concentrated using known methods such as, for example, with the aid of a rotary evaporator, thin film evaporator, falling film evaporator, by reverse osmosis, or by nanofiltration. This concentrated fermentation broth can then be worked up by freeze drying, spray drying, spray granulation or by other methods.

However, it is also possible to further purify the sulfur-containing fine chemicals, in particular L-methionine. To this end, the product-containing broth, after removing the biomass, is subjected to a chromatography using a suitable resin, the desired product or the contaminations being retained completely or partially on the chromatographic resin. These chromatographic steps can be repeated, if necessary, using the same or different chromatographic resin. The skilled worker is familiar with the selection of suitable chromatographic resins and their most effective application. The purified product can be concentrated by filtration or ultrafiltration and stored at a temperature at which the stability of the product is greatest.

The identity and purity of the isolated compound(s) can be determined by techniques of the art. These include high performance liquid chromatography (HPLC), spectroscopic methods, staining methods, thin-layer chromatography, NIRS, enzyme assay or microbiological assays. These analytic methods are summarized in: Patek et al. (1994) Appl. Environ. Microbiol. 60:133–140; Malakhova et al. (1996) Biotekhnologiya 11 27–32; and Schmidt et al. (1998) Bioprocess Engineer. 19:67–70. Ulmann's Encyclopedia of Industrial Chemistry (1996) Bd. A27, VCH: Weinheim, pp. 89–90, pp. 521–540, pp. 540–547, pp. 559–566,575–581 and pp. 581–587; Michal, G., (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Volume 17.

Figure 2:
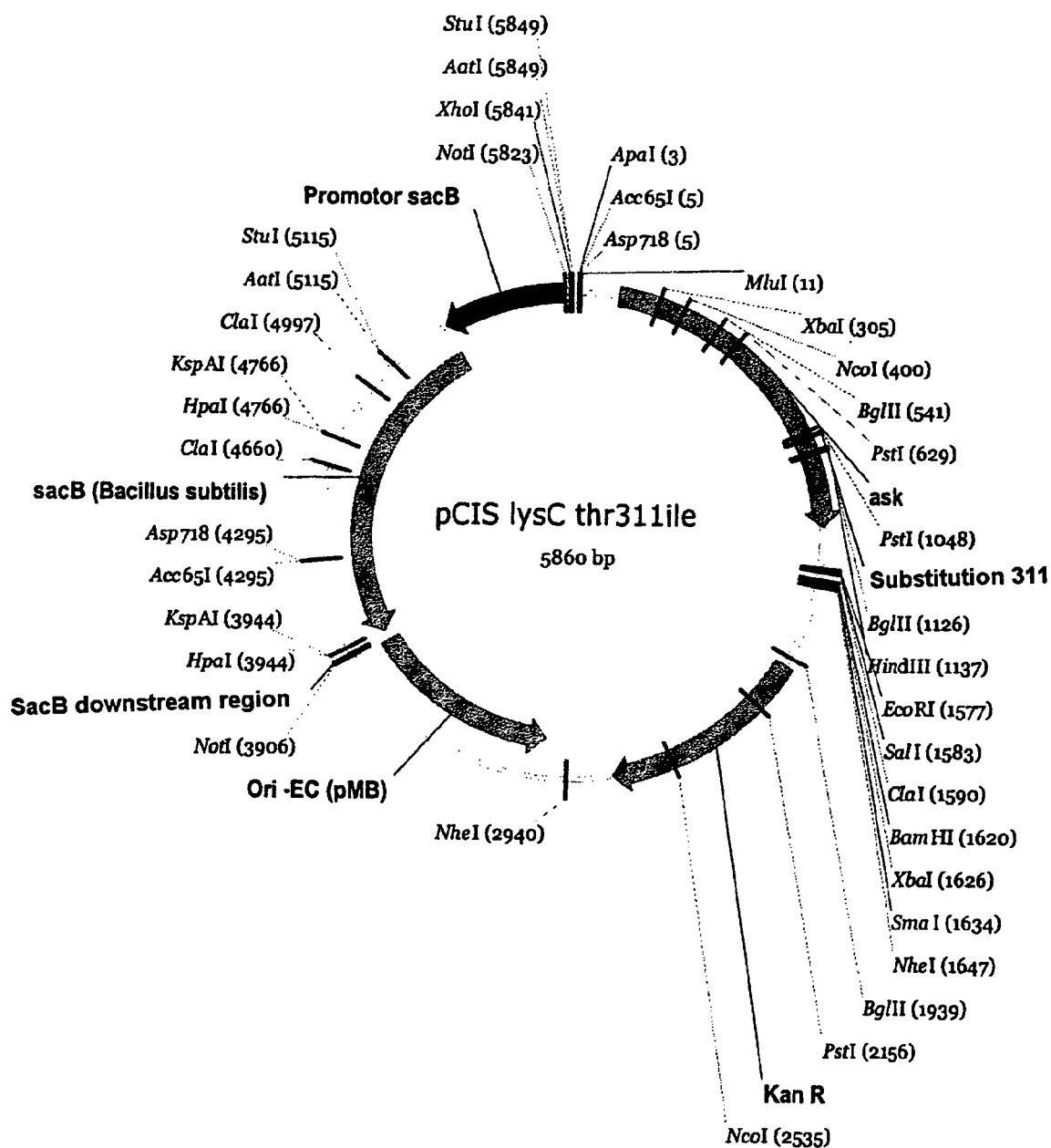
FIG. 2 shows the plasmid map of plasmid pCIS lysC thr311 ile.
Figure 3:
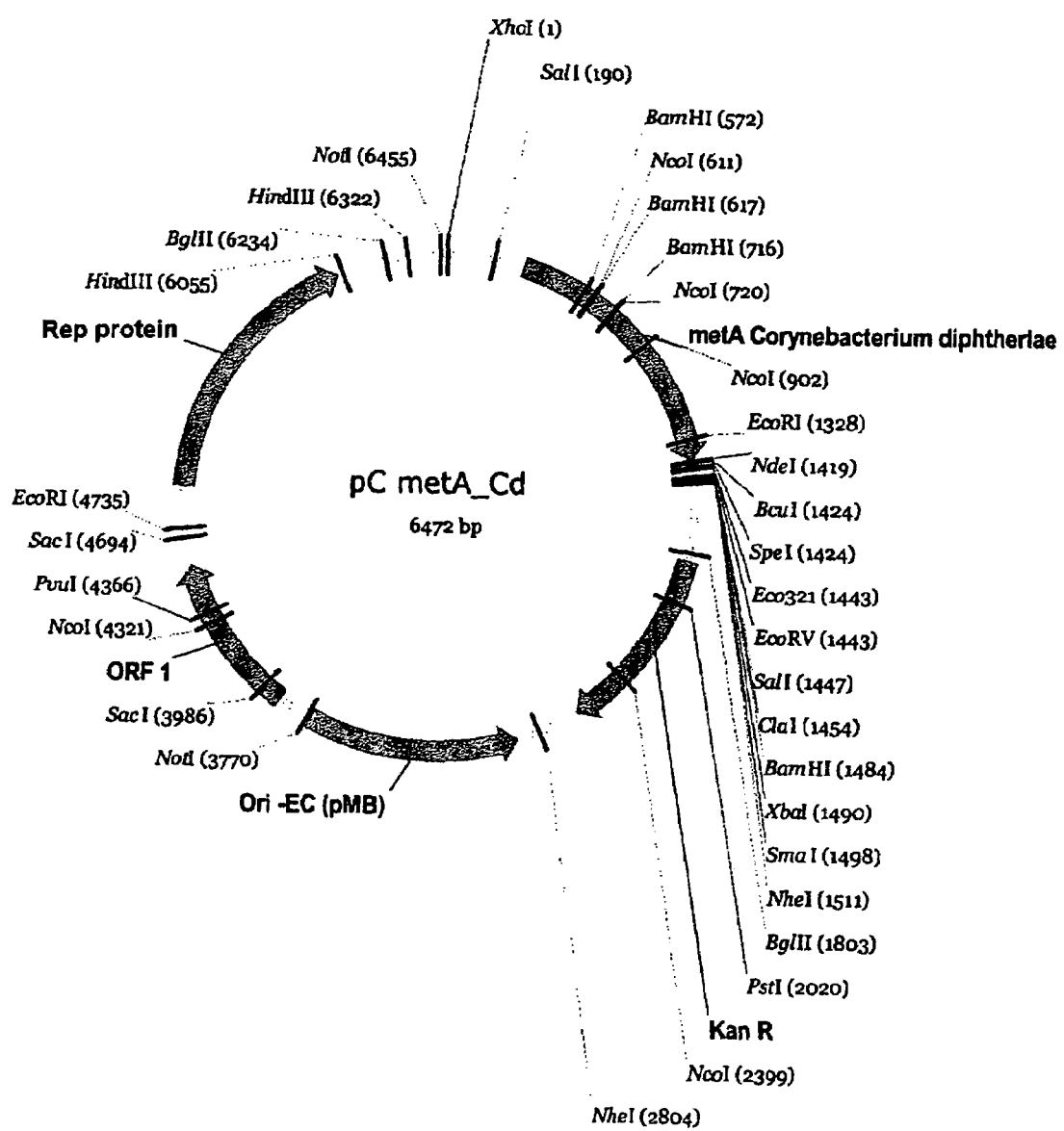
FIG. 3 shows the plasmid map of plasmid pC metA_Cd (Corymebacterium diphteriae).

The following nonlimiting examples and attached figures describe the invention in more detail:

FIG. 1 shows the plasmid map for plasmid pClysC;

FIG. 2 shows the plasmid map for plasmid pClSlysCthr311ile;

FIG. 3 shows the plasmid map for plasmid pC_metA_Cd.

Restriction cleavage sites with their respective positions in brackets are shown in the plasmid maps. Essential sequence segments are printed in bold. KanR means kanamycin resistance gene; ask means aspartate kinase gene.

EXAMPLE 1

Construction of pCLiK5MCS

First, ampicillin resistance and origin of replication of the vector pBR322 were amplified using the oligonucleotides p1.3 (SEQ ID NO:47) and p2.3 (SEQ ID NO:48) with the aid of the polymerase chain reaction (PCR).

```
p1.3 (SEQ ID NO: 47)
5'-CCCGGGATCCGCTAGCGGCGCGCCGGCCGGCCCGGTGTGAAATACCGCACAG-3' p2.3 (SEQ ID NO: 48)
5'-TCTAGACTCGAGCGGCCGCGGCCGGCCTTTAAATTGAAGACGAAAGGGCCTCG-3'
```

In addition to sequences complementary to pBR322, the oligonucleotide p1.3 (SEQ ID NO:47) contains in 5'-3' direction the cleavage sites for the restriction nucleases SmaI, BamHI, NheI and AscI and the oligonucleotide p2.3 (SEQ ID NO:48) contains in 5'-3' direction the cleavage sites for the restriction endonucleases XbaI, XhoI, NotI and DraI. The PCR reaction was carried out according to a standard method such as that by Innis et al. (PCR Protocols. A Guide to Methods and Applications, Academic Press (1990)) using PfuTurbo polymerase (Stratagene, La Jolla, USA). The DNA fragment obtained of approximately 2.1 kb in size was purified using the GFX™PCR, DNA and gel band purification kit (Amersham Pharmacia, Freiburg) according to the manufacturer's instructions. The blunt ends of the DNA fragment were ligated to one another using the rapid DNA ligation kit (Roche Diagnostics, Mannheim) according to the manufacturer's instructions and the ligation mixture was transformed into competent *E. coli* XL-1 Blue (Stratagene, La Jolla, USA) according to standard methods, as described in Sambrook et al. (Molecular Cloning. A Laboratory Manual, Cold Spring Harbor, (1989)). Plasmid-carrying cells were selected for by plating out onto ampicillin (50 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK1.

Starting from plasmid pWLT1 (Liebl et al., 1992) as template for a PCR reaction, a kanamycin resistance cassette was amplified using the oligonucleotides neo1 (SEQ ID NO:49) and neo2 (SEQ ID NO:50).

```
neo1 (SEQ ID NO: 49):
5'-GAGATCTAGACCCGGGGATCCGCTAGCGGGCTGCTAAAGGAAGCGGA-3'
```

```
-continued
neo2 (SEQ ID NO: 50):
5'-GAGAGGCGCGCCGCTAGCGTGGGCGAAGAACTCCAGCA-3'
```

Apart from the sequences complementary to pWLT1, the oligonucleotide neo1 contains in 5'-3' direction the cleavage sites for the restriction endonucleases XbaI, SmaI, BamHI, NheI and the oligonucleotide neo2 (SEQ ID NO:50) contains in 5'-3' direction the cleavage sites for the restriction endonucleases AscI and NheI. The PCR reaction was carried out using PfuTurbo polymerase (Stratagene, La Jolla, USA) according to a standard method such as that of Innis et al. (PCR Protocols. A Guide to Methods and Applications, Academic Press (1990)). The DNA fragment obtained was approximately 1.3 kb in size was purified using the GFX™PCR, DNA and gel band purification kit (Amersham Pharmacia, Freiburg) according to the manufacturer's instructions. The DNA fragment was cleaved with restriction endonucleases XbaI and AscI (New England Biolabs, Beverly, USA) and, following that, again purified using the GFX™PCR, DNA and gel band purification kit (Amersham Pharmacia, Freiburg) according to the manufacturer's instructions. The vector pCLiK1 was likewise cleaved with the restriction endonucleases XbaI and AscI and dephosphorylated using alkaline phosphatase (Roche Diagnostics, Mannheim) according to the manufacturer's instructions. After electrophoresis in a 0.8% strength agarose gel, the linearized vector (approx. 2.1 kb) was isolated using the GFX™PCR, DNA and gel band purification kit (Amersham Pharmacia, Freiburg) according to the manufacturer's instructions. This vector fragment was ligated with the cleaved PCR fragment with the aid of the rapid DNA ligation kit (Roche Diagnostics, Mannheim) according to the manufacturer's instructions and the ligation mixture was transformed into competent *E. coli* XL-1 Blue (Stratagene, La Jolla, USA) according to standard methods, as described in Sambrook et al. (Molecular Cloning. A Laboratory Manual, Cold Spring Harbor, (1989)). Plasmid-carrying cells were selected for by plating out onto ampicillin (50 µg/ml)- and kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK2.

The vector pCLiK2 was cleaved with the restriction endonuclease DraI (New England Biolabs, Beverly, USA). After electrophoresis in 0.8% strength agarose gel, an approx. 2.3 kb vector fragment was isolated using the GFX™PCR, DNA and gel band purification kit (Amersham Pharmacia, Freiburg) according to the manufacturer's instructions. This vector fragment was religated with the aid of the rapid DNA ligation kit (Roche Diagnostics, Mannheim) according to the manufacturer's instructions and the ligation mixture was transformed into competent *E. coli* XL-1 Blue (Stratagene, La Jolla, USA) according to standard methods, as described in Sambrook et al. (Molecular Cloning. A Laboratory Manual, Cold Spring Harbor, (1989)). Plasmid-carrying cells were selected for by plating out onto kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK3.

Starting from plasmid pWLQ2 (Liebl et al., 1992) as template for a PCR reaction, the origin of replication pHM1519 was amplified using the oligonucleotides cg1 (SEQ ID NO:51) and cg2 (SEQ ID NO:52).

```
cg1 (SEQ ID NO: 51):
5'-GAGAGGGCGGCCGCGCAAAGTCCCGCTTCGTGAA-3' cg2 (SEQ ID NO: 52):
5'-GAGAGGGCGGCCGCTCAAGTCGGTCAAGCCACGC-3'
```

Apart from the sequences complementary to pWLQ2, the oligonucleotides cg1 (SEQ ID NO:51) and cg2 (SEQ ID NO:52) contain cleavage sites for the restriction endonuclease NotI. The PCR reaction was carried out using PfuTurbo polymerase (Stratagene, La Jolla, USA) according to a standard method such as that of Innis et al. (PCR Protocols. A Guide to Methods and Applications, Academic Press (1990)). The DNA fragment obtained was approximately 2.7 kb in size and was purified using the GFX™PCR, DNA and gel band purification kit (Amersham Pharmacia, Freiburg) according to the manufacturer's instructions. The DNA fragment was cleaved with restriction endonuclease NotI (New England Biolabs, Beverly, USA) and, following that, again purified using the GFX™PCR, DNA and gel band purification kit (Amersham Pharmacia, Freiburg) according to the manufacturer's instructions. The vector pCLiK3 was likewise cleaved with the restriction endonuclease NotI and dephosphorylated using alkaline phosphatase (Roche Diagnostics, Mannheim) according to the manufacturer's instructions. After electrophoresis in a 0.8% strength agarose gel, the linearized vector (approx. 2.3 kb) was isolated using the GFX™PCR, DNA and gel band purification kit (Amersham Pharmacia, Freiburg) according to the manufacturer's instructions. This vector fragment was ligated with the cleaved PCR fragment with the aid of the rapid DNA ligation kit (Roche Diagnostics, Mannheim) according to the manufacturer's instructions and the ligation mixture was transformed into competent *E. coli* XL-1 Blue (Stratagene, La Jolla, USA) according to standard methods, as described in Sambrook et al. (Molecular Cloning. A Laboratory Manual, Cold Spring Harbor, (1989)). Plasmid-carrying cells were selected for by plating out onto kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK5.

PCLik5 was extended by a multiple cloning site (MCS) by combining the two synthetic essentially complementary oligonucleotides HS445 ((SEQ ID NO:53) and HS446 (SEQ ID NO:54)) which contain cleavage sites for the restriction endonucleases SwaI, XhoI, AatI, ApaI, Asp718, MluI, NdeI, SpeI, EcoRV, SalI, ClaI, BamHI, XbaI and SmaI to give a double-stranded DNA fragment by heating them together to 95° C. followed by slow cooling.

HS445 (SEQ ID NO: 53):
5'-TCGAATTTAAATCTCGAGAGGCCTGACGTCGGGCCCGGTACCACGCGTCATATGACTAG

TTCGGACCTAGGGATATCGTCGACATCGATGCTCTTCTGCGTTAATTAACAATTGGGATCC

TCTAGACCCGGGATTTAAAT-3'

HS446 (SEQ ID NO: 54):
5'-GATCATTTAAATCCCGGGTCTAGAGGATCCCAATTGTTAATTAACGCAGAAGAGCATCGA

TGTCGACGATATCCCTAGGTCCGAACTAGTCATATGACGCGTGGTACCGGGCCCGACGTC

AGGCCTCTCGAGATTTAAAT-3'

The vector pCLiK5 was cleaved with the restriction endonucleases XhoI and BamHI (New England Biolabs, Beverly, USA) and dephosphorylated using alkaline phosphatase (I (Roche Diagnostics, Mannheim)) according to the manufacturer's instructions. After electrophoresis in a 0.8% strength agarose gel, the linearized vector (approx. 5.0 kb) was isolated using the GFX™PCR, DNA and gel band purification kit (Amersham Pharmacia, Freiburg) according to the manufacturer's instructions. This vector fragment was ligated with the synthetic double-stranded DNA fragment with the aid of the rapid DNA ligation kit (Roche Diagnostics, Mannheim) according to the manufacturer's instructions and the ligation mixture was transformed into competent E. coli XL-1 Blue (Stratagene, La Jolla, USA) according to standard methods as described Sambrook et al. (Molecular Cloning. A Laboratory Manual, Cold Spring Harbor (1989)). Plasmid-carrying cells were selected for by plating out onto kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests.

The plasmid obtained in this way is denoted pCLiK5MCS.

Sequencing reactions were carried out according to Sanger et al. (1977) Proceedings of the National Academy of Sciences USA 74:5463–5467. The sequencing reactions were fractionated and analyzed by means of ABI Prism 377 (PE Applied Biosystems, Weiterstadt).

The resultant plasmid pCLiK5MCS is listed as SEQ ID NO: 57.

EXAMPLE 2

Construction of pCLiK5MCS Integrativ sacB

Starting from the plasmid pK19mob (Schäfer et al., Gene 145, 69–73(1994)) as template for a PCR reaction, the Bacillus subtilis sacB gene (coding for levan sucrase) was amplified using the oligonucleotides BK1732 and BK1733.

BK1732 (SEQ ID NO: 55):
5'-GAGAGCGGCCGCCGATCCTTTTTAACCCATCAC-3'

BK1733 (SEQ ID NO: 56):
5'-AGGAGCGGCCGCCATCGGCATTTTCTTTTGCG-3'

Apart from the sequences complementary to pEK19mobsac, the oligonucleotides BK1732 and BK1733 contain cleavage sites for the restriction endonuclease NotI. The PCR reaction was carried out using PfuTurbo polymerase (Stratagene, La Jolla, USA) using a standard method like that of Innis et al. (PCR Protocols. A Guide to Methods and Applications, Academic Press (1990)). The DNA fragment obtained of approximately 1.9 kb in size was purified using the GFX™PCR, DNA and gel band purification kit (Amersham Pharmacia, Freiburg) according to the manufacturer's instructions. The DNA fragment was cleaved with the restriction endonuclease NotI (New England Biolabs, Beverly, USA) and, following that, again purified using the GFX™PCR, DNA and gel band purification kit (Amersham Pharmacia, Freiburg) according to the manufacturer's instructions.

The vector pCLiK5MCS (prepared according to example 1) was likewise cleaved with the restriction endonuclease NotI and dephosphorylated using alkali phosphatase (I (Roche Diagnostics, Mannheim)) according to the manufacturer's instructions. After electrophoresis in a 0.8% strength agarose gel, an approximately 2.4 kb in size vector fragment was isolated using the GFX™PCR, DNA and gel band purification kit (Amersham Pharmacia, Freiburg) according to the manufacturer's instructions. This vector fragment was ligated with the cleaved PCR fragment with the aid of the rapid DNA ligation kit (Roche Diagnostics, Mannheim) according to the manufacturer's instructions and the ligation mixture was transformed into competent E. coli XL-1 Blue (Stratagene, La Jolla, USA) according to standard methods, as described in Sambrook et al. (Molecular Cloning. A Laboratory Manual, Cold Spring Harbor, (1989)). Plasmid-carrying cells were selected for by plating out onto kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK5MCS integrativ sacB.

Sequencing reactions were carried out according to Sanger et al. (1977) Proceedings of the National Academy of Sciences USA 74:5463–5467. The sequencing reactions were fractionated and analyzed by means of ABI Prism 377 (PE Applied Biosystems, Weiterstadt).

The resultant plasmid pCLiK5MCS integrativ sacB is listed as SEQ ID NO: 58.

It is possible to prepare in an analog manner further vectors which are suitable for the inventive expression or overproduction of metA genes.

EXAMPLE 3

Isolation of the lysC Gene from C. glutamicum Strain LU1479

The first step of the strain construction is intended as an allelic substitution of the lysC wild-type gene encoding the enzyme aspartate kinase in *C. glutamicum* ATCC13032, hereinbelow referred to as LU1479. It is intended to carry out a nucleotide substitution in the LysC gene so that, in the resulting protein, the amino acid Thr at position 311 is exchanged for the amino acid Ile.

Starting with the chromosomal DNA from LU1479 as the template for a PCR reaction, an amplification was performed with the oligonucleotide primers SEQ ID NO:59 and SEQ ID NO:60 lysC with the aid of the Pfu-Turbo PCR system (Stratagene USA) following the manufacturer's instructions. Chromosomal DNA from *C. glutamicum* ATCC 13032 was prepared as described by Tauch et al. (1995) Plasmid 33:168–179 or Eikmanns et al. (1994) Microbiology 140: 1817–1828. The amplified fragment is flanked at its 5' end by an SalI restriction cleavage and at its 3' end by an MluI restriction cleavage. Prior to cloning, the amplified fragment was digested by these two restriction enzymes and purified with GFX™PCR, DNA and Gel Band Purification Kit (Amersham Pharmacia, Freiburg).

```
SEQ ID NO: 59
5'-GAGAGAGAGACGCGTCCCAGTGGCTGAGACGCATC-3'

SEQ ID NO: 60
5'-CTCTCTCTGTCGACGAATTCAATCTTACGGCCTG-3'
```

The resulting polynucleotide was cloned into pCLIK5 MCS integrativ SacB (hereinbelow referred to as pCIS; SEQ ID NO: 58 of Example 2) via the SalI and MluI restriction cleavages and transformed into *E. coli* XL-1 blue. Selection for plasmid-bearing cells was achieved by plating on kanamycin (20 µg/ml)-containing LB Agar (Lennox, 1955, Virology, 1:190). The plasmid was isolated and the expected nucleotide sequence was verified by sequencing. The plasmid DNA was prepared by methods of, and using materials from, Quiagen. Sequencing reactions were carried out as described by Sanger et al. (1977) Proceedings of the National Academy of Sciences USA 74:5463–5467. The sequencing reactions were separated using ABI Prism 377 (PE Applied Biosystems, Weiterstadt) and evaluated. The resulting plasmid pCIS lysC is shown as SEQ ID NO:61. The corresponding plasmid map is shown in FIG. 1.

Sequence SEQ ID NO:61 encompasses the following essential part-regions:

| LOCUS FEATURES | pCIS\lysC  5860 bp  DNA  circular Location/Qualifiers |
|---|---|
| CDS[1] | 155 . . . 1420 /vntifkey = "4" /label = lysC |
| CDS | complement[2](3935 . . . 5356) /vntifkey = "4" /label = sacB\(*Bacillus\subtilis*) |
| promoter | complement(5357 . . . 5819) /vntifkey = "30" /label = Promotor\sacB |
| C_region | complement(3913 . . . 3934) /vntifkey = "2" /label = sacB\downstream region |
| CDS | 1974 . . . 2765 /vntifkey = "4" /label = Kan\R |
| CDS | complement(3032 . . . 3892) /vntifkey = "4" /label = Ori\-EC\(pMB) |

[1])coding sequence
[2])on the complementary strand

EXAMPLE 4

Mutagenesis of the *C. glutamicum* lysC Gene

Site-specific mutagenesis of the *C. glutamicum* lysC gene (example 3) was carried out using the QuickChange Kit (Stratagene/USA) following the manufacturer's instructions. The mutagenesis was carried out in the plasmid pCIS lysC, SEQ ID NO:61. The following oligonucleotide primers were synthesized for the exchange of thr311 for 311ile with the aid of the Quickchange method (Stratagene):

```
SEQ ID NO: 62
5'-CGGCACCACCGACATCATCTTCACCTGCCCTCGTTCCG-3'

SEQ ID NO: 63
5'-CGGAACGAGGGCAGGTGAAGATGATGTCGGTGGTGCCG-3'
```

The use of these oligonucleotide primers in the Quickchange reaction leads to a substitution of the nucleotide in position 932 (T being substituted for C) in the lysC gene (cf. SEQ ID NO:64) and to an amino acid substitution in position 311 (Thr→Ile) in the corresponding enzyme (cf. SEQ ID NO:65). The resulting amino acid substitution Thr311Ile in the lysC gene was verified by sequencing after transformation into *E. coli* XL1-blue and plasmid preparation. The plasmid was named pCIS lysC thr311ile and is shown as SEQ ID NO:66. The corresponding plasmid map is shown in FIG. 2.

Sequence SEQ ID NO:66 encompasses the following essential part regions:

| LOCUS FEATURES | pCIS\lysC\thr311ile  5860 bp  DNA  circular Location/Qualifiers |
|---|---|
| CDS[1] | 155 . . . 1420 /vntifkey = "4" /label = lysC |
| CDS | complement[2](3935 . . . 5356) /vntifkey = "4" /label = sacB\(*Bacillus\subtilis*) |
| promoter | complement(5357 . . . 5819) /vntifkey = "30" /label = Promotor\sacB |
| C_region | complement(3913 . . . 3934) /vntifkey = "2" /label = sacB\downstream region |
| CDS | 1974 . . . 2765 /vntifkey = "4" /label = Kan\R |
| CDS | complement(3032 . . . 3892) /vntifkey = "4" /label = Ori\-EC\(pMB) |

[1])coding sequence
[2])on the complementary strand

The plasmid pCIS lysC thr311ile was transformed into *C. glutamicum* LU1479 by means of electroporation as described by Liebl, et al. (1989) FEMS Microbiology Letters 53:299–303. Modifications of the protocol are described in DE-A-10046870. The chromosomal arrangement of the lysC locus of individual transformants was checked using standard methods by Southern blot and hybridization as described by Sambrook et al. (1989), Molecular Cloning. A Laboratory Manual, Cold Spring Harbor. It was thus ensured that the transformants were those which have the transformed plasmid integrated at the lysC locus by homologous recombination. After such colonies had grown overnight in media without antibiotic, the cells were plated onto a sucrose-CM agar medium (10% sucrose) and incubated for 24 hours at 30° C.

Since the sacB gene which is present in the vector pCIS lysC thr311ile converts sucrose into a toxic product, only those colonies which have the sacB gene deleted between the wild-type lysC gene and the mutated gene lysC thr311ile by a second homologous recombination step are capable of growing. Either the wild-type gene or the mutated gene together with the sacB gene can be deleted during homologous recombination. When the sacB gene is removed together with the wild-type gene, a mutated transformant results.

Growing colonies were picked and examined for a kanamycin-sensitive phenotype. Clones with deleted SacB gene must simultaneously show kanamycin-sensitive growth behavior. Such Kan-sensitive clones were studied in a shake flask for their lysine productivity (see example 6). The untreated strain LU1479 was grown for comparison purposes. Clones whose lysin production was increased over that of the control were selected, chromosomal DNA was obtained, and the corresponding region of the lysC gene was amplified by PCR reaction and sequenced. One such clone with the property of an increased lysine synthesis and confirmed mutation in lysC at position 932 was named LU1479 lysC 311ile.

EXAMPLE 5

Preparation of Ethionine-Resistant *C. glutamicum* Strains

In the second strain construction step, the resulting strain LU1479 lysC 311ile (example 4) was treated in order to induce resistance to ethionine (Kase, H. Nakayama K. Agr. Biol. Chem. 39 153–106 1975 L-methionine production by methionine analog-resistant mutants of *Corynebacterium glutamicum*): an overnight culture in BHI medium (Difco) was washed in citrate buffer (50 mM pH 5.5) and treated for 20 min at 30° C. with N-methylnitrosoguanidine (10 mg/ml in 50 mM citrate pH 5.5). After treatment with the chemical mutagen N-methylnitrosoguanidine, the cells were washed (citrate buffer 50 mM pH 5.5) and plated out on a medium composed of the following components, based on 500 ml: 10 g $(NH_4)_2SO_4$, 0.5 g $KH_2PO_4$, 0.5 g $K_2HPO_4$, 0.125 g $MgSO_4.7H_2O$, 21 g MOPS, 50 mg $CaCl_2$, 15 mg proteocatechuate, 0.5 mg biotin, 1 mg thiamine, 5 g/l D,L-ethionine (Sigma Chemicals Deutschland), pH 7.0. In addition, the medium comprised 0.5 ml of a microsalt solution of: 10 g/l $FeSO_4.7H_2O$, 1 g/l $MnSO_4*H_2O$, 0.1 g/l $ZnSO_4.7H_2O$, 0.02 g/l $CuSO_4$, 0.002 g/l $NiCl_2*6H_2O$; all salts were dissolved in 0.1 M HCl. The finished medium was filter-sterilized and, after addition of 40 ml of sterile 50% glucose solution, liquid sterile agar was added in a final concentration of 1.5% agar and the mixture was poured into culture dishes.

Cells which had undergone mutagenic treatment were applied to plates containing the above-described medium and incubated for 3–7 days at 30° C. Resulting clones were isolated, and individual clones were isolated at least once on the selection medium and then analyzed for their methionine productivity in a shake flask in medium 11 (see example 6

EXAMPLE 6

Preparation of Methionine Using the Strain LU1479 lysC 311ile ET-16

The strains generated in Example 5 were grown for 2 days at 30° C. on an agar plate comprising CM medium.

CM agar:
10.0 g/l D-glucose, 2.5 g/l NaCl, 2.0 g/l urea, 10.0 g/l Bacto peptone (Difco), 5.0 g/l yeast extract (Difco), 5.0 g/l beef extract (Difco), 22.0 g/l agar (Difco), autoclaved (20 min., 121° C.)

The cells were subsequently scraped from the plate and resuspended in saline. For the main culture, 10 ml of medium If and 0.5 g of autoclaved $CaCO_3$ (Riedel de Haen) in a 100 ml Erlenmeyer flask were inoculated with the cell suspension to an OD 600 nm of 1.5 and incubated for 72 h at 30° C. on an orbital shaker at 200 rpm.

Medium II:

| 40 g/l | sucrose |
|---|---|
| 60 g/l | molasses (based on 100% sugar content) |
| 10 g/l | $(NH_4)_2SO_4$ |
| 0.4 g/l | $MgSO_4*7H_2O$ |
| 0.6 g/l | $KH_2PO_4$ |
| 0.3 mg/l | thiamine*HCl |
| 1 mg/l | biotin (from a 1 mg/ml filter-sterilized stock solution brought to pH 8.0 with $NH_4OH$) |
| 2 mg/l | $FeSO_4$ |
| 2 mg/l | $MnSO_4$ | a pH of 7.8 was established with $NH_4OH$ and the mixture was autoclaved (121° C., 20 min). In addition, vitamin B12 (hydroxycobalamin Sigma Chemicals) was added from a stock solution (200 µg/ml, filter-sterilized) to a final concentration of 100 µg/l Methionine formed, as well as other amino acids in the culture broth, were with the aid of the Agilent amino acid acid determination method on an Agilent 1100 Series LC System HPLC. Pre-column derivatization with ortho-phtalaldehyde allowed the amount of the amino acid formed to be determined. The amino acid mixture was separated on a column. The amino acid mixture was separated on a Hypersil AA column (Agilent).

Clones whose methionine productivity was at least twice as high as that of the original strain LU1479 lysC 311ile were isolated. One such clone was employed in the further experiment and was named LU1479 lysC 311ile ET-16.

EXAMPLE 7

Cloning metA from *Corynebacterium diphtheriae* and Cloning into the Plasmid pC metA_Cd Chromosomal DNA of *Corynebacterum diphtheriae* was obtained from the American Type Strain Culture Collection (ATCC, Atlanta-USA), Cat. No. 700971 D from strain ATCC 700971.

Using the oligonucleotide primers SEQ ID NO:67 and SEQ ID NO:68, the *C. diphtheriae* chromosomal DNA as template and Pfu Turbo polymerase (Stratagene), a DNA fragment of approx. 1.4 kb, which comprises the metA gene including a noncoding 5' region (promoter region), was amplified with the aid of the polymerase chain reaction (PCR) following standard methods such as Innis et al.

(1990) PCR Protocols. A Guide to Methods and Applications, Academic Press. The amplified fragment is flanked at its 5' end by an XhoI restriction cleavage site and at the 3' end by an NdeI restriction cleavage site, which had been introduced via the oligonucleotide primers.

```
SEQ ID NO: 67
5'-GAGACTCGAGGTTGGCTGGTCATCATAGG-3' and

SEQ ID NO: 76
5' GAAGAGAGCATATGTCAGCGCTCTAGTTTGGTTC-3'
```

The resulting DNA fragment was purified with the GFX™PCR, DNA and Gel Band Purification Kit (Amersham Pharmacia, Freiburg) following the manufacturer's instructions. Thereafter, it was cleaved with the restriction enzymes XhoI and NdeI (Roche Diagnostics, Mannheim) and separated by gel electrophoresis. The approximately 1.4 kb DNA fragment was subsequently isolated from the agarose using the GFX™PCR, DNA and Gel Band Purification Kit (Amersham Pharmacia, Freiburg).

The vector pClik5MCS SEQ ID NO: 57, hereinbelow referred to as pC, was cut with the restriction enzymes XhoI and NdeI (Roche Diagnostics, Mannheim), and an approximately 5 kb fragment was separated by electrophoresis and then isolated using the GFX™PCR, DNA and Gel Band Purification Kit.

The vector fragment was ligated together with the PCR fragment with the aid of the Rapid DNA Ligation Kit (Roche Diagnostics, Mannheim) following the manufacturer's instructions, and the ligation reaction was transformed into competent *E. coli* XL-1 Blue (Stratagene, La Jolla, USA) using standard methods as described in Sambrook et al. (Molecular Cloning. A Laboratory Manual, Cold Spring Harbor, (1989)). A selection for plasmid-bearing cells was achieved by plating onto kanamycin (20 μg/ml)-containing LB agar (Lennox, 1955, Virology, 1:190).

The plasmid DNA was prepared using methods of, and materials from, Quiagen. Sequencing reactions were carried out as described by Sanger et al. (1977) Proceedings of the National Academy of Sciences USA 74:5463–5467. The sequencing reactions were separated and evaluated by means of ABI Prism 377 (PE Applied Biosystems, Weiterstadt).

The resulting plasmid pC metA-Cd (*Corynebacterium diphthedae*) is shown as SEQ ID NO:69. The corresponding plasmid map is shown in FIG. 3.

| LOCUS<br>FEATURES | pC_metA_Cd 6472 bp DNA circular<br>Location/Qualifiers |
|---|---|
| CDS | 313 . . . 1416<br>/vntifkey = "4"<br>/label = metA*Corynebacterium**diphtheriae* |
| CDS | 1838 . . . 2629<br>/vntifkey = "4"<br>/label = Kan\R |
| CDS | 4910 . . . 6031<br>/vntifkey = "4"<br>/label = Rep\Protein |
| CDS | 3902 . . . 4576<br>/vntifkey = "4"<br>/label = ORF\1 |
| CDS | complement(2896 . . . 3756)<br>/vntifkey = "4"<br>/label = Ori\-EC\(pMB) |

EXAMPLE 8

Transformation of the Strain LU1479 lysC 311ile ET-16 with the Plasmid pC metA_Cd The strain LU1479 lysC 311 ile ET-16 was transformed with the plasmid pC metA_Cd by the above-described method (Liebl, et al. (1989) FEMS Microbiology Letters 53:299–303). The transformation mixture was plated onto CM plates which additionally comprise 20 mg/l kanamycin in order to obtain a selection for plasmid-containing cells. Resulting Kan-resistant clones were picked and individual clones were isolated. The methionine productivity of the clones was studied in a shake-flask experiment (see Example 6). The strain LU1479 lysC 311ile ET-16 pC metA_Cd produced significantly more methionine in comparison with LU1479 lysC 311ile ET-16

We claim:

1. A method for the fermentative production of L-methionine, which comprises the following steps:

a) fermenting in a medium cells of coryneform bacterium *Corynebacterium glutamicum* for producing L-methionine, said coryneform bacteria expressing at least one heterologous nucleotide sequence which encodes for a protein with homoserine O-acetyltransferase (metA) activity, wherein said heterologous nucleotide sequence comprises a nucleotide sequence encoding a metA protein derived from *Corynebacterium diphteriae* having an amino acid sequence as set forth in SEQ ID NO: 2;

b) concentrating L-methionine in the medium or in the bacterial cells, and c) isolating L-methionine.

2. The method as claimed in claim 1, wherein the metA-encoding nucleotide sequence comprises a coding sequence as set forth in SEQ ID NO:1.

3. The method as claimed in claim 1, wherein the metA encoding sequence is a DNA or RNA which can be replicated in coryneform bacteria or is stably integrated into the chromosome.

4. The method as claimed in claim 3, wherein a) a bacteria strain transformed with a plasmid vector carrying at least one copy of the metA encoding sequence under the control of regulatory sequences is used, or b) a strain in which the metA encoding sequence has been integrated into the bacteria chromosome is used.

5. The method as claimed in claim 1, wherein the metA encoding sequence is overexpressed.

6. The method as claimed in claim 1, wherein bacteria are fermented in which additionally at least one farther gene of the biosynthetic pathway of L-methionine has been overexpressed.

7. The method of claim 1, wherein coryneform bacteria are fermented in which, at the same time, a lysC gene derived from a coryneform bacterium, which encodes an aspartate kinase, is overexpressed.

8. A method for the production of L-methionine, which comprises the following steps:

a) fermenting in a medium cells of a coryneform bacterium for producing L-methionine, said coryneform bacteria expressing at least one heterologous nucleotide sequence which encodes for a protein with homoserine O-acetyltransferase (metA) activity, wherein the heterologous nucleotide sequence comprises a nucleotide sequence having 95% identity or more to the sequence as set forth in SEQ ID NO: 1;

b) concentrating L-methionine in the medium or in the bacterial cells; and c) isolating L-methionine.

9. The method of claim 8, wherein the coryneform bacterium is of the species *Corynebacterium glutamicum*.

10. The method of claim 8, wherein the metA-encoding nucleotide sequence comprises a nucleotide sequence as set forth in SEQ ID NO:1.

11. The method of claim 8, wherein the metA-encoding nucleotide sequence encodes a protein with metA activity, said protein comprising an amino acid sequence as set forth in SEQ ID NO: 2.

12. The method of claim 8, wherein the metA encoding sequence is a DNA or RNA which can be replicated in coryneform bacteria or is stably integrated into the chromosome.

13. The method of claim 8, wherein a) a bacteria strain transformed with a plasmid vector carrying at least one copy of the metA encoding sequence under the control of regulatory sequences is used, or b) a strain in which the metA encoding sequence has been integrated into the bacteria chromosome is used.

14. The method of claim 8, wherein the metA encoding sequence is overexpressed.

15. The method of claim 8, wherein bacteria are fermented in which additionally at least one further gene of the biosynthetic pathway of L-methionine has been overexpressed.

16. A method for the production of L-methionine, which comprises the following steps:

a) fermenting in a medium cells of a coryneform bacterium for producing of L-methionine, said coryneform bacteria expressing at least one heterologous nucleotide sequence which codes for a protein with homoserine O-acetyltransferase (metA) activity, wherein said heterologous nucleotide sequence comprises a nucleotide sequence encoding a metA protein having an amino acid sequence with 95% homology or more to the sequence as set forth in SEQ ID NO: 2 derived from *Corynebacterium diphteriae*;

b) concentrating L-methionine in the medium or in the bacterial cells; and c) isolating L-methionine.

17. The method of claim 16, wherein the metA encoding sequence is a DNA or RNA which can be replicated in coryneform bacteria or is stably integrated into the chromosome.

18. The method of claim 16, wherein a) a bacteria strain transformed with a plasmid vector carrying at least one copy of the metA encoding sequence under the control of regulatory sequences is used, or b) a strain in which the metA encoding sequence has been integrated into the bacteria chromosome is used.

19. The method of claim 16, wherein the metA encoding sequence is overexpressed.

20. The method of claim 16, wherein bacteria are fermented in which additionally at least one further gene of the biosynthetic pathway of L-methionine has been overexpressed.

21. The method of claim 16, wherein the coryneform bacterium is of the species *Corynebacterium glutamicum*.

* * * * *

UNITED STATES PATENT AND TRADEMARK OFFICE
CERTIFICATE OF CORRECTION

| | | |
|---|---|---|
| PATENT NO. | : 7,238,502 B2 | Page 1 of 1 |
| APPLICATION NO. | : 10/525674 | |
| DATED | : July 3, 2007 | |
| INVENTOR(S) | : Burkhard Kröger et al. | |

It is certified that error appears in the above-identified patent and that said Letters Patent is hereby corrected as shown below:

In Claim 6, in column 178, on line 53, "fermented in which additionally at least one farther gene of" should read -- fermented in which additionally at least one further gene of --.

Signed and Sealed this

First Day of April, 2008

JON W. DUDAS
*Director of the United States Patent and Trademark Office*